(12) United States Patent
Gielen et al.

(10) Patent No.: US 8,796,506 B2
(45) Date of Patent: Aug. 5, 2014

(54) TRANSGENIC SUGAR BEET PLANTS

(75) Inventors: Johannes Jacobus Ludgerus Gielen, Bouloc (FR); Thomas Craft, Lund (SE); Pierre Pin, Malmo (SE)

(73) Assignee: Syngenta Participations AG, Basel (CH)

( * ) Notice: Subject to any disclaimer, the term of this patent is extended or adjusted under 35 U.S.C. 154(b) by 262 days.

(21) Appl. No.: 12/994,452

(22) PCT Filed: May 25, 2009

(86) PCT No.: PCT/EP2009/056262
§ 371 (c)(1),
(2), (4) Date: Feb. 21, 2011

(87) PCT Pub. No.: WO2009/141446
PCT Pub. Date: Nov. 26, 2009

(65) Prior Publication Data
US 2011/0138492 A1 Jun. 9, 2011

(30) Foreign Application Priority Data

May 23, 2008 (WO) ................. PCT/EP2008/056390

(51) Int. Cl.
*C12N 15/82* (2006.01)
*C07H 21/04* (2006.01)
*A01H 5/00* (2006.01)
*C07K 14/415* (2006.01)

(52) U.S. Cl.
CPC .................................. *C07K 14/415* (2013.01)
USPC ......... 800/285; 435/320.1; 435/419; 800/298

(58) Field of Classification Search
None
See application file for complete search history.

(56) References Cited

U.S. PATENT DOCUMENTS 7,507,875 B2 * 3/2009 Bloksberg et al. ............. 800/278
2010/0209919 A1 * 8/2010 Gielen et al. ....................... 435/6

FOREIGN PATENT DOCUMENTS

| WO | WO 2007/005305 A1 | 1/2007 |
| WO | WO 2007/122086 A1 | 11/2007 |
| WO | WO 2007122086 A1 * | 11/2007 |

OTHER PUBLICATIONS

Hoffman et al, 2003, Mol. Gen. Genomics., 269:126-136.*
Thomas et al, 2001, Plant J., 25:417-425.*
Feil et al, 2003, Euphytica, 130:163-165.*
Abe, J., et al., "A Marker-assisted Analysis of Bolting Tendency in Sugar Beet (*Beta vulgaris* L.)," *Euphytica*, 1997, pp. 137-144, vol. 94, No. 2.
El-Mezaway, A., et al., "High-resolution Mapping of the Bolting Gene *B* of Sugar Beet," *Theor. Appl. Genet.*, Jul. 2002, pp. 100-105, vol. 105, No. 1.
Gaafar, R.M., et al., "Bacterial Artificial Chromosome-derived Molecular Markers for Early Bolting in Sugar Beet," *Theor. Appl. Genet.*, Apr. 1, 2005, pp. 1027-1037, vol. 110, No. 6.
Hohmann, U., et al., "A Bacterial Artificial Chromosome (BAC) Library of Sugar Beet and a Physical Map of the Region Encompassing the Bolting Gene B," *Mol Gen Genomics*, Apr. 2003, pp. 126-136, vol. 269, No. 1.
International Search Report for related application PCT/EP2008/056930, filed May 23, 2008.

* cited by examiner

*Primary Examiner* — Ashwin Mehta
*Assistant Examiner* — Jason Deveau Rosen
(74) *Attorney, Agent, or Firm* — Joshua L. Price

(57) ABSTRACT

The invention relates to transgenic sugar beet plants having a phenotype of delayed bolting. The invention further relates to polynucleotides that are closely linked to the bolting gene or B gene within the sugar beet genome and can be used for the discrimination between the annual and biennial genotype or between different haplotypes within plant groupings of sugar beet plants exhibiting a biennial genotype.

6 Claims, 14 Drawing Sheets

Figure 4:
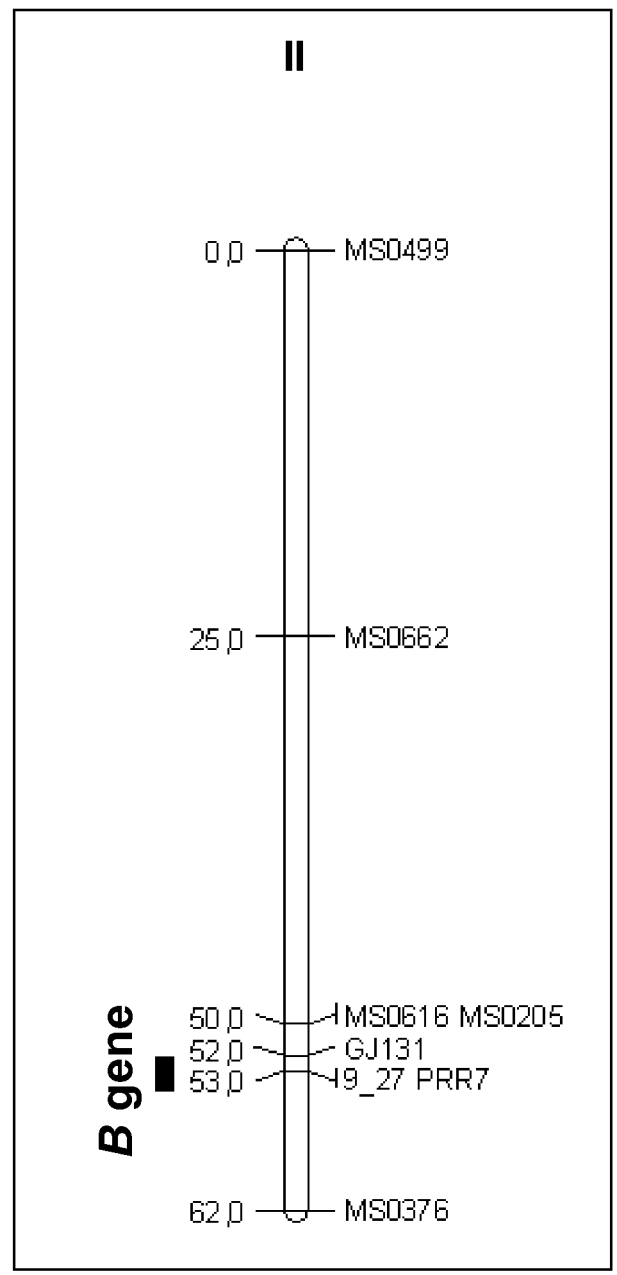

```
Ec (1ZH4_A)    2 .[75].V S       RS.[3]. KIA  D    D   S  FGIGE QA.[3]. 113
Bv (CV301305)  1       MM S      S D.[3].L LKC SK  V   VK IRKNE KN.[3].  37
Kp (P21649)   58 .[78].FI        WK.[1].H  E FELE     IL YQES IIN.[3]. 170
Bs (P13800)    4 .[78].I         I D.[3].Y TH  T  RG  L EM ADT I .[3]. 118
Sc (Q04942)    2 .[75].L         RN.[3].D  VG ES  D  VV  VQGRV D .[3]. 113
St (P25852)    6 .[76].IM        FS.[3].T  E   A  L   I  LDFD  Q .[3]. 118
Pa (Q00934)    4 .[76].MI        YG.[3].T IQ       T   VDLGP R .[3]. 116
Sf (P0AEC4)  526 .[79].A         NV.[2].DKQ Y  N  MD V  S  LSVPA TA.[3]. 640
Bb (P26762)  973 .[81].LFG.[1].TA .[4].E QRCRA  M  C  F  IGVDA RQ.[3]. 1092
Rc (P37740)    3 .[78].F         G A.[3].L  QS       VE  FNDNHIVD.[3]. 117
```

FIGURE 1

```
CV301305   PVIMMSSHDSMGLVLKCLSKGAVDFLVKPIRKNELKNLWQHVWRRCHSSSGSGSESCV-    180
           PVIMMSSHDSMGLV-KCLSKGAVDFLVKPIRKNELK-LWQHVWRRC-SSSGSGSES---
AT-PRR7    PVIMMSSHDSMGLV KCLSKGAVDFLVKPIRKNELK LWQHVWRRC SSSGSGSES       214

CV301305   NGKSSGSKRAASDNDSDIEENNRSIGLQARDGSDNGSGTQSSWTKRAARV-SSPSPQ     357
           --KS-SK---SD-D----E-N-SIGL-A-DGS-GSG-QSSWTK-A--V--SP--
AT-PRR7    TQKSKSKSISSDQDSGSSENNGSIGLNASDGSSGSGAQSSWTKKAVSVDSSPRAV      274

CV301305   STWQATDPPDSTCAQVSPMSEAEASSWN--PGSMELDGQDHKASVPMGSDLEIGSP    531
           S-W-----DSTCAQV----E-F-SN---P-N-E----D----V-MGNDLEI-N-
AT-PRR7    SLWNV----DSTCAQVSNPE-FPSNQVAPPNENTQEHDDKENVTMGNDLEISSR     329

CV301305   RISDSRLNGPNKTVKLATTAEENQYSQLNLNQENDGRSFDENLKNNNKPKSSWTKQAM    711
           R--D--L--P------TT----Q-N--N---------N--LN---P-S-N--
AT-PRR7    RNCDLALE-PKDEPLSKTTGIMRQDNSFNSSSKWKMKVGNGPLNNSESPSSNQNHSDG    388

CV301305   NSPGK-NEEHRNGNSVSNAP    768
           -S--K-N--H-N-NN--AP
AT-PRR7    GSSFKANSSHLNDNNEPNAP    408
```

*FIGURE 2*

```
                        1                                                           60
AtPRR7 CDS       (1)    ATGAATGCTAATGAGGAGGGGGAGGGTTCACGTTACCCAATCACTGATCGAAAGACCCGA
AtPRR7 gene      (1)    ATGAATGCTAATGAGGAGGGGGAGGGTTCACGTTACCCAATCACTGATCGAAAGACCCGA
                        61                                                          120
AtPRR7 CDS      (61)    GAGACGAAATTCGATAGGGTTGAGAGTCGGACAGAGAAGCATAGTGAAGAAGAGAAAACT
AtPRR7 gene     (61)    GAGACGAAATTCGATAGGGTTGAGAGTCGGACAGAGAAGCATAGTGAAGAAGAGAAAACT
                        121                                                         180
AtPRR7 CDS     (121)    AATGGAATTACTATGGATGTGAGAAATGGGAGTTCAGGTGGACTGCAAATTCCATTGTCG
AtPRR7 gene    (121)    AATGGAATTACTATGGATGTGAGAAATGGGAGTTCAGGTGGACTGCAAATTCCATTGTCG
                        181                                                         240
AtPRR7 CDS     (181)    CAACAAACAGCGGCAACTGTCTGTTGGGAAAGGTTTCTTCATGTGAGAACCATTAGAGTT
AtPRR7 gene    (181)    CAACAAACAGCGGCAACTGTCTGTTGGGAAAGGTTTCTTCATGTGAGAACCATTAGAGTT
                        241                                                         300
AtPRR7 CDS     (241)    CTGCTTGTCGAAAATGACGACTGCACTCGTTATACGTTACTGACTTCTTCGCAATTGT
AtPRR7 gene    (241)    CTGCTTGTCGAAAATGACGACTGCACTCGTTATACGTTACTGGACTTCTTCGCAATTGT
                        301                                                         360
AtPRR7 CDS     (301)    AGCTATGAAG---------------------------------------------------
AtPRR7 gene    (301)    AGCTATGAAGGTCAGTTTTGAAGCCTATGGCCCAACTTTAATCTATAGCGCATATATGTA
                        361                                                         420
AtPRR7 CDS     (311)    -------------------------------------------------TTGTTGACG
AtPRR7 gene    (361)    CCCGTTTCGGTTCTGTTTGTTGATTGATTATTATTAACTCTGTCATGGCAGTTGTTGACG
                        421                                                         480
AtPRR7 CDS     (320)    CGTCAAATGGGATACAAGCTTGGAAGGTGTTAGAAGATCTAAACAATCATATTGATATTG
AtPRR7 gene    (421)    CGTCAAATGGGATACAAGCTTGGAAGGTGTTAGAAGATCTAAACAATCATATTGATATTG
                        481                                                         540
AtPRR7 CDS     (380)    TGCTAACAGAGGTGATCATGCCTTACTTATCTGGTATCGGTCTCTTGTGCAAGATTTTGA
AtPRR7 gene    (481)    TGCTAACAGAGGTGATCATGCCTTACTTATCTGGTATCGGTCTCTTGTGCAAGATTTTGA
                        541                                                         600
AtPRR7 CDS     (440)    ACCACAAATCTCGTCGGAACATCCCTGTCATCA---------------------------
AtPRR7 gene    (541)    ACCACAAATCTCGTCGGAACATCCCTGTCATCAGTGAGTTCTTTTTCCTTGGTCGTTTTA
CV301305         (1)    ------------------GCTCCTGTCATTA-----------------------------
                        601                                                         660
AtPRR7 CDS     (473)    ------------------------------------------------------------
AtPRR7 gene    (601)    CATTGAGCTCTTTCTTTTGAAGTTACACGATTTGTTGAGTCTTCTCTAGCGTATGTTGGA
CV301305        (14)    ------------------------------------------------------------
                        661                                                         720
AtPRR7 CDS     (473)    ---------------------------------------------TGATGTCATCTCAT
AtPRR7 gene    (661)    AAGTAGATGCTTTTAACTACATTCCCCTGTGAGATTTGTGTTGCAGTGATGTCATCTCAT
CV301305        (14)    ---------------------------------------------TGATGTCATCTCAT
                        721                                                         780
AtPRR7 CDS     (487)    GACTCAATGGGGCTGGTCTTTAAGTGCTTATCGAAAGGAGCTGTTGACTTTCTTGTTAAG
AtPRR7 gene    (721)    GACTCAATGGGGCTGGTCTTTAAGTGCTTATCGAAAGGAGCTGTTGACTTTCTTGTTAAG
CV301305        (28)    GATTCGATGGGTTTAGTCTTAAAGTGCTTATCCAAGGGCGCTGTTGACTTTCTGGTGAAG
                        781                                                         840
AtPRR7 CDS     (547)    CCAATAAGAAAAAATGAGCTTAAGATCCTTTGGCAGCATCTTTGGAGAAGATGCCAAAGT
AtPRR7 gene    (781)    CCAATAAGAAAAAATGAGCTTAAGATCCTTTGGCAGCATCTTTGGAGAAGATGCCAAAGT
CV301305        (88)    CCTATAAGAAAAAACGAACTTAAAAACCTTTGGCAGCATCTTTGGAGGAGGTGTCACAGT
                        841                                                         900
AtPRR7 CDS     (607)    ------------------------------------------------------------
AtPRR7 gene    (841)    GTATGTCCTTGCTCATATATGATTAATCTGAAAACCTGTTGGTACAACTGGTGATAAGTA
CV301305       (148)    ------------------------------------------------------------
                        901                                                         960
AtPRR7 CDS     (607)    ------------------------------------------------------------
AtPRR7 gene    (901)    GTAAACTAGAAATTCATGGTCTAATTGTGGATTGGTATCTTCTTTTTTTTTTTCCACATG
CV301305       (148)    ------------------------------------------------------------
                        961                                                         1020
AtPRR7 CDS     (607)    ---------------------------------------------TCTAGTGGT
AtPRR7 gene    (961)    ATTGGTATCTTACTTTTTGGTTTCTCATGGTTTTCCTTGTTTCTTGTTCAGTCTAGTGGT
CV301305       (148)    ---------------------------------------------TCTAGTGGT
```

*FIGURE 3-1*

```
                        1021                                                         1080
AtPRR7 CDS    (616)  AGTGGAAGTGAGAGCGGAACGCATCAAACTCAAAAGTCTGTGAAATCGAAAAGTATTAAA
AtPRR7 gene  (1021)  AGTGGAAGTGAGAGCGGAACGCATCAAACTCAAAAGTCTGTGAAATCGAAAAGTATTAAA
   CV301305   (157)  AGTGGAAGTGAAAGCTG..TGTAAGGAATGGAAAATCCATAGGAAGC.AAGAGGGCTGAA
                        1081                                                         1140
AtPRR7 CDS    (676)  AAATCTGATCAAGATTCAGGAAGCAGTGATGAGAATGAAAATGGGAGCATTGGCCTGAAT
AtPRR7 gene  (1081)  AAATCTGATCAAGATTCAGGAAGCAGTGATGAGAATGAAAATGGGAGCATTGGCCTGAAT
   CV301305   (214)  GAGTCGGACAATGACACTGACATCAATGAGGAAGATCATAACAGAAGCATTGGTTTACAA
                        1141                                                         1200
AtPRR7 CDS    (736)  GCTAGTGATGGAAGTAGTGATGGGAGTGGCGCTCAG------------------------
AtPRR7 gene  (1141)  GCTAGTGATGGAAGTAGTGATGGGAGTGGCGCTCAGGTAAGACGAATGTGCAATACCGAT
   CV301305   (274)  GCTCGGGATGGAAGTGACAATGGAAGTGGGACCCAG------------------------
                        1201                                                         1260
AtPRR7 CDS    (772)  ------------------------------------------------------------
AtPRR7 gene  (1201)  AATCTAAATATACACCCGAGAAGCTATCCTTTTAAAAATTTCTTAACCACAAATGATAGG
   CV301305   (310)  ------------------------------------------------------------
                        1261                                                         1320
AtPRR7 CDS    (772)  ------------------------------------------------------------
AtPRR7 gene  (1261)  GGTCGGATGATCGAACTTCGCATGTGCACTCAGATGCTTATAAATGGTGGAAGCGCTTAA
   CV301305   (310)  ------------------------------------------------------------
                        1321                                                         1380
AtPRR7 CDS    (772)  ------------------------------------------------------------
AtPRR7 gene  (1321)  CTAACCAATTGTAGAACTCAATGATGTTTAACTTAGATCTATTCAGTGATAAACTGGGTG
   CV301305   (310)  ------------------------------------------------------------
                        1381                                                         1440
AtPRR7 CDS    (772)  ------------------------------------------------------------
AtPRR7 gene  (1381)  AAAATTTCTAGTTCATTTTGAAGTTTTATTTTGCACATGGTTTATCTCCAAAACCTAGGT
   CV301305   (310)  ------------------------------------------------------------
                        1441                                                         1500
AtPRR7 CDS    (772)  -----------------------------AGCTCTTGCACGAAAAAAGCTGTGGATGTTGA
AtPRR7 gene  (1441)  TGATTTTGACATACCTTTTTTTGTTCAGAGCTCTTGCACGAAAAAAGCTGTGGATGTTGA
   CV301305   (310)  -----------------------------AGTTCATGCACAAAAAGGGCTGCAGAAGTTGA
                        1501                                                         1560
AtPRR7 CDS    (804)  TGACAGTCCACGAGCGGTATCTCTATGGGACCGAGT............TGATAGCACTTG
AtPRR7 gene  (1501)  TGACAGTCCACGAGCGGTATCTCTATGGGACCGAGT............TGATAGCACTTG
   CV301305   (342)  G...AGCCGCCAACCACAGTCTACATGGGAGCAAGCAACTGATCCACCTGATAGCACTTG
```

FIGURE 3-2

```
              1                                                           60
AtPRR3        ------------------------------------------------------------
AtPRR5        MWQTWPRQPILLDIFSNPNTLSTTVRSWSVRHPLSIITVKTFARFFLDIFFSPHYYRKNK
AtPRR9        ------------------------------------------------------------
AtTOC1        ------------------------------------------------------------
AtPRR7        --------------------------------------------------------MNAN
BvPRR7        --------------------------------------------------------MRLIHKN
              61                                                          120
AtPRR3        ----------MCFNNIETGDEVETERQVF--------------------------EFRVE
AtPRR5        VLFFALFSFISPLTNILICFVTVSLSLELSSSSSIIDLGFSKLSVCVVIMTSSEEVVEVT
AtPRR9        --------------------------MSEI---------------VVLSSDGMETI
AtTOC1        ----------------------------------------------------------MD
AtPRR7        EEGEGSRYPITDRKTGETKFDRVESRTEKHS-------------------EESKTNGIT
BvPRR7        EDGPGVAKSVAELNQHIVAVKKEGRGRVAGEG---------------QGLSSEELRII
              121                                                         180
AtPRR3        DTARNTNN----------VQISQQQQQP-LAHVSKSFVERRSLKVLLVEDSSSRHS
AtPRR5        VVKAPEAGGGKLS------RRKIRKKDAGVDGLSKGRPFYKIALVLLAEADSSROII
AtPRR9        KNRVKSSE---------------------VSQRHKYERKTVESLLVESDYSSROSI
AtTOC1        LNGECKGG-------------------------LGSIDRSRVSILLCDSDSTSLGES
AtPRR7        MDVRNGSS----------GGLQIPLSQQTAATVCESSHRTISSLLVSDCSSRYS
BvPRR7        EDGEDANSRRSLSSVQLPVHTHRHQPQVQPQGRSCSRRLSSGSPKSLLVESDSSIRHS
              181                                                         240
AtPRR3        ALLKNCSYSVTIVVTDVSEARRILSEKSCDSVLNESMVHSGTSILSSKTNSNKTL
AtPRR5        ALLVSSCYVSVAASSLSKASEMLKGKPESVDSSLESDSISSGYALSILREHDI
AtPRR9        SLLVSSCYKVSVSSLSASEMLKEKSHNDSSLSSSISGFASLALVKESEAS
AtTOC1        FTLLSEGSYQVTSKSARQVIDALNAEGPDSDILAESISMAKGMKMLRYSTRDSDLRR
AtPRR7        SLLVSCYVSVESASNGIQEMKYLSELNNHDIVSNESMIMRYLSGTSIILCESLNNKSRPS
BvPRR7        SLLVSCYVSVSNGIESMKILSSLSNQSDSSVTSGLSGISILLSKNSSKSSQS
              241                                                         300
AtPRR3        PVIMMSSHDVVVFKCSSNGAVDFLKPSRNELSSSLWHSWRRSH---SGSSSS
AtPRR5        TPVIMMSTGDVSVNTVVKCMLSGAADSYLKPSRNELSSSLWHSWRRQTSLAPDSFPWNS
AtPRR9        PVIMMSGDEVKSIKKSVKCMLSGAADSYLKPSRNELSSSLWHSWRRLT---LRDDPTAHA
AtTOC1        PVIMMSGDEVPWVSKCSSKLGAADSYLKPSRSTNELLSSLWTHSWRRRR---MLGLAEKNM
AtPRR7        PVIMMSSHDSSVVFKCSSNGAVDFSLKPSRNELSSSILWHSWRRSSQ---SGSSS
BvPRR7        TPVIMMSSHDSGSVVFKCSSGAVDFLKPSRNELSSSLWHSWRRSH---SGSSSS
              301                                                         360
AtPRR3        GIHD-KSSVKPESTQGSENSASSSSSHRSESGSSGSSSNQSSGSNSTSGSTSVRPSS
AtPRR5        VGQQKAEGASANNSNGKRDSHVVSGNGGDAQSSCTRPEMEGESADSVEVSARDAVQMECAK
AtPRR9        QSLPASQHNLEDSDETCEDSRYHSSQGSG----AQASSNYNGHNKLMENSKSVDERDEFKE
AtTOC1        LSYDFDLVGSDQSDPNSNSTNLFSSDSTDDRSLRSTNPQRGNLSHQENEWSVATAPVHSRS
AtPRR7        GTHQTQSSSKSKSIKKSSDSSGSSSSSHENSS---GSISSNASSS-SSDSSCASSSSSSKAVS
BvPRR7        CVRNS-GSSSSGSKRAEESSDNSTDSINEESDDS---RSSISQARSSSSDNSSGSSSSSKRPSAE
              361                                                         420
AtPRR3        IKSTSP----S---N----------------Q----FSDAPNKKGTYENGCAHSNRLKS
AtPRR5        SQFNETRLLANESQSK-----------QAEAIDFMGSSFRRTGRRNRESSVAQYESRIS
AtPRR9        IFDVTMDLIG-------------------------QIDKRPDS-ISKDSSRDECVSSSPS
AtTOC1        GGLGADGTATSSSAVTAIEPPLDHSLAGSHHEPMK----RNSNPAQFSSAPSKSSRIKISSES
AtPRR7        VDDSPR--AVS-SWDRVDSTCAQVSHSNPEFPSNQLVASPAEKSTQESDSSFEDSTMSRD
BvPRR7        VESPQPQSTWEQATDPPDSTCAQVSYPMSEAFAS-SWMSGSMQELDGQDHQYDNSPMSKD
              421                                                         480
AtPRR3        ANDQKEQIGSGSQTG----MSMSKKAEEP--GDSEKN-----AKYSSQASSRNSDTLN-
AtPRR5        SDLSLESPNASENQSSGDRPSLHPSSASAFTRYVHRPLQTQCSASPSVTDQRKSVAASQD
AtPRR9        SGLSSLKSCSVSGFEN--QDESKHQKLSLSDASAFSRFEESKSAEKASVASESTSGEPK-
AtTOC1        SAFFTYVKSTSVLRTNGQDPPLVDGNGSLHLHRCSSAEKFQVVASEGINNTKQARRATSKST
AtPRR7        LSSISSIRSNCDLALEPKDEPLSKTTGIMRQD-NSFEKSSSKWKMKVGKGPSDLSSESSSSK
BvPRR7        SSIGVPSSISDSRLNGPNKTSVKLATTASEENQYSQSSDLNQENDGRSFDEENSSMNSDKSKSE
```

FIGURE 6-1

```
         481                                                        540
AtPRR3   --ESS------------------------QVESKAPS---NR LQ EQT  T----
AtPRR5   DNIVLM QYNTSEP--------------PPNAPRRN T FYTGA SPGPPF NQLNSWPG
AtPRR9   -----------------------------TPTESH LRKVTS QG ATT SNQEN---
AtTOC1   V TN QDPPLVNGN-----------GSHHLHRGAA FQV ASEGINNTKQAH SRG-T
AtPRR7   QMHED G SFKAMSSHLQDNREPEAPNTHLKTLDTN A VK S LMHV EH  HRG-T
BvPRR7   W QAM PGKVEEHRRGN----KVSDAPPEISKIK GMQHV MP LVL L LG--D
         541                                                        600
AtPRR3   RE RDYK G S  RH NL    N--G--AT -----------------------
AtPRR5   QSSYP PTPIN  QF DPNT  TSAMAPA SLSPSPSSVSPH YSSMFHPFN---------
AtPRR9   --IG SS SF QVLQ TV NQKQDS IPVE---N----R------------------
AtTOC1   EQYH QGE LQ GASYPHSLEP TL TSMESHGRNY E NMNIPQVAMNR---------
AtPRR7   KD G LVRD  V R EG    A SNANKI GG L STSLQDNN-------------
BvPRR7   IA  T N  L   VG  F     SGTTGNQGTGK V SCSPPNNSSEAAKQSHFDAP
         601                                                        660
AtPRR3   ---------------------------AK A EN ESC PHDSPIAKLLG SSSD PL
AtPRR5   ---------------------------S  GLQ RDCSMDVDERRYV ATEHSAIG
AtPRR9   ---------------------------AASKE AG QSTNEGIAGQ  TEKPKEE
AtTOC1   ---------------------------S DSSQ GSGFSAPNAYPYYMHGVMN V M
AtPRR7   ---------------------SQDLI  T AAY CH NMNESLPHNHR HVGS  FD
BvPRR7   HQISNSSSNNNNMGSTTNKFFKKPAMDID T AKSTVNC HHSHVFEPVQ HMSN  T
         661                                                        720
AtPRR3   K----------------------------------------------------
AtPRR5   NHIDQLIE---------------------------------------------
AtPRR9   E ---------------------------------------------------
AtTOC1   Q AAMMPQYGHQIPHCQPNHPNGMTGYPYYHHP NTSLQHSQMSLQ--------------
AtPRR7   M STTENNAFTKPGAPKVSSAGSSSVKHSSFQP PCDHHNNHASYNLVHVAE--------
BvPRR7   A GKPGVGSVNGMLQENVPVNAVLPQENNVDQQ KIQHHHHYHHYDVHSVQQLPKVSVQH
         721                                                        780
AtPRR3   ---------------------------------------------------------Q-
AtPRR5   ------------------------------------------------------------
AtPRR9   ------------------------------------------------------------
AtTOC1   ------------------------------------------------------------
AtPRR7   -RKK-----LPPQCGSSNVYNETIEGNNNTVNYSVNGSVSGSGHGSNGPYGSSNGMNAGG
BvPRR7   NMPKSKDVTAPPQCGSSNTCRSPIEAN--VANCSLNGSGSGSNHGSNFLNGSSAAVNVEG
         781                                                        840
AtPRR3   --------------------QS  -------D WA RE AL KFR KR RC EKK
AtPRR5   -------------------KKNEDGY LSVGKI QSL RE AL TKFR KR RC EKK
AtPRR9   --------------------- KQRW --------R  AL KFR KR RC KK
AtTOC1   ----------NGQMSMVHH W PA NPPSNEVRV KLDRRE AL KFRKRN QRC KK
AtPRR7   MNMGSDNGAGKNG---NGDG G  G SGNLADE KI  RE AL TKFRQKR KR RC RKK
BvPRR7   TNMVNDSGIAAKDGAENGSG G  G  G VGVDQS S  RE AL NKFR KR RC KK
         841                                                        898
AtPRR3    RYH  RK LA  RPH GQF  RD----------------------DHK GSE N---
AtPRR5    RYE  RK LA  RP I GQF  RQ ---------------------STQ P-------
AtPRR9    R   RK LA  RP V GQF  RT  ----------------------SDA TKS-----
AtTOC1    RYVNRK LA  RP V GQF  M GVNVDLNGQPDSADYDDEEEEEEEEE R SSPQ
AtPRR7    RY   RK LA  RP V GQF   TA---------------------AATDD DIKNIE
BvPRR7    RY   RK LA  RP V GQF  RQ R---------------------ENKGR T S---
AtPRR3   ------
AtPRR5   ------
AtPRR9   ------
AtTOC1   DDALGT
AtPRR7   DS----
BvPRR7   ------
```

FIGURE 6-2

| sources | Spain | Greece | Syngenta annual | Italy | Portugal | USA | Italy | Italy | France | France | France | France | France | France | France | France | France | Italy | UK | Syngenta O-type | Syngenta P-1 | Syngenta P-2 | |
|---|---|---|---|---|---|---|---|---|---|---|---|---|---|---|---|---|---|---|---|---|---|---|---|
| lines | BATRAN | GRE1AN | A610 | ITALAN | PORTAN | USDA-62 | I3B10A | I3F02B | F1A01RO | F1A02RO | F1D08TA | F1D12TA | F1E01TA | F2C06SO | F1H01BA | F2B10VA | F2C12SO | I3D10A | U3A10GB | O018 | P346 | P402 | target |
| phenotype | annual | annual | annual | annual | annual | annual | annual | annual | annual | annual | annual | annual | annual | annual | annual | annual | annual | annual | biennial | biennial | biennial | biennial | |
| nucleotide pos. | | | | | | | | | | | | | | | | | | | | | | | |
| 11360 | A | T | T | T | T | T | T | T | T | T | T | T | T | T | T | T | T | T | A | A | A | A | |
| 11403 | | C | G | G | G | G | G | G | G | G | G | G | G | G | G | G | G | G | | | | | |
| 11404 | | C | C | C | C | C | C | C | C | C | C | C | C | C | C | C | C | C | | | | | |
| 11405 | | G | G | G | G | G | G | G | G | G | G | G | G | G | G | G | G | G | | | | | |
| 11408 | T | G | G | G | G | G | G | G | G | G | G | G | G | G | G | G | G | G | C | C | C | C | |
| 11410 | A | G | G | G | G | G | G | G | G | G | G | G | G | G | G | G | G | G | A | A | A | A | |
| 11411 | A | | | | | | | | | | | | | | | | | | A | A | A | A | |
| 11469 | | | | | | | | | | T | T | T | | | | | | | | | | | |
| 11476 | T | T | | T | | T | T | T | T | T | T | T | T | T | T | T | T | T | T | T | T | T | |
| 11477 | G | G | | G | | G | G | G | G | G | G | G | G | G | G | G | G | G | G | G | G | G | |
| 11478 | A | A | | A | | A | A | A | A | A | A | A | A | A | A | A | A | A | A | A | A | A | |
| 11479 | A | A | | A | | A | A | A | A | A | A | A | A | A | A | A | A | A | A | A | A | A | |
| 11480 | T | T | | T | | T | T | T | T | T | T | T | T | T | T | T | T | T | T | T | T | T | |
| 11481 | G | G | | G | | G | G | G | G | G | G | G | G | G | G | G | G | G | A | A | A | A | |
| 11482 | T | T | | T | | T | T | T | T | T | T | T | T | T | T | T | T | T | T | T | T | T | |
| 11483 | C | C | | C | | C | C | C | C | C | C | C | C | C | C | C | C | C | G | G | G | G | |
| 11487 | C | C | C | C | C | C | C | C | C | C | C | C | C | C | T | T | T | C | C | C | C | C | |
| 11493 | | C | C | C | C | C | C | C | C | C | C | C | C | C | C | C | C | C | | | | | |
| 11494 | | C | C | C | C | C | C | C | C | C | C | C | C | C | C | C | C | C | | | | | |
| 11495 | | A | A | A | A | A | A | A | A | A | A | A | A | A | A | A | A | A | | | | | |
| 11503 | A | G | G | G | G | G | G | G | G | G | G | G | G | G | G | G | G | G | A | A | A | A | |
| 11561 | A | | | | | | | | | | | | | | | | | | A | A | A | A | |
| 11562 | T | | | | | | | | | | | | | | | | | | T | T | T | T | |
| 11563 | T | | | | | | | | | | | | | | | | | | T | T | T | T | |
| 11564 | C | | | | | | | | | | | | | | | | | | C | C | C | C | |
| 11565 | T | | | | | | | | | | | | | | | | | | T | T | T | T | |
| 11566 | C | | | | | | | | | | | | | | | | | | C | C | C | C | |
| 11567 | A | | | | | | | | | | | | | | | | | | A | A | A | A | |
| 11568 | C | | | | | | | | | | | | | | | | | | C | C | C | C | |
| 11584 | A | T | T | T | T | T | T | T | T | T | T | T | T | T | T | T | T | T | A | A | A | A | |
| 11592 | | | | | | | | | | | | | | | | | | | A | A | A | A | * |
| 11787 | A | A | A | A | A | A | A | A | A | A | A | A | A | A | A | A | A | A | T | A | A | A | |
| 11828 | I | D | D | D | D | D | D | D | D | D | D | D | D | D | D | D | D | D | D | D | D | D | |
| 11939 | A | | | | | | | | | | | A | A | A | A | | | | | | | | |
| 11948 | T | C | C | C | C | C | C | C | C | C | C | C | C | C | C | C | C | C | T | T | T | T | |
| 11993 | | T | T | T | T | | T | T | T | T | T | T | T | T | T | T | T | | | | | | |
| 12211 | C | C | C | C | C | C | C | C | C | C | C | C | C | C | T | T | T | C | C | C | C | C | |
| 12316 | A | A | A | A | A | A | A | A | A | A | A | A | A | A | A | A | A | A | G | G | G | G | * |
| 12325 | A | A | A | A | A | A | A | A | A | A | A | A | A | A | A | A | A | T | A | A | A | A | |
| 12404 | | | | | | | | | | | | | | | | | G | | | | | | |
| 12438 | G | G | G | A | A | G | G | G | G | G | G | G | G | G | G | G | G | G | G | G | G | G | |
| 12490 | A | A | A | A | A | A | A | A | A | A | A | A | A | A | A | A | A | A | G | G | G | G | * |
| 12512 | G | G | G | G | G | G | G | G | G | G | G | G | G | G | C | C | C | C | G | G | G | G | |
| 12544 | T | T | T | T | T | T | T | T | T | T | T | T | T | T | T | T | T | T | | | | | * |

*FIGURE 11*

FIGURE 12

TRANSGENIC SUGAR BEET PLANTS

The present invention relates generally to the field of plant molecular biology, plant transformation, and plant breeding. More specifically, the invention relates to transgenic sugar beet plants having a phenotype of delayed bolting. The invention further relates to polynucleotide markers that are closely linked to or residing within the bolting gene or B gene within the sugar beet genome and can be used for the discrimination between the annual and biennial genotype or between different haplotypes within plant groupings of sugar beet plants exhibiting a biennial genotype.

The cultivated sugar beet (*Beta vulgaris* ssp. *vulgaris* L.) is a biennial plant which forms a storage root and a leaf rosette in the first year. Shoot elongation (bolting) and flower formation starts after a period of low temperature. In contrast, many wild beets of the genus *B. vulgaris* ssp. *maritima* show an annual growing habit due to the presence of the bolting gene B at the B locus, which was mapped to the central region of chromosome II. The BOLTING gene (B gene) is responsible for the determination of the annual habit in sugar beet. Annuality in the *Beta* species is considered a monogenic and dominant trait. Plants carrying the dominant B allele are able to switch from juvenile to reproductive stages in a vernalization-independent manner, contrary to biennial plants carrying the b allele that obligatory require vernalization for bolting and subsequent flowering to occur. The dominant allele of locus B is abundant in wild beets and causes bolting under long days without the cold requirement usually essential for biennial cultivars (Abe et al., 1997) carrying the recessive allele.

Bolting (stem elongation) is the first step clearly visible in the transition from vegetative to reproductive growth.

Traditionally, the biennial cultivated sugar beet is grown in spring and harvested in autumn. However, an extension of the growing season by sowing in autumn and cultivation over winter is expected to increase yield substantially and would allow to extend the sugar beet processing campaign addressing one demand of the sugar industry. However, cultivation of present sugar beet in central Europe over winter (i.e., as winter crop) is currently not possible because vernalization (inducted by the exposure to the cold temperatures during winter) would result in bolting and yield loss. It is thus highly desirable to develop non-bolting winter beet in which the vernalization response is modified to confer resistance or significant delay of bolting after cold-induction. Since the B gene plays a key role in the vernalization response in sugar beet, it represents a promising candidate for engineering bolting resistance by modulating the vernalization response.

Further, in cultivated sugar beet, bolting is an undesirable phenomenon, as it results in a drastic reduction of yield and gives rise to problems during harvesting and sugar extraction. Commercial seed productions for sugar beet are often done in regions, where annual weed beets are growing, which can cause pollen contamination in the seed productions, resulting in annuals in the commercial seed. This is not acceptable to the customers. To identify contaminations with annuals, commercial seed lots are grown in regions where no wild annual beets are growing directly after harvesting the seed. The plants are not vernalized and contaminations are identified by the presence of bolters. Replacing this test with a marker-based screening assay would be highly desirable, as results could be obtained earlier, which would lead to cost savings in seed processing.

A marker-based approach could also be advantageously used in sugar beet breeding, e.g., to speed up the breeding process, or to introduce new variation from wild sea beets. Owing to the incomplete penetration of the B allele and its environmental dependence, closely linked molecular markers are also needed to screen its presence in breeding lines. For all these cases, it is important to have a marker tightly linked to the B gene to be able to identify annuals or biennials accurately.

For the foregoing reasons, there is a need for transgenic means to modulate the vernalization response of sugar beet and also for marker-assisted means to discriminate between the annual and biennial alleles of the B gene in seed production and in sugar beet breeding.

The present invention now provides such transgenic means as well as marker-assisted means addressing the above needs.

SUMMARY OF THE INVENTION

The present invention relates to nucleic acid sequences, which have a sequence identity of at least 70% to a nucleic acid sequence selected from the group of nucleic acid sequences as set forth in any one of SEQ ID NOs: 1, 4, 5, 6, 7, 8, 9, 10, 53 or 54, to nucleic acid sequences which comprise at least 15 consecutive nucleotides of a nucleic acid sequence selected from the group of nucleic acid sequences as set forth in any one of SEQ ID NOs: 1, 4, 5, 6, 7, 8, 9, 10, 53, or 54, to said one; or to nucleic acid sequences which hybridize under stringent conditions or to a nucleic acid sequence selected from the group of nucleic acid sequences as set forth in any one of SEQ ID NOs: 1, 4, 5, 6, 7, 8, 9, 10, 53 or 54.

In a preferred embodiment the nucleic acid sequence of the present invention described hereinbefore is an isolated nucleic acid. With regard to the homology all individual numerical values, which fall into the range starting with at least 70% as mentioned herein before, i.e., 71%, 72%, 73%, 74%, 75%, . . . , 80%, 81%, 82%, 83%, 84%, 85%, 86%, 87%, 88%, 89%, 90%, 91%, 92%, 93%, 94%, 95%, 96%, 97%, 98%, 99% should likewise be covered by the present invention. Preferably the length of the nucleic acid sequence of the present invention comprises at least 15, 20, 25, 30, 35, 40, 45, or at least 50 contiguous nucleotides of a nucleic acid sequence selected from the group of nucleic acid sequences as set forth in any one of SEQ ID NOs: 1, 4, 5, 6, 7, 8, 9, 10, 53, or 54. It is to be understood that the term "at least x nucleotides" encompasses nucleic acid molecules having any numerical value starting with x and above. For example, the term "at least 15 nucleotides" is intended to encompass nucleic acid molecules with 15, 16, 17, 18, 19, 20, and more nucleotides. In a further preferred embodiment, the nucleic acid sequence of the present invention described hereinbefore hybridizes under stringent conditions, more preferred under highly stringent conditions to a nucleic acid sequence selected from the group of nucleic acid sequences as set forth in any one of SEQ ID NOs: 1, 4, 5, 6, 7, 8, 9, 10, 53, or 54.

In a further embodiment of this aspect, the nucleic acid molecule comprises a nucleotide sequence selected from the group consisting of SEQ ID NOs: 1, 4, 5, 6, 7, 8, 9, 10, 53, or 54, and the complements thereof. In another preferred embodiment, the nucleic acid sequence of the present invention described hereinbefore comprises a nucleic acid sequence as depicted in SEQ ID NO: 8, wherein said sequence comprises one or more nucleic acid substitutions, deletions, or additions as shown in Tables 7-1 and 7-2, wherein the polymorphisms shown in Tables 7-1 and 7-2 are representing 18 annual and 2 biennial alleles of the sequence depicted in SEQ ID NO: 8, respectively. The Tables 7-1 and 7-2 are also shown as FIGS. 11 and 12.

According to another aspect, the present invention further provides polypeptides which are encoded by the nucleic acid sequences of the present invention described hereinbefore. In a preferred embodiment the polypeptide of the present invention described hereinbefore has an amino acid sequence selected from the group of amino acid sequences as depicted in SEQ ID NOs: 11 or 12.

The invention further relates to the use of the B gene, particularly the BvPRR7 gene, in a transgenic approach for producing plants exhibiting a non-bolting phenotype. In particular, the invention relates to chimeric constructs comprising an expression cassette comprising a nucleic acid sequence of the present invention as described above under the control of regulatory elements, particularly under the control of regulatory elements functional in plants.

In one embodiment of the invention, the chimeric construct as described hereinbefore may further contain a selection marker gene which allows discriminating between transformed and non-transformed plant material in a selection procedure.

In one embodiment, the chimeric construct of the invention comprises a negative selection marker, particularly a selection marker encoding a resistance to plant toxic compounds such as antibiotics or herbicides. In another embodiment, the chimeric construct of the invention comprises a positive selection marker, particularly a selection marker encoding an enzyme that provides the transformed plant with a selective advantage over the non-transformed plants, particularly a nutritional advantage such as, for example, a phosphomannose isomerase gene, or a xylose isomerase gene.

In a preferred embodiment the chimeric construct of the present invention is provided for transgenic downregulation of BvPRR7 gene expression, particularly through an antisense or an RNAi approach. In this context the term "downregulation" or "suppression" is meant to refer to any reduction of the expression level of the BvPPR7 gene compared to the expression of the gene in non-transformed plants under the same conditions. This includes "silencing" of a gene such that no expression of the gene can be detected. In another preferred embodiment the chimeric construct of the present invention for transgenic downregulation of BvPRR7 gene expression comprises a nucleic acid molecule encoding a dsRNA which is capable of targeting mRNAs produced by transcription of the DNA sequence encoding the B gene protein, preferably the BvPRR7 protein, for degradation. In another preferred embodiment, the chimeric construct of the present invention described hereinbefore comprises a nucleic acid molecule encoding said dsRNA, wherein the nucleic acid molecule has a length of at least 21 nucleotides and is substantially identical with at least a part of the coding sequence of the BvPRR7 gene. Said coding sequences of the BvPRR7 gene are preferably the nucleic acid sequences of the present invention described hereinbefore. More preferably said coding sequences of the BvPRR7 gene are the nucleic acid molecules having as sequence as set forth as SEQ ID NOs: 1, 4, 5, 6, 9, 10, 53, or 54 in the present invention. The "substantially identical" refers two nucleic acid molecules which are able to hybridize to each other under stringent conditions. Generally identify or homology between the dsRNA and the coding sequence of the BvPRR7 gene or parts thereof is not required over the whole length of the dsRNA. It is sufficient if stretches of at least 21 nucleotides have identity, but preferably nucleic acid sequences are selected encoding dsRNA having homology to the target RNA molecule over a stretch of more than 21 nucleotides. Preferably, the chimeric construct of the present invention described hereinbefore comprises a nucleic acid molecule encoding the dsRNA and having a length of more than 21 nucleotides, more preferred of more than 50, 100, 250, 500, 600, 750, 1000 or more nucleotides.

In a preferred embodiment the nucleic acid molecule encoding the dsRNA which is comprised in the chimeric construct of the present invention has the nucleotide sequence as depicted in SEQ ID NO: 1 under the control of a constitutive promoter, preferably the Ubi3 promoter from *Arabidopsis*. In another embodiment, the chimeric construct of the present invention further comprises the sequence of the second intron from the potato StLS1 gene (Eckes et al, 1986; Vancanneyt et al, 1990). In a preferred embodiment the chimeric construct of the present invention comprises an inverted repeat targeting BvPRR7 consisting of the nucleotide sequence as depicted in SEQ ID NO: 1 that was cloned between the Ubi3 promoter (Norris et al, 1993) and the Nos terminator in both the antisense and sense orientation, separated by the second intron of the StLS1 gene from potato.

In one embodiment of the invention, a transformation vector and/or an expression vector is provided, particularly a plant transformation vector and/or an expression vector, comprising the chimeric construct of the invention as described herein before. In a further embodiment the plant expression vector is an RNAi expression vector comprising the chimeric construct of the invention described hereinbefore. In a more preferred embodiment the RNAi expression vector comprises the chimeric construct of the present invention shown in FIG. 10.

In a further aspect of the present invention a plant cell is provided comprising a chimeric construct or a vector molecule (e.g., a transformation vector or an expression vector) according to the invention and as described herein before. In a preferred embodiment said plant cell comprising a chimeric construct or a vector molecule of the present invention is a plant cell of a sugar beet plant.

Further provided are transgenic plants, particularly sugar beet plants, having a phenotype of delayed bolting, or cells, tissues or seeds thereof, each comprising a plant cell of the present invention and/or a chimeric construct according to the present invention and/or a nucleic acid sequence of the present invention as described above, wherein said transgenic plant is expressing the dsRNA such that bolting is delayed, particularly suppressed, and the plant exhibits a phenotype of delayed bolting, preferably a non-bolting phenotype. "Delay of bolting" has to be understood as a modulation of the natural bolting reaction of sugar beet plants. During bolting the stem is elongated as a first step and during transition from vegetative to reproductive growth after vernalization of the plants (i.e., exposure to cold temperatures) and finally results in flower development. Delay of the bolting reaction is meant to refer to stem elongation which starts later compared to normal plants; those plants exhibit a phenotype of delayed bolting. The bolting reaction can be delayed by a few days (i.e., by 5, 6, 7, 8, 9, 10, 11, 12, 13 or 14 days) and up to several weeks (i.e., by 2, 3, 4 weeks) or several months (i.e., 1, 2, 3, 5, or 6 months). In a preferred embodiment the bolting response is completely suppressed; such plants do not start to bolt after vernalization and exhibit a non-bolting phenotype. In a further preferred embodiment, the present invention provides transgenic plants, particularly sugar beet plants, which are produced from the cells, tissues or seeds of the present invention and described above.

In another aspect, the present invention provides a method for producing hybrid seeds from which plants, particularly sugar beet plants, with a phenotype of modulated bolting can be grown. Such methods preferably: (a) providing a plant line, particularly a sugar beet line with a phenotype of modulated bolting, particularly a transgenic sugar beet plant of the present invention and as describe above as a first parent line, (b) providing a second plant line, particularly a sugar beet line having a different genotype as a second parent line; wherein one of the parent lines of step a) or step b) is a male sterile CMS line and wherein the other parent line is male fertile, and (c) allowing the plants of the male fertile parent line to pollinate the flowers of the second male sterile parent line, let the seed develop, and harvest the hybrid seed; wherein the harvested hybrid seeds are seeds of a hybrid plant, particularly a sugar beet hybrid plant, having a phenotype of delayed bolting. In a preferred embodiment both parent lines are sugar beet plant lines, wherein at least one of the sugar beet parent lines is a transgenic sugar beet line of the present invention. The at least one sugar beet parent line with a phenotype of modulated bolting can preferably also be a plant without any transgene, which is then obtained by other methods of genetic manipulation as described below. In an embodiment of this aspect the sugar beet parent line provided in step (a) is a male sterile CMS inbred sugar beet line comprising one or more of the a nucleic acid sequences of the present invention or fragments thereof, and the second sugar parent line provided in step (b) is a male fertile inbred sugar beet line. In another preferred embodiment the sugar beet parent line provided in step (a) is a male fertile sugar beet plant comprising one or more of the a nucleic acid sequences of the present invention or fragments thereof, and the second sugar parent line provided in step (b) is a male sterile CMS inbred sugar beet line.

A further aspect of the present invention relates to hybrid seed of a plant, particularly a sugar beet plant, exhibiting a phenotype of delayed bolting. In yet another aspect of the present invention the hybrid seed is produced by a method of the present invention and as described above. In a further preferred embodiment a hybrid plant, particularly a hybrid sugar beet plant, having a phenotype of delayed bolting is produced by growing the hybrid seed of the present invention described above. A further preferred embodiment of the present invention relates to plant parts selected from the group consisting of seeds, embryos, microspores, zygotes, protoplasts, cells, ovules, pollen, taproots, cotyledons, extracts or biological samples, which are derived from the transgenic sugar beet plant or seeds thereof of the present invention or derived from hybrid plants or seeds of the present invention as described above.

Another aspect of the present invention relates to the use of a nucleic acid sequence of the present invention or fragments thereof for the transformation of plant cells, particularly of cells of sugar beet plants. The purpose of transforming plant cells, particularly of cells of a sugar beet plant, with a nucleic acid sequence of the present invention or fragments thereof is to modulate the bolting behaviour of the plant as described above. Another embodiment of this aspect relates to a method of transforming plant cells, particularly of cells of a sugar beet plant, wherein the method comprises the use of a nucleic acid sequence of the present invention or of a chimeric construct of the present invention or of vector of the present invention and as described above.

In another aspect, the present invention provides the use of the transgenic plant of the present invention, of the hybrid plant of the present invention, or of the plant parts of the present invention and as described above in a method selected from the group comprising of methods of sugar production, methods of aerobic fermentation and methods of anaerobic fermentation. Preferably, the transgenic plant of the present invention, of the hybrid plant of the present invention, or of the plant parts of the present invention and as described above is used in a method of producing sugar. Another aspect relates to a method for producing sugar wherein the sugar beet plant, or cells or tissues thereof of the present invention and as described above is processed to produce sugar. The present invention further provides sugar produced from the sugar beet plant, or cells or tissues thereof of the present invention and as described above is processed.

In a further aspect the present invention relates to polynucleotide marker developed based on a nucleic acid sequence which is obtainable from a genomic DNA region that shows perfect co-segregation with the bolting gene (B gene) associated phenotype in sugar beet and wherein the marker allows to discriminate between the annual and biennial genotype or between different haplotypes within a plant grouping of sugar beet plants exhibiting a biennial or annual genotype. In a preferred embodiment the polynucleotide markers of the present invention have a nucleic acid sequence obtainable from one or more of the nucleic acid sequences of the present invention and as described above. In one embodiment the polynucleotide markers of the present invention further comprise one or more polymorphisms, particularly a polymorphism that is based on an SNP, an SSR, a deletion or an insertion of at least one nucleotide, but especially a polymorphism based on an SNP, which polymorphism is diagnostic for the B allele at the B locus. Such polynucleotide markers are preferably capable of detecting at least one of the various SNPs present in the different alleles of the genomic sequence set forth as SEQ ID NO: 8 herein and shown in Tables 7-1 (further depicted in FIG. 11) and 7-2 (further depicted in FIG. 12), wherein said polynucleotide marker is capable of differentiating between different alleles, particularly between annual and biennial sugar beet lines. In a preferred embodiment the polynucleotide marker of the present invention are capable of detecting at least one SNP selected from the group comprising SNPs at positions #224, #351, #615, #897, #1082, #1841, #1915, #2334, #11592, #12316, #12490, or #12544 of the sequence set forth as SEQ ID NO: 8 and as shown in Tables 7-1 (further depicted in FIG. 11) and 7-2 (further depicted in FIG. 12). A further aspect of the present invention relates to a set of polynucleotide markers comprising a plurality of the polynucleotide markers of the present invention and described above. In this context, the term "plurality" refers to a set of more than one polynucleotide marker, which preferably consists of two, three or more markers.

Another aspect of the present invention relates to a pair of primers consisting of a forward primer and a reverse primer which primers are capable of annealing to a nucleotide sequence within a genomic region of the sugar beet genome DNA that shows perfect co-segregation with the bolting gene (B gene). In a preferred embodiment the pair of primers of the present invention anneals to a nucleic acid sequence of the present invention and as describe above and amplifies a polynucleotide, preferably the polynucleotide marker of the present invention, or of an informative part thereof, wherein said polynucleotide comprises one or more polymorphisms, particularly one or more polymorphisms which is/are diagnostic for the B allele at the B locus and allows to discriminate between the annual and biennial genotype. In a preferred embodiment the pair of primers of the present invention is selected from the group consisting of: (a) a pair of primers which anneals to a nucleotide sequence within the 3rd intron of BvPPR7 as depicted in SEQ ID NO: 6, which amplifies an informative fragment from said region comprising a polymorphism, particularly a polymorphism comprising a C/T SNP at position #87 and/or a C/T SNP at position #160 and/or an A/G SNP at position #406; or (b) a pair of primers which anneals to the nucleic acid sequence set forth as SEQ ID NO: 8 and amplifies an informative fragment from said sequence comprising a polymorphism selected from the polymorphisms based on a SNP present in the different alleles of said sequence as shown in Tables 7-1 (further depicted in FIG. 11) and 7-2 (further depicted in FIG. 12). In a further preferred embodiment, the pair of primers of the present invention comprises: (a) forward primer PRR7(T6)-F as depicted in SEQ ID NO: 49 and reverse primer PRR7(T6)-R as depicted in SEQ ID NO: 50 for amplifying a fragment comprising SNP #2334; or (b) forward primer PRR7(T1)-F as depicted in SEQ ID NO: 13 and reverse primer PRR7(T1)-R as depicted in SEQ ID NO: 14 for amplifying a fragment comprising SNP #160; or (c) forward primer 1r22(T1)-F as depicted in SEQ ID NO: 55 and reverse primer 1r22(T1)-R as depicted in SEQ ID NO: 56 for amplifying a fragment and probe molecule 1r22(T1)-VIC as depicted in SEQ ID NO: 57 as a first probe molecule labelled with VIC as first fluorescent dye and probe molecule 1r22(T1)-FAM as depicted in SEQ ID NO: 58 as a second probe molecule labelled with FAM as second fluorescent dye.

In one embodiment, the invention relates to one or a plurality of probe molecules and/or to one or a plurality of primers, particularly one or a plurality of primer pairs, but especially one or a plurality of primer pairs consisting of a forward primer and a reverse primer, which primers are capable of annealing to a nucleic acid sequence which is obtainable from a genomic DNA region that shows perfect co-segregation with the bolting gene (B gene) associated phenotype in sugar beet and wherein the marker allows to discriminate between the annual and biennial genotype or between different haplotypes within plant groupings of sugar beet plants exhibiting a biennial or annual genotype.

In one embodiment, the invention relates to a set of probe polynucleotides comprising at least two separate probe molecules that are complementary to a sub-region within an informative polynucleotide fragment according to the invention and as described herein before comprising a polymorphic site and amplify partially overlapping fragments which differ only by one or two base mismatches in the area of overlap, wherein a first probe, particularly a probe labelled with a first fluorescent dye, more particularly with a first fluorescent dye and a quencher represents one allele and a second probe, particularly a probe labelled with a second fluorescent dye, which is not identical with the first dye, more particularly with a second fluorescent dye and a quencher, represents the other allele.

The above polynucleotide markers of the present invention, a set of polynucleotide markers of the present invention or a pair of primers of the present invention can be used in an allelic discrimination assay for identifying the absence or presence of an allele associated with annuality in a sugar beet plant.

In another aspect of the present invention an allelic discrimination assay for identifying the absence or presence of an allele associated with annuality in a sugar beet plant is provided, which allows to discriminate between annual and biennial plants. In a preferred embodiment the polynucleotide marker of the present invention, a set of polynucleotide markers of the present invention, or a pair of primers of the present invention is used in this assay.

In a further preferred embodiment the allelic discrimination assay of the present invention comprises the steps of: (a) obtaining a sample of genomic DNA from a sugar beet plant to be analyzed, (b) amplifying a fragment from said sample or genomic DNA using a pair of primers of the present invention, and (c) comparing the amplified fragment with an allelic sequence known to be associated with the biennial phenotype but not with the annual phenotype, respectively. In this assay the sequence of amplified fragment of step (c) is compared with sequences of alleles known to be associated with the biennial phenotype. If the sequence is different from the sequences of the biennial alleles, this is indicative of the presence of annual allele (i.e., an annual plant). In another preferred embodiment the amplified fragment obtained in step c) of the allelic discrimination assay of the present invention is probed with a first fluorescence-labelled probe molecule comprising a sequence specific for the annual allele. If the dye fluorescence of the first probe increases during the reaction this is indicative of the presence of the annual allele.

In a preferred embodiment, the assay of the present invention employs either (a) forward primer PRR7(T6)-F as depicted in SEQ ID NO: 49 and reverse primer PRR7(T6)-R as depicted in SEQ ID NO: 50 for amplifying a fragment comprising SNP #2334 and probe molecule PRR7(T6)-VIC as depicted in SEQ ID NO: 51 as a first probe molecule labelled with VIC as first fluorescent dye and probe molecule PRR7(T6)-FAM as depicted in SEQ ID NO: 52 as a second probe molecule labelled with FAM as second fluorescent dye; or (b) forward primer PRR7(T1)-F as depicted in SEQ ID NO: 13 and reverse primer PRR7(T1)-R as depicted in SEQ ID NO: 14 for amplifying a fragment comprising SNP #160 and probe molecule PRR7(T1)-VIC as depicted in SEQ ID NO: 15 as a first probe molecule labelled with VIC as first fluorescent dye and probe molecule PRR7(T1)-FAM as depicted in SEQ ID NO: 16 as a second probe molecule labelled with FAM as second fluorescent dye; or (c) forward primer 1r22(T1)-F as depicted in SEQ ID NO: 55 and reverse primer 1r22(T1)-R as depicted in SEQ ID NO: 56 for amplifying a fragment and probe molecule 1r22(T1)-VIC as depicted in SEQ ID NO: 57 as a first probe molecule labelled with VIC as first fluorescent dye and probe molecule 1r22(T1)-FAM as depicted in SEQ ID NO: 58 as a second probe molecule labelled with FAM as second fluorescent dye.

In one embodiment, the present invention relates to a method of identifying annual contaminations in commercial seed using a marker-based allelic discrimination assay according to the invention and as described herein before.

BRIEF DESCRIPTION OF THE FIGURES AND SEQUENCES

Figures

FIG. 1: Amino acid sequence comparison of the REC domains between different species and the putative REC domain of sugar beet EST CV301305. Identical amino acids are in black; conserved in grey; weakly similar in light grey and non-similar in white. Bb, *Bordetella bronchiseptica*; Bs, *Bacillus subtilis*; Bv, *Beta vulgaris*; Ec, *Escherichia coli*; Kp, *Klebsiella pneumoniae*; Pa, *Pseudomonas aeruginosa*; Rc, *Rhodobacter capsulatus*; Sc, *Streptomyces coelicolor*; Sf, *Shigella flexneri*; St, *Salmonella typhimurium*.

FIG. 2: Amino acid sequence comparison of the *Arabidopsis* PRR7 protein and the predicted partial protein from sugar beet EST CV301305. Identical amino acids are in black; similar in grey and non-similar in white.

FIG. 3: Sequence alignment between the genomic and mRNA sequences of the *Arabidopsis* PRR7 gene and sugar beet EST CV301305. Conserved nucleotides between *Arabidopsis* and *Beta vulgaris* L. are in grey. Introns are represented by strings of dashes.

FIG. 4: Genetic map of sugar beet chromosome II. Marker names are given at the right of the chromosome, at the left the cumulative genetic distance is indicated.

Figure 5:
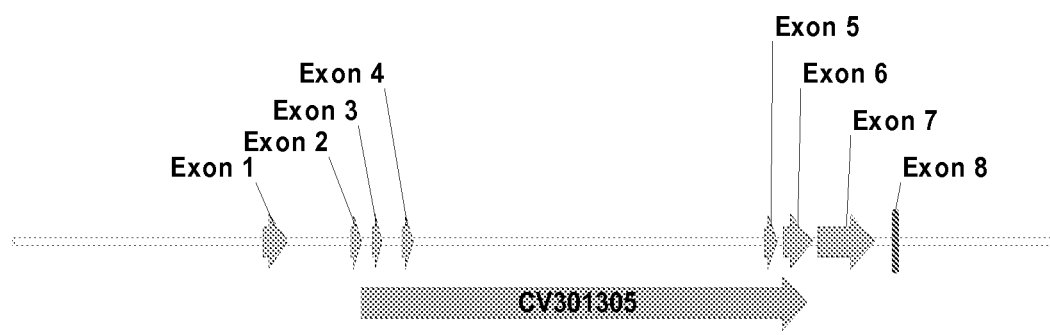

FIG. 5: Schematic representation of the gene structure of the BvPRR7 gene showing putative exons and introns. The region covered by EST CV301305 is shown by the block arrow.

FIG. 6: Amino acid sequence comparison of the *Arabidopsis* PRR gene family members and the BvPRR7 protein. Identical amino acids are in black; conserved in grey; weakly similar in light grey and non-similar in white.

Figure 7:
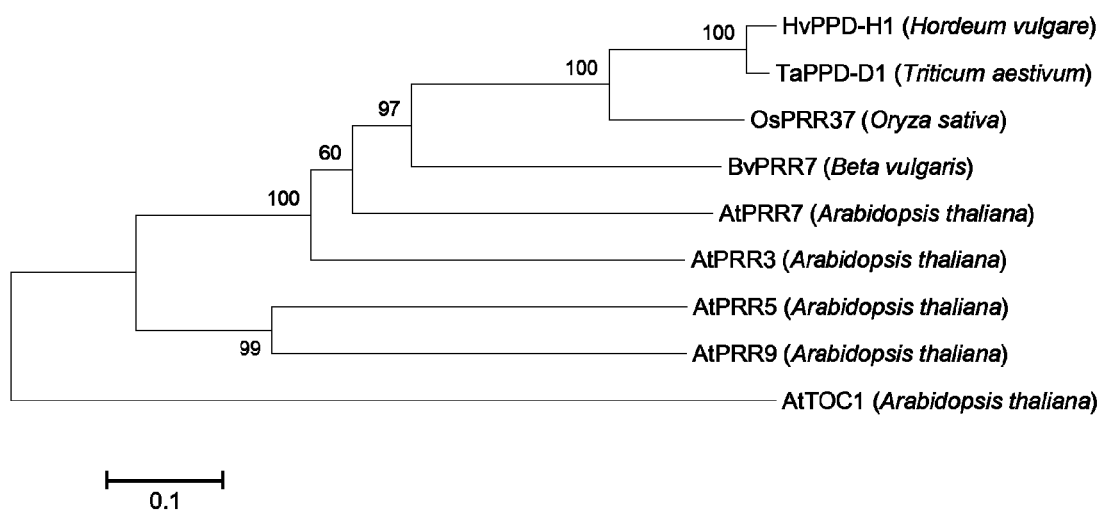

FIG. 7: Phylogenetic relationship between BvPRR7 and related proteins from other flowering plants based on an phylogenetic analysis of multiple members in the PRR gene family from several plant species including the PRR7 homolog from sugar beet, *Arabidopsis thaliana* (TOC1, NP_200946; PRR3, NP_568919; PRR5, NP_568446; PRR7, NP_568107; and PRR9, NP_566085), *Oryza sativa* (PRR37, Q0D3B6), *Hordeum vulgare* (PPD-H1, AAY17586) and *Triticum aestivum* (PPD-D1, ABL09477) by. using the Neighbor-Joining method (Saitou and Nei, 1987). The bootstrap consensus tree inferred from 1000 replicates is taken to represent the evolutionary history of the taxa analyzed (Felsenstein, 1985). Branches corresponding to partitions reproduced in less than 50% bootstrap replicates are collapsed. The percentage of replicate trees in which the associated taxa clustered together in the bootstrap test (1000 replicates) are shown next to the branches. The tree is drawn to scale, with branch lengths in the same units as those of the evolutionary distances used to infer the phylogenetic tree. The evolutionary distances were computed using the Poisson correction method (Zuckerkandl and Pauling, 1965) and are in the units of the number of amino acid substitutions per site. All positions containing gaps and missing data were eliminated from the dataset (Complete deletion option). There were a total of 352 positions in the final dataset.

Figure 8:
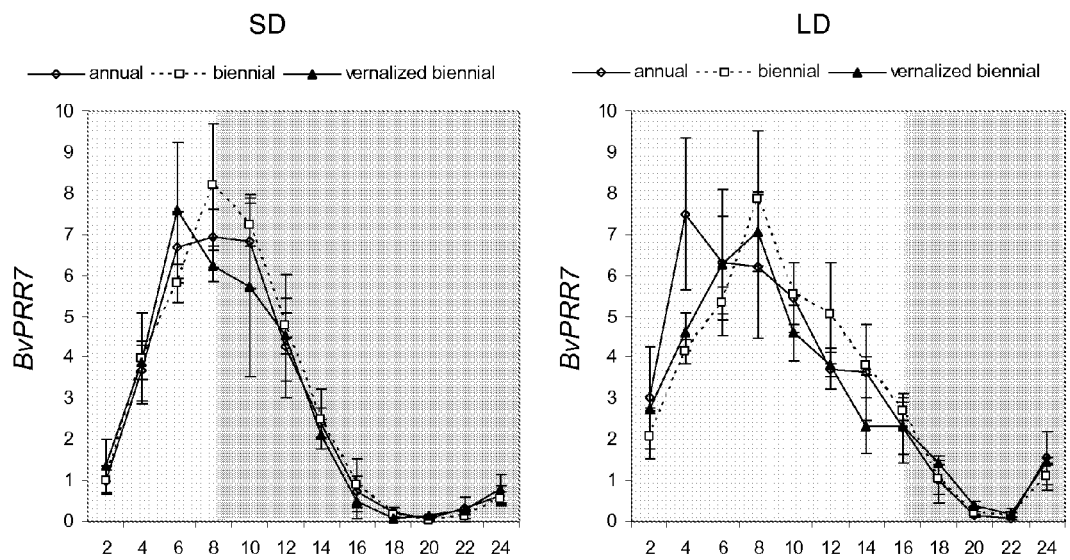

FIG. 8: Diurnal expression patterns of BvPRR7 in annual and biennial sugar beet plants. Leaf tissues were harvested every 2 hours across a period of 24 hours. Wight and dark grey backgrounds represent light respectively dark periods. Data shown are mean values from three independent biological samples. Values are expressed as relative expression levels normalized against the BvICDH reference gene by geometric averaging analysis (Vandesompele et al., 2002). Error bars ±SD. ZT, zeitgeber time.

Figure 9:
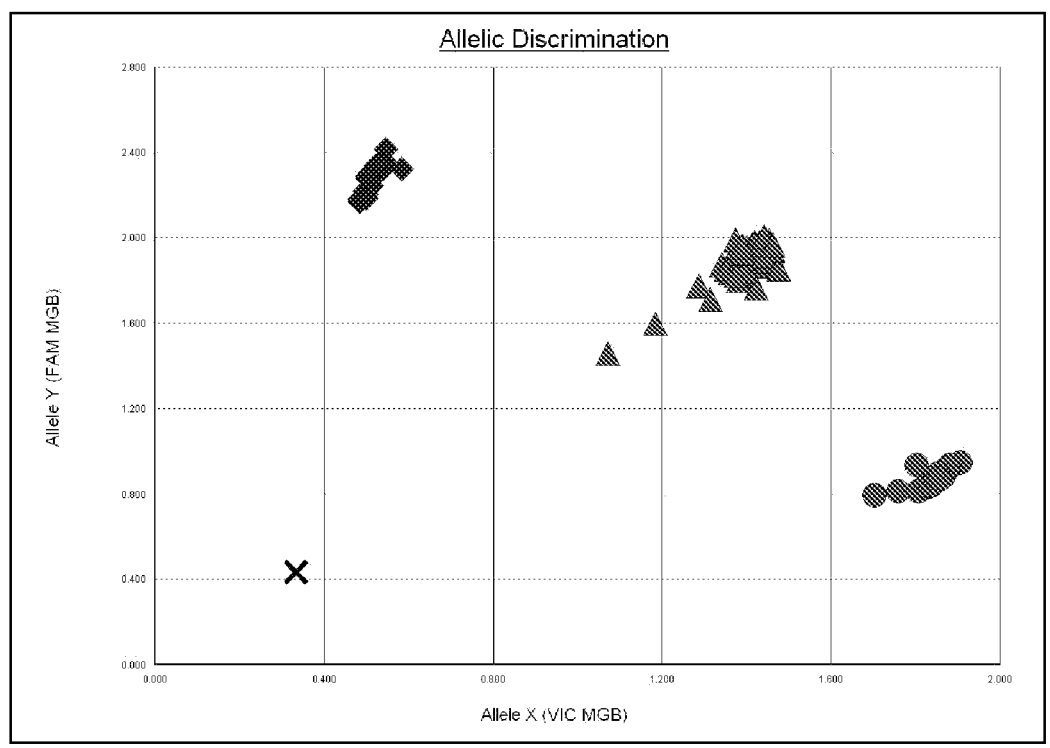

FIG. 9: EndPoint reading of an allelic discrimination analysis between a set of annual and biennial individual plants. Values on the Y and X axis represent fluorescence levels of the FAM dye and the VIC dye, respectively. Substantial increase in VIC dye fluorescence (X axis) only indicates homozygosity for the biennial allele (referred to as allele X in this Figure). Substantial increase in FAM dye fluorescence only indicates homozygosity for the annual allele ((referred to as allele Y in this Figure). Substantial increase in both fluorescent signals indicates heterozygosity, i.e. annual plant with heterozygosity for the B locus.

Figure 10:
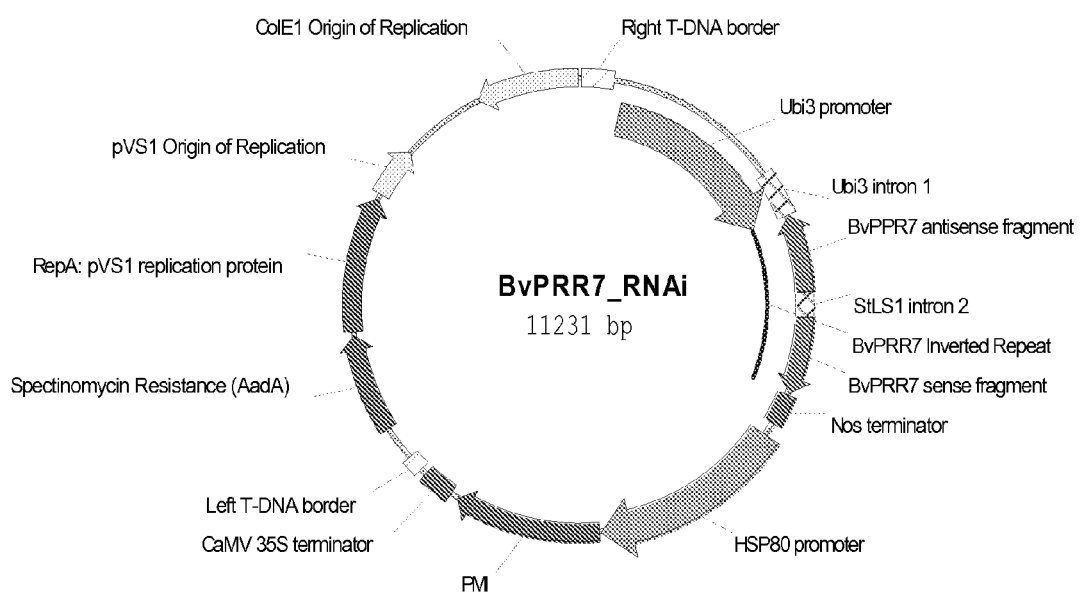

FIG. 10: Plasmid map of the binary vector used for the transgenic suppression of BvPRR7 by means of RNAi. The inverted repeat for BvPRR7 consists of a 0.6 Kb cDNA fragment that was cloned between the Ubi3 promoter (Norris et al, 1993) and Nos terminator in both the antisense and sense orientation, separated by the second intron of the StLS1 gene from potato (Eckes et al, 1986; Vancanneyt et al, 1990). The selectable marker consists of the PMI gene under the control of the HSP80 promoter (Brunke and Wilson, 1993).

FIG. 11: Table showing polymorphisms identified in the promoter region of the BvPRR7 when comparing 18 annual and 2 biennial alleles of BvPRR7; SNP positions indicated in the table are numbered in accordance to SEQ ID NO: 8.

Figure 12:
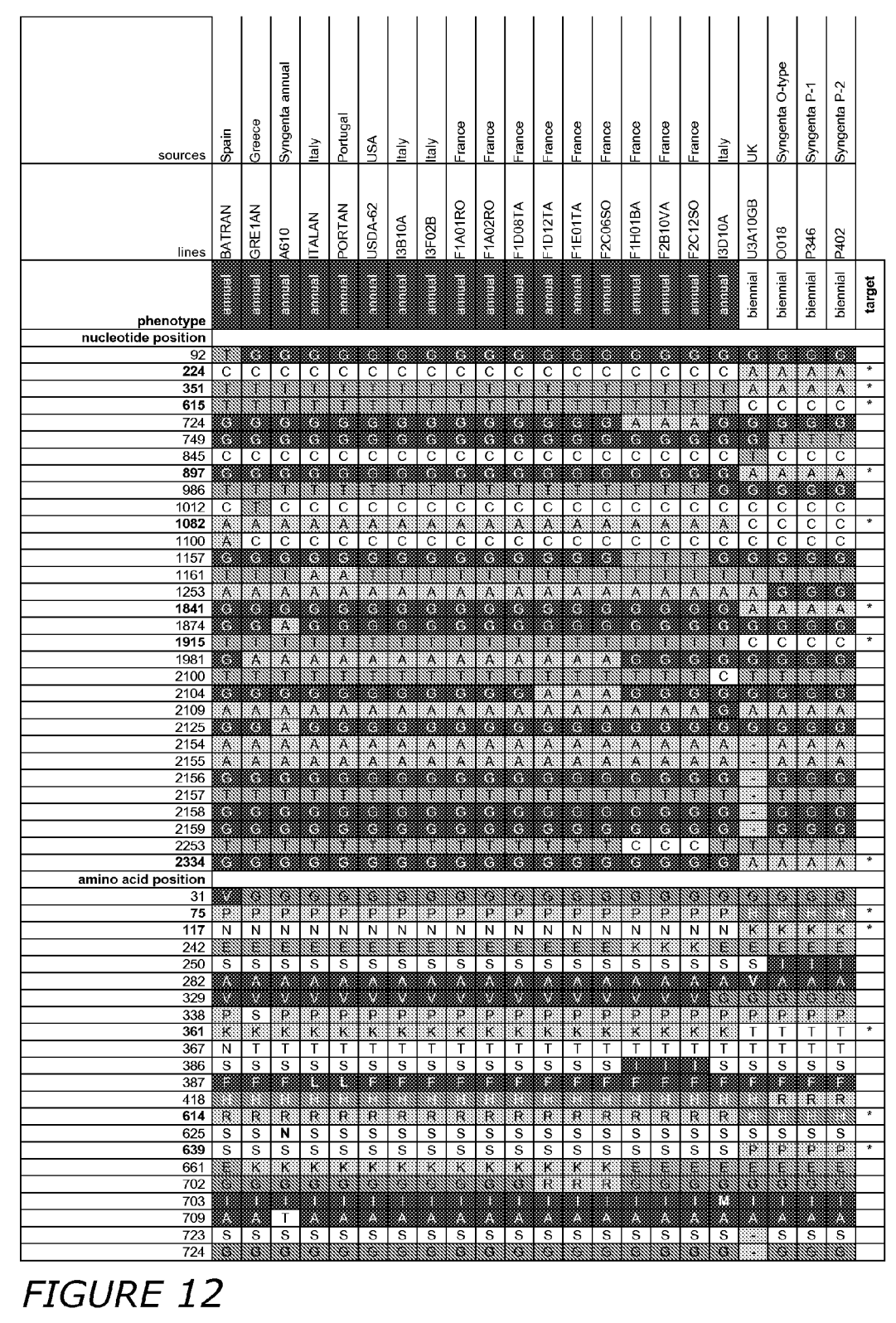

FIG. 12: Table showing polymorphisms identified in the coding region of the BvPRR7 when comparing 18 annual and 2 biennial alleles of BvPRR7; SNP positions indicated in the table are numbered in accordance to SEQ ID NO: 8.

SEQUENCES

SEQ ID NO: 1 depicts the nucleotide sequence of the sugar beet EST CV301305

SEQ ID NO: 2 depicts the nucleotide sequence of the forward primer PRR7-F

SEQ ID NO: 3 depicts the nucleotide sequence of the reverse primer PRR7-R

SEQ ID NO: 4 depicts the nucleotide sequence of intron 3 of allelic variant 2 of BvPRR7 (haplotype #2)

SEQ ID NO: 5 depicts the nucleotide sequence of intron 3 of allelic variant 1 of BvPRR7 (haplotype #1)

SEQ ID NO: 6 depicts the nucleotide sequence of intron 3 of BvPRR7 and its allelic variability for mapping SEQ ID NO: 7 depicts the genomic nucleotide sequence of the biennial allele of BvPRR7

SEQ ID NO: 8 depicts the nucleotide sequence of genomic nucleotide sequence of BvPRR7 including the promoter and the terminator regions.

SEQ ID NO: 9 depicts the nucleotide sequence of the coding region of the biennial allele of BvPRR7

SEQ ID NO: 10 depicts the nucleotide sequence of the coding region of the annual allele of BvPRR7

SEQ ID NO: 11 depicts the putative amino acid sequence of the biennial allele of BvPRR7

SEQ ID NO: 12 depicts the putative amino acid sequence of the annual allele of BvPRR7

SEQ ID NO: 13 depicts the nucleotide sequence of primer PRR7(T1)-F

SEQ ID NO: 14 depicts the nucleotide sequence of primer PRR7(T1)-R

SEQ ID NO: 15 depicts the nucleotide sequence of probe PRR7(T1)-VIC

SEQ ID NO: 16 depicts the nucleotide sequence of probe PRR7(T1)-FAM

SEQ ID NO: 17 depicts the nucleotide sequence of primer GJ131(T1)-F

SEQ ID NO: 18 depicts the nucleotide sequence of primer GJ131(T1)-R

SEQ ID NO: 19 depicts the nucleotide sequence of probe GJ131(T1)-VIC

SEQ ID NO: 20 depicts the nucleotide sequence of probe GJ131(T1)-FAM

SEQ ID NO: 21 depicts the nucleotide sequence of primer ED031700(T1)-F

SEQ ID NO: 22 depicts the nucleotide sequence of primer ED031700(T1)-R

SEQ ID NO: 23 depicts the nucleotide sequence of probe ED031700(T1)-VIC

SEQ ID NO: 24 depicts the nucleotide sequence of probe ED031700(T1)-FAM

SEQ ID NO: 25 depicts the nucleotide sequence of primer 9_27(T2)-F

SEQ ID NO: 26 depicts the nucleotide sequence of primer 9_27(T2)-R

SEQ ID NO: 27 depicts the nucleotide sequence of probe 9_27(T2)-VIC

SEQ ID NO: 28 depicts the nucleotide sequence of probe 9_27(T2)-FAM

SEQ ID NO: 29 depicts the nucleotide sequence of primer GJ01(T1)-F

SEQ ID NO: 30 depicts the nucleotide sequence of primer GJ01(T1)-R
SEQ ID NO: 31 depicts the nucleotide sequence of probe GJ01(T1)-VIC
SEQ ID NO: 32 depicts the nucleotide sequence of probe GJ01(T1)-FAM
SEQ ID NO: 33 depicts the nucleotide sequence of primer SELA3977
SEQ ID NO: 34 depicts the nucleotide sequence of primer SELA3988
SEQ ID NO: 35 depicts the nucleotide sequence of primer SELA4442
SEQ ID NO: 36 depicts the nucleotide sequence of primer SELA3809
SEQ ID NO: 37 depicts the nucleotide sequence of primer SELA3810
SEQ ID NO: 38 depicts the nucleotide sequence of primer SELA3807
SEQ ID NO: 39 depicts the nucleotide sequence of primer SELA3766
SEQ ID NO: 40 depicts the nucleotide sequence of primer SELA3769
SEQ ID NO: 41 depicts the nucleotide sequence of primer SELA3857
SEQ ID NO: 42 depicts the nucleotide sequence of primer SELA3860
SEQ ID NO: 43 depicts the nucleotide sequence of primer SELA3861
SEQ ID NO: 44 depicts the nucleotide sequence of primer SELA3864
SEQ ID NO: 45 depicts the nucleotide sequence of forward primer BvPRR7 used for gene expression analysis
SEQ ID NO: 46 depicts the nucleotide sequence of reverse primer BvPRR7 used for gene expression analysis
SEQ ID NO: 47 depicts the nucleotide sequence of forward primer BvICDH used for gene expression analysis
SEQ ID NO: 48 depicts the nucleotide sequence of reverse primer BvICDH used for gene expression analysis
SEQ ID NO: 49 depicts the nucleotide sequence of primer PRR7(T6)-F
SEQ ID NO: 50 depicts the nucleotide sequence of primer PRR7(T6)-R
SEQ ID NO: 51 depicts the nucleotide sequence of probe PRR7(T6)-VIC
SEQ ID NO: 52 depicts the nucleotide sequence of probe PRR7(T6)-FAM
SEQ ID NO: 53 depicts the nucleotide sequence of the coding region of the annual PRR7 allele downstream of approximately 1,3 kb of its promoter region
SEQ ID NO: 54 depicts the nucleotide sequence of the coding region of the annual allele of BvPRR7 including approximately 1,3 kb of its promoter region and approximately 0.7 kb of its terminator region
SEQ ID NO: 55 depicts the nucleotide sequence of primer 1r22(T1)-F
SEQ ID NO: 56 depicts the nucleotide sequence of primer 1r22(T1)-R
SEQ ID NO: 57 depicts the nucleotide sequence of probe 1r22(T1)-VIC
SEQ ID NO: 58 depicts the nucleotide sequence of probe 1r22(T1)-FAM Definitions The technical terms and expressions used within the scope of this application are generally to be given the meaning commonly applied to them in the pertinent art of plant molecular biology if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

"Sugar beet" refers to all species and subspecies within the genus *Beta* as well as all kinds of cultivated beets of *Beta vulgaris*. Cultivated beets have been separated into four groups: leaf beet, garden beet, fodder beet and sugar beet. "Sugar beet" refers also to all cultivated beets including those grown for other purposes than the production of sugar, such as ethanol, plastics or industrial products. In particular, "Sugar beet" refers to fodder beet and sugar beet, but especially to sugar beet. This term also includes sugar beet plants adapted for growth in tropical or subtropical regions.

An "annual sugar beet line" refers to a sugar beet plant containing the dominant allele B at the B locus in a heterozygous or homozygous state.

A "biennial sugar beet line" refers to a sugar beet plant containing the recessive allele b at the B locus in a homozygous state "Bolting" refers to the transition from the vegetative rosette stage to the inflorescence or reproductive growth stage.

"Delayed bolting" or "delay of bolting" as used herein has to be understood as a modulation of the natural bolting reaction of sugar beet plants. In plants with delayed bolting stem elongation as the first visible step of bolting starts later than in normal plants. The bolting reaction can be delayed by just a few days (i.e., by, for example, 5, 6, 7, 8, 9, 10, 11, 12, 13 or 14 days) and up to several weeks (i.e., by 2, 3, 4 weeks) or several months (i.e., 1, 2, 3, 5, or 6 months). Delay of bolting can also result in a complete suppression of the bolting response; such plants do not bolt after vernalization and exhibit a non-bolting phenotype.

"B gene" as used herein refers to a gene that is responsible for the determination of the annual habit (early bolting) in sugar beet. Plants carrying the dominant allele B are able to switch from juvenile to reproductive stages in a vernalization-independent manner, i.e. make shoot elongation followed by flowering without prior exposure to cold temperatures.

"Vernalization" refers to the process by which floral induction in some plants is promoted by exposing the plants to chilling for certain duration.

An "allele" is understood within the scope of the invention to refer to alternative forms of various genetic units associated with different forms of a gene or of any kind of identifiable genetic element, which are alternative in inheritance because they are situated at the same locus in homologous chromosomes. In a diploid cell or organism, the two alleles of a given gene (or marker) typically occupy corresponding loci on a pair of homologous chromosomes.

As used herein, the term "haplotype" refers to the set of alleles an individual inherited from one parent. A diploid individual thus has two haplotypes. The term "haplotype" can be used in a more limited sense to refer to physically linked and/or unlinked genetic markers (e.g., sequence polymorphisms) associated with a phenotypic trait (such as the annual or biennial bolting behavior of sugar beet plants in the context of the present invention). With regard to the B gene the haplotype of this gene also directly confers a phenotype. The annual growing habit of sugar beet, for example, is caused by the presence of the dominant allele of locus B at chromosome II.

"Locus" is understood within the scope of the invention to refer to a region on a chromosome, which comprises a gene or any other genetic element or factor contributing to a trait.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles that contribute to variability in expression of phenotypic traits on a chromosome. The phrase "genetic marker" can also refer to a polynucleotide sequence complementary to a genomic sequence, such as a sequence of a nucleic acid used as probes.

A genetic marker can be physically located in a position on a chromosome that is within or outside of to the genetic locus with which it is associated (i.e., is intragenic or extragenic, respectively). Stated another way, whereas genetic markers are typically employed when the location on a chromosome of the gene that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the phrase "phenotypic trait" refers to the appearance or other detectable characteristic of an individual, resulting from the interaction of its genome with the environment.

"Phenotype" is understood within the scope of the invention to refer to a distinguishable characteristic(s) of a genetically controlled trait.

The terms "closely linked" or "genetically closely linked" as used herein in the context of a genomic region of the sugar beet genome linked to the B gene are understood to refer to a close association of the genomic region and the B gene in inheritance due to location of both in proximity on the same chromosome, measured by percent recombination between loci (centi-Morgan, cM). As used herein, the term "linkage", and grammatical variants thereof, refers to the tendency of alleles at different loci on the same chromosome to segregate together (co-segregate) more often than would be expected by chance if their transmission were independent, As used herein, the phrase "informative fragment" refers to a polynucleotide fragment with an information content that is a retrievable and can assist in the determination and/or characterization of a genetic locus of interest. This information content may be represented by a polymorphism which is associated with said locus of interest such as, for example, a single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples and may be used for the development of a genetic marker. The information content of such an "informative fragment" may also be represented by a specific sequence that can be detected by a corresponding probe molecule. Such informative fragments could be a primer or a marker or a part thereof. Such fragments have a length of at least 10 nucleotides, preferably of at least 15, 20, 25, 30, 50, or 100 nucleotides.

"Marker-based selection" is understood within the scope of the invention to refer to the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"PCR (Polymerase chain reaction)" is understood within the scope of the invention to refer to a method of producing relatively large amounts of specific regions of DNA, thereby making possible various analyses that are based on those regions.

"PCR primer" or "primer" is understood within the scope of the invention to refer to short fragments of isolated single-stranded DNA used in the PCR amplification of specific regions of DNA. They are annealed to a complimentary target DNA strand by nucleic acid hybridization to form a hybrid between the primer and the target DNA strand, and then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods. Primers are generally between 10 and 15 nucleotides or more in length. Primers can also be at least 20 nucleotides or more in length, or at least 25 nucleotides or more, or at least 30 nucleotides or more in length. Such primers hybridize specifically to a target sequence under high stringency hybridization conditions. Primers according to the present invention may have complete sequence complementarity with the target sequence. It is to be understood that the length of the primers of the present invention can be any numerical value between the values specified herein. Thus, primers being generally between 10 and 15 nucleotides or more in length encompass primer having a length of 10, 11, 12, 13, 14, or 15 nucleotides, whereas the expression "at least 20 nucleotides" further includes primer having a length of 16, 17, 18, 19, or nucleotides. The same applies to the expressions "at least 25 nucleotides or more" and "at least 30 nucleotides or more in length".

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

A "probe" is an isolated nucleic acid to which is attached a conventional detectable label or reporter molecule, such as a radioactive isotope, ligand, chemiluminescent agent, fluorescent label or enzyme. Such a probe is complimentary to a strand of a target nucleic acid. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length. Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the present invention may have complete sequence complementarity with the target sequence, although probes differing from the target sequence and which retain the ability to hybridize to target sequences may be designed by conventional methods. It is to be understood that the length of the primers and probes of the present invention can be any numerical value between the values specified herein. Thus, primers and probes being generally between 10 and 15 nucleotides or more in length encompass primer and probes having a length of 10, 11, 12, 13, 14, or 15 nucleotides, whereas the expression "at least 20 nucleotides" further includes primer and probes having a length of 16, 17, 18, 19, or nucleotides. The same applies to the expressions "at least 25 nucleotides or more" and "at least 30 nucleotides or more in length".

"Polymorphism" is understood within the scope of the invention to refer to the presence in a population of two or more different forms of a gene, genetic marker, or inherited trait.

A "single-nucleotide polymorphism" or "SNP" is understood within the scope of the invention to refer to a DNA sequence variation occurring when a single nucleotide in the genome (or other shared sequence) differs between members of a species or between paired chromosomes in an individual. Two sequenced DNA fragments from different individuals containing a difference in a single nucleotide are called two alleles. Preferably, a SNP has only two alleles.

The term "polynucleotide" is understood herein to refer to polymeric molecule of high molecular weight which can be single-stranded or double-stranded, composed of monomers (nucleotides) containing a sugar, phosphate and a base which is either a purine or pyrimidine. A "polynucleotide fragment" is a fraction of a given polynucleotide molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. The term "polynucleotide" thus refers to a polymer of DNA or RNA which can be single- or double-stranded, optionally containing synthetic, non-natural or altered nucleotide bases capable of incorporation into DNA or RNA polymers. Unless otherwise indicated, a particular nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al., 1994). The term polynucleotide is used interchangeably with nucleic acid, nucleotide sequence and may include genes, cDNAs, and mRNAs encoded by a gene, etc.

The term "isolated", when used in the context of the nucleic acid molecules of the present invention, refers to a nucleic acid sequence that is identified within and isolated/separated from its chromosomal nucleic acid sequence context within the respective source organism. An isolated nucleic acid is not a nucleic acid as it occurs in its natural context, if it indeed has a naturally occurring counterpart. In contrast, non-isolated nucleic acids are nucleic acids such as DNA and RNA, which are found in the state they exist in nature. For example, a given DNA sequence (e.g. a gene) is found on the host cell chromosome in proximity to neighboring genes. The isolated nucleic acid sequence may be present in single-stranded or double-stranded form. Alternatively, it may contain both the sense and anti-sense strands (i.e., the nucleic acid sequence may be double-stranded). If claimed in the context of a plant genome, the nucleic acid molecule of the invention is distinguished over naturally occurring counterparts by the insertion side in the genome and the flanking sequences at the insertion site. In a preferred embodiment, the nucleic acid molecules of the present invention are understood to be isolated.

As used herein, the phrase "nucleic acid" refers to any physical string of monomer units that can be corresponded to a string of nucleotides, including a polymer of nucleotides (e.g., a typical DNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (when a gene encodes a protein), through "translation" of mRNA. Gene expression can be regulated at many stages in the process.

The term "chimeric gene" refers to any gene that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a sequence of nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The terms "protein," "peptide" and "polypeptide" are used interchangeably herein.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of ≥1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Overexpression" refers to the level of expression in transgenic cells or organisms that exceeds levels of expression in normal or untransformed (nontransgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes. Gene silencing includes virus-induced gene silencing.

"RNA interference" (RNAi) refers to the process of sequence-specific post-transcriptional gene silencing in plants and animals mediated by short interfering RNAs (siRNAs). Various terms such as siRNA, target RNA molecule, dicer or ribonuclease III enzyme are concepts known to those skilled in the art and full descriptions of these terms and other concepts pertinent to RNAi can be found in the literature. It is understood that any particular hypothesis describing the mechanisms of RNAi are not necessary to practice the present invention.

The term "siRNAs" refers to short interfering RNAs. In some embodiments, siRNAs comprise a duplex, or double-stranded region, of about 21-23 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

"dsRNA" or "double-stranded RNA" is RNA with two complementary strands, which directs the sequence-specific degradation of mRNA through a process known as RNA interference (RNAi). dsRNA is cut into siRNAs interfering with the expression of a specific gene.

The term "target RNA molecule" refers to an RNA molecule to which at least one strand of the short double-stranded region of a siRNA (or dsRNA) is homologous or complementary. Typically, when such homology or complementary is about 100% over a stretch of at least 21 nucleotides, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such RNA target molecules include unprocessed mRNA, ribosomal RNA, and viral RNA genomes. It is not necessary that there is 100% homology between the target RNA molecule and the dsRNA over the whole length of the dsRNA, but the hairpins of the dsRNA should comprise stretches of at least 21 nucleotides, preferably of at least 23 nucleotides, more preferred of at least 50 nucleotides, even more preferred of at least 500 nucleotides, most preferred of at least 700 nucleotides, and up to 1000 nucleotides having at least 95%, preferred 100% homology between the target RNA molecule.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc.

cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also Pearson, 1990, appended examples and (workbench.sdsc.edu/). For this purpose, the "default" parameter settings may be used.

Another indication that two nucleic acid sequences are "substantially identical" is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent conditions", "stringent hybridization conditions" or "stringent hybridization wash conditions" in the context of nucleic acid hybridization experiments, such as Southern and Northern hybridization, include reference to conditions under which a probe will hybridize to its target sequence, to a detectably greater degree than to other sequences. Stringent conditions are target sequence dependent, are different under different environmental parameters and will differ depending on the structure of the polynucleotide. Longer sequences hybridize specifically at higher temperatures. An extensive guide to the hybridization of nucleic acids is found in Tijssen P., 1993 *Laboratory Techniques in Biochemistry and Molecular Biology-Hybridization with Nucleic Acid Probes*, Part I, Chapter 2 "Overview of principles of hybridization and the strategy of nucleic acid probe assays" Elsevier, New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* (5$^{th}$ Ed. Cold Spring Harbor Laboratory, Cold Spring Harbor, N.Y.).

Specificity is typically the function of post-hybridization washes, the critical factors being the ionic strength and temperature of the final wash solution. Generally, highly stringent hybridization and wash conditions are selected to be about 5° lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight.

Often, a high stringency wash is preceded by a low stringency wash to remove background probe signal. An example of high stringent wash conditions is a 0.2×SSC wash at 65° C. for 15 minutes (see, Sambrook, infra, for a description of SSC buffer), whereas an example of very high stringent wash conditions is 0.15M NaCl at 72° C. for about 15 minutes. An example moderate (medium) stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C. The sequences of the present invention may be detected using all the above conditions. For the purposes of defining the invention, the high stringency conditions are used.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant. This also includes callus or callus tissue as well as extracts (such as extracts from taproots) or samples.

A "plant organ" is a distinct and visibly structured and differentiated part of a plant such as a root, stem, leaf, flower bud, or embryo. "Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "breeding", and grammatical variants thereof, refer to any process that generates a progeny individual. Breeding can be sexual or asexual, or any combination thereof. Exemplary non-limiting types of breeding include crossings, selfings, doubled haploid derivative generation, and combinations thereof.

"Selective breeding" is understood within the scope of the invention to refer to a program of breeding that uses plants that possess or display desirable traits as parents.

"Fermentation" as used herein refers to the process of transforming an organic molecule into another molecule using a micro-organism. For example, "fermentation" can refer to aerobic transforming sugars or other molecules from plant material, such as the plant material of the present invention, to produce alcohols (e.g., ethanol, methanol, butanol); organic acids (e.g., citric acid, acetic acid, itaconic acid, lactic acid, gluconic acid); ketones (e.g., acetone), amino acids (e.g., glutamic acid); gases (e.g., H2 and CO2), antibiotics (e.g., penicillin and tetracycline); enzymes; vitamins (e.g., riboflavin, B12, beta-carotene); and/or hormones. Fermentation include fermentations used in the consumable alcohol industry (e.g., beer and wine). Fermentation also includes anaerobic fermentations, for example, for the production of biofuels. Fermenting can be accomplished by any organism suitable for use in a desired fermentation step, including, but not limited to, bacteria, fungi, archaea, and protists. Suitable fermenting organisms include those that can convert mono-, di-, and trisaccharides, especially glucose and maltose, or any other biomass-derived molecule, directly or indirectly to the desired fermentation product (e.g., ethanol, butanol, etc.).

Suitable fermenting organisms also include those which can convert non-sugar molecules to desired fermentation products. Such organisms and fermentation methods are known to the person skilled in the art.

The term "biofuel" as used herein refers to any biofuel produced by aerobic or anaerobic fermentation of plant material. A non-limiting example of a biofuel obtained by aerobic fermentation is bioethanol. Biofuels that can be obtained by anaerobic fermentation include, but are not limited to biogas and/or biodiesel. Methods of aerobic and/or anaerobic fermentation are known to the person skilled in the art.

DETAILED DESCRIPTION

The present invention discloses transgenic sugar beet plants which have a phenotype of delayed bolting.

The cultivated sugar beet (*Beta vulgaris* ssp. *vulgaris* L.) is a biennial plant which forms a storage root and a leaf rosette in the first year. Shoot elongation (bolting) and flower formation starts after a period of low temperature, whereas many wild beets of the genus *B. vulgaris* ssp. maritima show an annual growing habit due to the presence of the bolting gene B at the B locus. The BOLTING gene (B gene) is responsible for the determination of the annual habit in sugar beet. Annuality in the *Beta* species is considered a monogenic and dominant trait. Plants carrying the dominant B allele are able to switch from juvenile to reproductive stages in a vernalization-independent manner, contrary to biennial plants carrying the b allele that obligatory require vernalization for bolting and subsequent flowering to occur. The dominant allele of locus B is abundant in wild beets and causes bolting under long days without the cold requirement usually essential for biennial cultivars (Abe et al., 1997) carrying the recessive allele. Although it was known that the B gene is a key player in the vernalization response in sugar beet via, the gene as such has not been identified so far.

The present inventors now used a candidate gene approach in order to identify and characterize putative bolting control genes in sugar beet. In this approach an EST sequence with accession number CV301305 was identified as the putative beet homologue of PRR7 by means of homology searches using BLAST (see Example 1.1). The corresponding amino acid sequence shows the partial presence of a Pseudo Response Regulator receiver (PRR, pfam00072) or Signal Receiver (REC, cd00156) domain (FIG. 1), a hallmark of the PRR gene family that all play key roles in the circadian clock (Nakamichi et al., 2005). FIG. 2 shows the alignment of the amino acid sequence of CV301305 with PRR7, its closest *Arabidopsis* homologue. The PSEUDO RESPONSE REGULATOR 7 (PRR7) gene as originally described in *Arabidopsis* is a member of the pseudo-response regulator gene family (PRR1 or TOC1, PRR3, PRR5, PRR7 and PRR9) that all contain two characteristic signatures: the response regulator receiver (REC) and CCT domains. Transcription levels of the PRR family members oscillate in a circadian fashion, which suggest that their proteins are closely associated with the circadian clock. In fact PRR7 is described in *Arabidposis* as a component of the temperature-sensitive circadian system (Nakamichi et al., 2007; Salomé and McClung 2005). In plants, the circadian clock is involved in the regulation of a number of fundamental biological processes, including leaf movement, diurnal changes in photosynthesis activities and photoperiodic control of flowering time (Imaizumi and Kay, 2006; Zhou et al., 2007). Recently, PRR7 homologues were identified and characterized in barley, wheat and rice (HvPPD, TaPPD and OsPRR37) and shown to be major determinants of the photoperiod response in cereals.

In one aspect of the invention the sequences of several annual and biennial alleles of BvPRR7, preferably the sequences as given in SEQ ID NOs: 1, 4, 5, 6, 7, 8, 9, 10, 53, or 54 are thus provided, which encode a protein which is functionally equivalent to the B gene.

Based on the EST sequence a partial beet PRR7 fragment of approximately 0.5 Kb as amplified and sequenced (see Example 1.1). Mapping experiments using a F2 population of 198 individuals derived from a cross between the annual line and a biennial line polymorphic for one SNP at position #160 showed that BvPRR7 maps at chromosome II at an approximate distance of 1 cM downstream of the GJ131 marker (FIG. 4), a region known to contain the B gene for vernalization-independent flowering (Möhring et al., 2004; Gaafar et al., 2005). The results of the marker assay show a perfect match between the predicted genotype of the B gene and the genotype of the BvPRR7 gene (see Example 1.1). The results of further mapping analysis, i.e., its map position, combined with is biological function relating to the temperature-sensitive circadian rhythm (Salomé and McClung, 2005) showed that BvPRR7 is a strong candidate for the B gene (Example 1.1).

In a next step a BAC library was screened using standard PCR techniques well known to those skilled in the art in order to recover the full-length genomic sequence of the sugar beet PRR7 gene (see Example 1.2). The BAC library used was a BAC library which has been established with DNA from the biennial commercial sugar beet cultivar H20. Partially (HindIII) digested HMW DNA of fragments in the size of 100-400 kb were size selected two times. The DNA fragments were ligated into the vector pBeloBAC-Kan. The library contains 57,600 clones with an average insert size of approximately 120 kb, corresponding to an 8× coverage of the beet genome. The redundancy has been tested by screening with single-copy probes and the frequency of clones from mitochondrial or plastid DNA was estimated to be lower than 1%. Subsequent screenings of the DNA pools for fragment BvPRR7 resulted in the positive identification of a BAC clone carrying the respective fragment.

In order to obtain the full-length sequence of the BvPRR7 gene, the previously identified BAC clone (BAC SBA079-L24) is sequenced using standard sequencing technology. Two non-overlapping contigs that both share sequence homology with EST CV301305 can then be combined into one single sequence (SEQ ID NO 8). Based on the alignment of the BAC sequence contigs to EST CV301305 and on sequence homology to the PRR7 gene from *Arabidopsis*, the putative gene structure of the beet BvPRR7 gene comprising introns and exons can be predicted as shown in FIG. 5. Based on this prediction the genomic sequence can be shown to span the entire BvPRR7 gene with 3.6 Kb of sequence upstream of the ATG stop codon and 2.2 Kb downstream of the coding region. The corresponding amino acid sequence of BvPRR7 is shown under SEQ ID NO 11. Alignment of the amino acid sequence of BvPRR7 to all members of the PRR gene family from *Arabidopsis* including TOC1 (PRR1), PRR3, PRR5, PRR7 and PRR9 illustrates the strong conservation of the Pseudo Response Regulator receiver domain (PRR) motif (pfam00072) near the NH2-terminus and the CCT motif (pfam06203) at the COOH—terminus (FIG. 6). In addition to the PRR gene family from *Arabidopsis*, BvPRR7 also shares strong homology to the PRR7 homologue in cereals as illustrated by the phylogenetic tree shown in FIG. 7. The PRR7 homologue in cereals, better known as Ppd, was shown to represent the major determinant of the photoperiod response (Turner et al, 2005; Beales et al, 2007). A function in the vernalization response as in sugar beet could not yet be demonstrated.

Based on their homology to known flowering-time control genes or their putative regulatory function as suggested by the presence of conserved domains representative of regulatory proteins, few genes can be identified as potential candidates for the B gene. These genes need further validation by allelic variability and/or gene expression studies between annual and biennial genotypes, or by means of complementation or knockout experiments using transgenic approaches. The annual plant habit conferred by the B gene behaves as a single dominant trait; the requirement for vernalization in biennial plants accordingly is recessive. The transformation of an annual allele of BvPRR7 into a biennial genotype thus is predicted to bestow the annual flowering behavior onto the biennial acceptor genotype. To verify this hypothesis, the coding sequence of an annual allele of BvPRR7 under the control of an annual promoter and terminator fragment is transformed into biennial genotype such as, for example G018 (see Example 2). Transformation can be accomplished by methods known in art such as that disclosed by Chang et al, 2002 using sugar beet meristems as explant material and the phosphomannose isomerase (PMI) gene as selectable marker. Transgenic shoots are checked for expression of the selection marker such as, for example, PMI activity (Joersbo et al, 1998) and subsequently rooted, potted in soil and transferred to the greenhouse. Negative controls consist of non-transgenic shoots that are subjected to the same in vitro regeneration procedure, but without *Agrobacterium* infection and selection. Plants are grown in growth chambers at a constant temperature of 18° C. and a photoperiod of 17 hours light and 7 hours dark. Under these conditions (without induction of bolting by applying cold temperatures) the non-transgenic biennial controls do not show any signs of bolting within an observation period of up to 12 weeks, whereas the annual control plants start to bolt normally within 6 to 8 weeks. Contrary to the non-transgenic biennial control plants, a substantial number of transgenic events starts bolting within four to ten weeks and basically behaves as annual plants despite their biennial genetic background. Transgenic plants that bolted and flowered are cross-pollinated with a biennial maintainer line to produce offspring. Progeny plants are tested for PMI activity and subsequently monitored for bolting and flowering without vernalization. These progeny plants show a one to one segregation ratio and a perfect correlation between PMI activity and the annual habit. These data confirm the causal relationship between BvPRR7 and vernalization-independent flowering in sugar beet.

The present inventors further found out that BvPRR7 plays a key role in the vernalization response in sugar beet and can thus be used for engineering bolting resistance into sugar beet plants by suppressing the vernalization response. In one aspect of the invention the BvPRR7 gene may thus be used in a transgenic approach for producing transgenic sugar beet plants comprising said polynucleotides stably integrated into the sugar beet genome. In particular, upon expression from the genome, the expression product can be used to modulate the vernalization response of the sugar beet plant by suppressing or down-regulating expression of the B gene.

The DNA sequences of interest are assembled into chimeric constructs which contain the nucleic acid sequence to be expressed in the transgenic plant under the control of regulatory elements which function in plants. Methods for assembling such chimeric constructs are well known to the person skilled in the art.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

For example, a plant promoter fragment may be employed which will direct expression of the gene in all tissue; of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include for example, the AP2 gene, ACT11 from *Arabidopsis* (Huang et al. Plant Mol. Biol. 33:125-139 (1996)), Cat3 from *Arabidopsis* (GenBank No. U43147, Zhong et al., Mol. Gen. Genet. 251:196-203 (1996)), the gene encoding stearoyl-acyl carrier protein desaturase from *Brassica napus* (Genbank No. X74782, Solocombe et al. Plant Physiol. 104: 1167-1176 (1994)), GPc1 from maize (GenBank No. X15596, Martinez et al. J. Mol. Biol 208:551-565 (1989)), and Gpc2 from maize (GenBank No. U45855, Manjunath et al., Plant Mol. Biol. 33:97-112 (1997)).

Alternatively, the plant promoter may direct expression of the nucleic acid molecules of the invention in a specific tissue or may be otherwise under more precise environmental or developmental control. Examples of environmental conditions that may affect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific or preferential promoter is one which directs expression specifically or preferentially in seed tissues, such promoters may be, for example, ovule-specific, embryo-specific, endosperm-specific, integument-specific, seed coat-specific, or some combination thereof. Examples include a promoter from the ovule-specific BEL1 gene described in Reiser et al. Cell 83:735-742 (1995) (GenBank No. U39944). Other suitable seed specific promoters are derived from the following genes: MAC1 from maize (Sheridan et al. Genetics 142:1009-1020 (1996), Cat3 from maize (GenBank No. L05934, Abler et al. Plant Mol. Biol. 22:10131-1038 (1993), the gene encoding oleosin 18 kD from maize (GenBank No, J05212, Lee et al. Plant Mol. Biol. 26:1981-1987 (1994)), vivparous-1 from *Arabidopsis* (Genbank No. U93215), the gene encoding oleosin from *Arabidopsis* (Genbank No. Z17657), Atmyc1 from *Arabidopsis* (Urao et al. Plant Mol. Biol. 32:571-576 (1996), the 2s seed storage protein gene family from *Arabidopsis* (Conceicao et al. Plant 5:493-505 (1994)) the gene encoding oleosin 20 kD from *Brassica napus* (GenBank No. M63985), napA from *Brassica napus* (GenBank No. J02798, Josefsson et al. JBL 26:12196-1301 (1987), the napin gene family from *Brassica napus* (Sjodahl et al. Planta 197:264-271 (1995), the gene encoding the 2S storage protein from *Brassica napus* (Dasgupta et al. Gene 133:301-302 (1993)), the genes encoding oleosin A (Genbank No. U09118) and oleosin B (Genbank No. U09119) from soybean and the gene encoding low molecular weight sulphur rich protein from soybean (Choi et al. Mol Gen, Genet. 246:266-268 (1995)).

Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

Furthermore, it is contemplated that promoters combining elements from more than one promoter may be useful. For example, U.S. Pat. No. 5,491,288 discloses combining a Cauliflower Mosaic Virus (CaMV) promoter with a histone promoter. Thus, the elements from the promoters disclosed herein may be combined with elements from other promoters.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Other sequences that have been found to enhance gene expression in transgenic plants include intron sequences (e.g., from Adh1, bronze1, actin1, actin 2 (WO 00/760067), or the sucrose synthase intron) and viral leader sequences (e.g., from TMV, MCMV and AMV). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie et al., 1987; Skuzeski et al., 1990). Other leaders known in the art include but are not limited to: Picornavirus leaders, for example, EMCV leader (Encephalomyocarditis 5 noncoding region) (Elroy-Stein et al., 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak et al., 1991); Untranslated leader from the coat protein mRNA of alfalfa mosaic virus (AMV RNA 4), (Jobling et al., 1987; Tobacco mosaic virus leader (TMV), (Gallie et al., 1989; and Maize Chlorotic Mottle Virus leader (MCMV) (Lommel et al., 1991. See also, Della-Cioppa et al., 1987.

Regulatory elements such as Adh intron 1 (Callis et al., 1987), sucrose synthase intron (Vasil et al., 1989) or TMV omega element (Gallie, et al., 1989), may further be included where desired.

Examples of enhancers include elements from the CaMV 35S promoter, octopine synthase genes (Ellis et al., 1987), the rice actin I gene, the maize alcohol dehydrogenase gene (Callis et al., 1987), the maize shrunken I gene (Vasil et al., 1989), TMV Omega element (Gallie et al., 1989) and promoters from non-plant eukaryotes (e.g., yeast; Ma et al., 1988).

One principal method for the control of expression is underexpression. For underexpression there are two principle methods which are commonly referred to in the art as "anti-sense downregulation" and "sense downregulation" (sense downregulation is also referred to as "cosuppression"). Generically these processes are referred to as "gene silencing". Both of these methods lead to an inhibition of expression of the target gene.

The invention comprises various strategies for reducing the expression, amount, activity and/or function of the of the nucleic acid molecule of the present invention. The skilled worker appreciates the fact that a number of various methods are available in order to influence the expression, amount, activity and/or function of the nucleic acid molecule of the present invention in the desired way. Examples which may be mentioned but which are not limiting are:

"Sense" Suppression

Alteration of the expression of a nucleotide sequence of the present invention, preferably reduction of its expression, is obtained by "sense" suppression (referenced in e.g., Jorgensen et al. (1996) Plant Mol. Biol. 31, 957-973). In this case, the entirety or a portion of a nucleotide sequence of the present invention is comprised in a DNA molecule. The DNA molecule is preferably operatively linked to a promoter functional in a cell comprising the target gene, preferably a plant cell, and introduced into the cell, in which the nucleotide sequence is expressible. The nucleotide sequence is inserted in the DNA molecule in the "sense orientation", meaning that the coding strand of the nucleotide sequence can be transcribed. In a preferred embodiment, the nucleotide sequence is fully translatable and all the genetic information comprised in the nucleotide sequence, or portion thereof, is translated into a polypeptide. In another preferred embodiment, the nucleotide sequence is partially translatable and a short peptide is translated. In a preferred embodiment, this is achieved by inserting at least one premature stop codon in the nucleotide sequence, which brings translation to a halt. In another more preferred embodiment, the nucleotide sequence is transcribed but no translation product is being made. This is usually achieved by removing the start codon, e.g., the "ATG", of the polypeptide encoded by the nucleotide sequence. In a further preferred embodiment, the DNA molecule comprising the nucleotide sequence, or a portion thereof, is stably integrated in the genome of the plant cell. In another preferred embodiment, the DNA molecule compris-ing the nucleotide sequence, or a portion thereof, is comprised in an extrachromosomally replicating molecule.

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 80% identical to the nucleotide sequence the expression of which is reduced, more preferably it is at least 90% identical, yet more preferably at least 95% identical, and most preferably at least 99% identical.

"Anti-Sense" Suppression

In another preferred embodiment, the alteration of the expression of a nucleotide sequence of the present invention, preferably the reduction of its expression is obtained by "anti-sense" suppression. The entirety or a portion of a nucleotide sequence of the present invention is comprised in a DNA molecule. The DNA molecule is preferably operatively linked to a promoter functional in a plant cell, and introduced in a plant cell, in which the nucleotide sequence is expressible. The nucleotide sequence is inserted in the DNA molecule in the "anti-sense orientation", meaning that the reverse complement (also called sometimes non-coding strand) of the nucleotide sequence can be transcribed. In a preferred embodiment, the DNA molecule comprising the nucleotide sequence, or a portion thereof, is stably integrated in the genome of the plant cell. In another preferred embodiment the DNA molecule comprising the nucleotide sequence, or a portion thereof, is comprised in an extrachromosomally replicating molecule. Several publications describing this approach are cited for further illustration (Green, P. J. et al., Ann. Rev. Biochem. 55:569-597 (1986); van der Krol, A. R. et al, Antisense Nuc. Acids & Proteins, pp. 125-141 (1991); Abel, P. P. et al., Proc. Natl. Acad. Sci. USA 86:6949-6952 (1989); Ecker, J. R. et al., Proc. Natl. Acad. Sci. USA 83:5372-5376 (Aug. 1986)).

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 80% identical to the nucleotide sequence the expression of which is reduced, more preferably it is at least 90% identical, yet more preferably at least 95% identical, and most preferably at least 99% identical.

Homologous Recombination

In another preferred embodiment, at least one genomic copy corresponding to a nucleotide sequence of the present invention is modified in the genome of the plant by homologous recombination as further illustrated in Paszkowski et al., EMBO Journal 7:4021-26 (1988). This technique uses the property of homologous sequences to recognize each other and to exchange nucleotide sequences between each by a process known in the art as homologous recombination. Homologous recombination can occur between the chromosomal copy of a nucleotide sequence in a cell and an incoming copy of the nucleotide sequence introduced in the cell by transformation. Specific modifications are thus accurately introduced in the chromosomal copy of the nucleotide sequence. In one embodiment, the regulatory elements of the nucleotide sequence of the present invention are modified. Such regulatory elements are easily obtainable by screening a genomic library using the nucleotide sequence of the present invention, or a portion thereof, as a probe. The existing regulatory elements are replaced by different regulatory elements, thus altering expression of the nucleotide sequence, or they are mutated or deleted, thus abolishing the expression of the nucleotide sequence. In another embodiment, the nucleotide sequence is modified by deletion of a part of the nucleotide sequence or the entire nucleotide sequence, or by mutation. Expression of a mutated polypeptide in a plant cell is also contemplated in the present invention. More recent refinements of this technique to disrupt endogenous plant genes have been described (Kempin et al., Nature 389:802-803 (1997) and Miao and Lam, Plant J., 7:359-365 (1995).

The skilled worker knows numerous possible processes of how to modify genomic sequences in a targeted manner. These include, in particular, processes such as the generation of knockout mutants by means of targeted homologous recombination, for example, by generating stop codons, shifts in the reading frame etc. (Hohn B and Puchta H (1999) Proc Natl Acad Sci USA 96:8321-8323) or the targeted deletion or inversion of sequences by means of, for example, sequence-specific recombinases or nucleases. In another preferred embodiment, a mutation in the chromosomal copy of a nucleotide sequence is introduced by transforming a cell with a chimeric oligonucleotide composed of a contiguous stretch of RNA and DNA residues in a duplex conformation with double hairpin caps on the ends. An additional feature of the oligonucleotide is for example the presence of 2'-O-methylation at the RNA residues. The RNA/DNA sequence is designed to align with the sequence of a chromosomal copy of a nucleotide sequence of the present invention and to contain the desired nucleotide change. For example, this technique is further illustrated in U.S. Pat. No. 5,501,967 and Zhu et al. (1999) Proc. Natl. Acad. Sci. USA 96: 8768-8773.

Ribozymes

In a further embodiment, the RNA coding for a polypeptide of the present invention is cleaved by a catalytic RNA, or ribozyme, specific for such RNA. The ribozyme is expressed in transgenic plants and results in reduced amounts of RNA coding for the polypeptide of the present invention in plant cells, thus leading to reduced amounts of polypeptide accumulated in the cells. This method is further illustrated in U.S. Pat. No. 4,987,071.

Dominant-Negative Mutants

In another preferred embodiment, the activity of the polypeptide encoded by the nucleotide sequences of this invention is changed. This is achieved by expression of dominant negative mutants of the proteins in transgenic plants, leading to the loss of activity of the endogenous protein.

Aptamers

In a further embodiment, the activity of polypeptide of the present invention is inhibited by expressing in transgenic plants nucleic acid ligands, so-called aptamers, which specifically bind to the protein. Aptamers are preferentially obtained by the SELEX (Systematic Evolution of Ligands by EXponential Enrichment) method. In the SELEX method, a candidate mixture of single stranded nucleic acids having regions of randomized sequence is contacted with the protein and those nucleic acids having an increased affinity to the target are partitioned from the remainder of the candidate mixture. The partitioned nucleic acids are amplified to yield a ligand enriched mixture. After several iterations a nucleic acid with optimal affinity to the polypeptide is obtained and is used for expression in transgenic plants. This method is further illustrated in U.S. Pat. No. 5,270,163.

Zinc Finger Proteins

A zinc finger protein that binds a nucleotide sequence of the present invention or to its regulatory region is also used to alter expression of the nucleotide sequence. Preferably, transcription of the nucleotide sequence is reduced or increased. Zinc finger proteins are for example described in Beerli et al. (1998) PNAS 95:14628-14633., or in WO 95/19431, WO 98/54311, or WO 96/06166, all incorporated herein by reference in their entirety.

dsRNA

Alteration of the expression of a nucleotide sequence of the present invention is also obtained by dsRNA interference (RNAi) The process of gene regulation by means of double-stranded RNA ("double-stranded RNA interference"; dsRNAi) has been described many times for animal and plant organisms (e.g., Matzke M A et al. (2000) Plant Mol Biol 43:401-415; Fire A. et al. (1998) Nature 391:806-811; WO 99/32619; WO 99/53050; WO 00/68374; WO 00/44914; WO 00/44895; WO 00/49035; WO 00/63364, all incorporated herein by reference in their entirety.). The processes and methods described in the references indicated are hereby explicitly referred to. dsRNAi processes are based on the phenomenon that simultaneously introducing the complementary strand and contour strand of a gene transcript suppresses expression of the corresponding gene in a highly efficient manner. Preferably, the phenotype caused is very similar to that of a corresponding knockout mutant (Waterhouse P M et al. (1998) Proc Natl Acad Sci USA 95:13959-64). The dsRNAi process has proved to be particularly efficient and advantageous in reducing marker protein expression.

Double-stranded RNA (dsRNA) molecule means within the scope of the invention preferably one or more ribonucleic acid sequences which, owing to complementary sequences, are theoretically (e.g. according to the base pair rules by Watson and Crick) and/or actually (e.g. owing to hybridization experiments in vitro and/or in vivo) capable of forming double-stranded RNA structures. The skilled worker is aware of the fact that the formation of double-stranded RNA structures represents a state of equilibrium. Preferably, the ratio of double-stranded molecules to corresponding dissociated forms is at least 1 to 10, preferably 1:1, particularly preferably 5:1, most preferably 10:1.

The present invention further relates to double-stranded RNA molecules which, when introduced into a plant organism (or into a cell, tissue, organ or propagation material derived therefrom) cause the reduction of expression of at least one target gene. The double-stranded RNA molecule for reducing expression of a target gene here preferably comprises a) a "sense" RNA strand comprising at least one ribonucleotide sequence which is essentially identical to at least a part of the "sense" RNA transcript of a target gene, and b) an "antisense" RNA strand which is essentially, preferably fully, complementary to the RNA sense strand under a).

"Essentially identical" means that the dsRNA sequence may also have insertions, deletions and also individual point mutations in comparison with the target gene sequence and nevertheless causes an efficient reduction in expression. The homology (as defined herein below) between the "sense" strand of an inhibitory dsRNA and at least one part of the "sense" RNA transcript of a target gene nucleic acid sequence (or between the "antisense" strand of the complementary strand of a nucleic acid sequence of a target gene) is preferably at least 75%, preferably at least 80%, very particularly preferably at least 90%, most preferably 100%.

A 100% sequence identity between dsRNA and a marker protein gene transcript is not absolutely necessary in order to cause an efficient reduction in target gene expression. Consequently, the process is advantageously tolerant toward sequence deviations as may be present due to genetic mutations, polymorphisms or evolutionary divergences. Thus it is possible, for example, using the dsRNA which has been generated starting from the sequence of the target gene of the first organism, to suppress target gene expression in a second organism. For this purpose, the dsRNA preferably includes sequence regions of the target gene transcripts which correspond to conserved regions. Said conserved regions may be readily derived from sequence comparisons.

Alternatively, an "essentially identical" dsRNA may also be defined as a nucleic acid sequence capable of hybridizing with part of a target gene transcript.

"Essentially complementary" means that the "antisense" RNA strand may also have insertions, deletions and also individual point mutations in comparison with the complement of this "sense" RNA strand. The homology between the "antisense" RNA strand and the complement of the "sense" RNA strand is preferably at least 80%, preferably at least 90%, very particularly preferably at least 95%, most preferably 100%.

"Part of the "sense" RNA transcript" of a nucleic acid sequence of a target gene means fragments of an RNA or mRNA transcribed or transcribable from a nucleic acid sequence of a target gene. In this context, the fragments have a sequence length of preferably at least 20 bases, preferably at least 50 bases, particularly preferably at least 100 bases, very particularly preferably at least 200 bases, most preferably at least 500 bases. The complete transcribable RNA or mRNA is also included. Included are also sequences such as those which may be transcribed under artificial conditions from regions of a target gene which are otherwise, under natural conditions, not transcribed, such as promoter regions, for example.

The dsRNA may consist of one or more strands of polyribonucleotides. Naturally, in order to achieve the same purpose, it is also possible to introduce a plurality of individual dsRNA molecules which comprise in each case one of the above-defined ribonucleotide sequence sections into the cell or the organism. The double-stranded dsRNA structure may be formed starting from two complementary, separate RNA strands or, preferably, starting from a single, self-complementary RNA strand. In this case, the "sense" RNA strand and the "antisense" RNA strand are preferably connected covalently to one another in the form of an inverted "repeat".

As described in WO 99/53050, for example, the dsRNA may also comprise a hairpin structure by connecting the "sense" and the "antisense" strands by a connecting sequence ("linker"; for example an intron). Preference is given to the self-complementary dsRNA structures, since they require only the expression of an RNA sequence and always comprise the complementary RNA strands in an equimolar ratio. The connecting sequence may is preferably an intron (e.g. an intron of the potato ST-LS1 gene; Vancanneyt G F et al. (1990) Mol Gen Genet 220(2):245-250).

The nucleic acid sequence coding for a dsRNA may include further elements such as, for example, transcription termination signals or polyadenylation signals.

Bringing together, if intended, the two strands of the dsRNA in a cell or plant may be achieved by way of example in the following way: a) transformation of the cell or plant with a vector comprising both expression cassettes, b) cotransformation of the cell or plant with two vectors, one of which comprises the expression cassettes containing the "sense" strand and the other one of which comprises the expression cassettes containing the "antisense" strand. The formation of the RNA duplex may be initiated either outside or inside the cell.

The dsRNA may be synthesized either in vivo or in vitro. For this purpose, a DNA sequence coding for a dsRNA may be inserted into an expression cassette under the control of at least one genetic control element (such as a promoter, for example). A polyadenylation is not necessary and neither need any elements for initiating a translation be present. Preference is given to the expression cassette for the dsRNA targeting the target gene being present on the transformation construct or the transformation vector. For this purpose, the expression cassettes coding for the "antisense" strand and/or the "sense" strand of a dsRNA targeting the target gene or for the self-complementary strand of the dsRNA are preferably inserted into a transformation vector and introduced into the plant cell by using the processes described below. A stable insertion into the genome may be advantageous for the process of the invention but is not absolutely necessary. Since a dsRNA causes a long-term effect, transient expression is also sufficient in many cases. The dsRNA may also be part of the RNA to be expressed by the nucleic acid sequence to be inserted by fusing it, for example, to the 3'-untranslated part of said RNA.

The dsRNA may be introduced in an amount which makes possible at least one copy per cell. Higher amounts (e.g. at least 5, 10, 100, 500 or 1000 copies per cell) may, if appropriate, cause a more efficient reduction.

For RNAi suppression a BvPRR7 the present inventors have assembled a cDNA fragment such as, for example the 0.6 Kb fragment depicted in SEQ ID NO: 1, into an RNAi cassette under the control of a constitutive promoter (see Example 3). Suitable constitutive promoters are, for example, the Ubi3 promoter from *Arabidopsis* (Norris et al, 1993), the CaMV 35S promoter, or any other promoter known to promote constitutive expression in sugar beet. The expression cassette further contains a selectable marker gene under the control of a suitable promoter. Particularly, the marker gene encodes a positive selection marker such as phosphomannose isomerase or a xylose isomerase. The inverted repeat of the BvPRR7 fragment is separated by the second intron from the potato StLS1 gene (Eckes et al, 1986; Vancanneyt et al, 1990) to stabilize the RNAi cassette, but also to improve the efficiency of the RNAi phenomenon (Wang and Waterhouse, 2001; Smith et al, 2000).

Insertion of a DNA Molecule (Insertional Mutagenesis)

In another preferred embodiment, a DNA molecule is inserted into a chromosomal copy of a nucleotide sequence of the present invention, or into a regulatory region thereof. Preferably, such DNA molecule comprises a transposable element capable of transposition in a plant cell, such as e.g., Ac/Ds, Em/Spm, mutator. Alternatively, the DNA molecule comprises a T-DNA border of an *Agrobacterium* T-DNA. The DNA molecule may also comprise a recombinase or integrase recognition site which can be used to remove part of the DNA molecule from the chromosome of the plant cell. Methods of insertional mutagenesis using T-DNA, transposons, oligonucleotides or other methods known to those skilled in the art are also encompassed. Methods of using T-DNA and transposon for insertional mutagenesis are described in Winkler et al. (1989) Methods Mol. Biol. 82:129-136 and Martienssen (1998) PNAS 95:2021-2026, incorporated herein by reference in their entireties. Further suitable methods are the introduction of nonsense mutations into endogenous target genes, for example, by means of introducing RNA/DNA oligonucleotides into the plant (Zhu et al. (2000) Nat Biotechnol 18(5): 555-558). Point mutations may also be generated by means of DNA-RNA hybrids which are also known as "chimeraplasty" (Cole-Strauss et al. (1999) Nucl Acids Res 27(5):1323-1330; Kmiec (1999) Gene therapy American Scientist 87(3):240-247).

Deletion Mutagenesis

In yet another embodiment, a mutation of a nucleic acid molecule of the present invention is created in the genomic copy of the sequence in the cell or plant by deletion of a portion of the nucleotide sequence or regulator sequence. Methods of deletion mutagenesis are known to those skilled in the art. See, for example, Miao et al, (1995) Plant J. 7:359. The activity or amount of the expression of a target gene may also be reduced by a targeted deletion in the target gene, for example by sequence-specific induction of DNA double-strand breaks at a recognition sequence for specific induction of DNA double-strand breaks in or close to the nucleic acid sequence of the target gene.

In yet another embodiment, this deletion is created at random in a large population of plants by chemical mutagenesis or irradiation and a plant with a deletion in a gene of the present invention is isolated by forward or reverse genetics. Irradiation with fast neutrons or gamma rays is known to cause deletion mutations in plants (Silverstone et al, (1998) Plant Cell, 10:155-169; Bruggemann et al., (1996) Plant J., 10:755-760; Redei and Koncz in *Methods in Arabidopsis Research*, World Scientific Press (1992), pp. 16-82). Deletion mutations in a gene of the present invention can be recovered in a reverse genetics strategy using PCR with pooled sets of genomic DNAs as has been shown in *C. elegans* (Liu et al., (1999), Genome Research, 9:859-867. ). A forward genetics strategy would involve mutagenesis of a line displaying PTGS followed by screening the M2 progeny for the absence of PTGS. Among these mutants would be expected to be some that disrupt a gene of the present invention. This could be assessed by Southern blot or PCR for a gene of the present invention with genomic DNA from these mutants.

In still another embodiment, the expression of the nucleotide sequence of the present invention is altered in every cell of a plant. This is for example obtained though homologous recombination or by insertion in the chromosome. This is also for example obtained by expressing a sense or antisense RNA, zinc finger protein or ribozyme under the control of a promoter capable of expressing the sense or antisense RNA, zinc finger protein or ribozyme in every cell of a plant. Constructs for expression of the sense or antisense RNA, zinc finger protein or ribozyme, or for overexpression of a nucleotide sequence of the present invention, are prepared and transformed into a plant cell according to the teachings of the present invention, e.g., as described infra.

A combined application is also conceivable. Further methods are known to the skilled worker and may comprise hindering or stopping the processing of the target gene, the transport of the protein encoded by the target gene or of its mRNA, the inhibition of ribosome attachment, the inhibition of RNA splicing, the induction of an enzyme degrading target gene RNA and/or the inhibition of translational elongation or termination.

The invention hence also provides sense and anti-sense nucleic acid molecules corresponding to the sequences set forth in SEQ ID NOs: 1, 4, 5, 6, 7, 8, 9, 10, 53, or 54 of the Sequence Listing as well as their orthologs.

The genes and open reading frames according to the present invention which are substantially similar to a nucleotide sequence encoding a polypeptide as given in SEQ ID NO: 6 including any corresponding anti-sense constructs can be operably linked to any promoter that is functional within the plant host including the promoter sequences according to the invention or mutants thereof.

Once completed, the polynucleotide construct of the invention comprising an expression cassette or an RNAi cassette may be mobilized into a suitable vector for plant transformation, such as, for example, a binary vector, which may then be mobilized to sugar beet using one of the well known transformation techniques such as, for example, *Agrobacterium*-mediated transformation.

Transgenic plants (or plant cells, or plant explants, or plant tissues) incorporating and expressing the nucleic acid sequences or dsRNA of the invention can be produced by a variety of well established techniques. Following construction of the chimeric construct of the invention comprising an expression cassette or an RNAi cassette incorporating a nucleic acid sequence according to the invention and as described herein before, standard techniques can be used to introduce the chimeric construct into a plant, a plant cell, a plant explant or a plant tissue of interest. Optionally, the plant cell, explant or tissue can be regenerated to produce a transgenic plant. The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al., eds., (1984) Handbook of Plant Cell Culture—Crop Species, Macmillan Publ. Co., New York, N.Y.; Shimamoto et al. (1989) Nature 338: 274 276; Fromm et al. (1990) Bio/Technol. 8: 833 839; and Vasil et al. (1990) Bio/Technol. 8: 429 434. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation.

Transformation of plants can be undertaken with a single DNA molecule or multiple DNA molecules (i.e., co-transformation), and both these techniques are suitable for use with the chimeric constructs of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the polynucleotide construct of the invention. The general descriptions of plant expression vectors and reporter genes, and *Agrobacterium* and *Agrobacterium*-mediated gene transfer, can be found in Gruber et al. (1993).

Expression vectors containing a nucleic acid sequence according to the invention can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues, (Lindsey et al., 1993; Auch & Reth et al.).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., 1985: Byrne et al., 1987; Sukhapinda et al., 1987; Lorz et al., 1985; Potrykus, 1985; Park et al., 1985: Hiei et al., 1994). The use of T-DNA to transform plant cells has received extensive study and is amply described (EP 120516; Hoekema, 1985; Knauf, et al., 1983; and An et al., 1985). For introduction into plants, the chimeric constructs of the invention can be inserted into binary vectors as described in the examples.

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway et al., 1986), electroporation (Riggs et al., 1986), *Agrobacterium*-mediated transformation (Hinchee et al., 1988), direct gene transfer (Paszkowski et al., 1984), and ballistic particle acceleration using devices available from Agracetus, Inc., Madison, Wis. and BioRad, Hercules, Calif. (see, for example, Sanford et al., U.S. Pat. No. 4,945,050; and McCabe et al., 1988). Also see, Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1988 (maize); Fromm et al., 1990 (maize); and Gordon-Kamm et al., 1990 (maize); Svab et al., 1990 (tobacco chloroplast); Koziel et al., 1993 (maize); Shimamoto et al., 1989 (rice); Christou et al., 1991 (rice); European Patent Application EP 0 332 581 (orchardgrass and other Pooideae); Vasil et al., 1993 (wheat); Weeks et al., 1993 (wheat). In one embodiment, the protoplast transformation method for maize is employed (European Patent Application EP 0 292 435, U. S. Pat. No. 5,350,689).

The main focus of the present invention is on transformation of sugar beet. The experimental procedures for the transformation of sugar beet are well known to those skilled in the art such as that disclosed by Chang et al, 2002 using sugar beet meristems as explant material or as described by Joersbo et al, 1998.

In a preferred embodiment (as shown in Example 3) the RNAi cassette can be transformed into a biennial sugar beet genotype such as, for example, G018. Transgenic shoots are checked for expression of the selection marker such as, for example, PMI activity (Joersbo et al, 1998). Positive shoots and non-transgenic controls are rooted and transferred to the greenhouse for an acclimatization period of two weeks minimum at 18° C. prior to the vernalization treatment. Once well-established, the transgenic plants are exposed to the vernalization treatment consisting of a period of 14 weeks at a constant temperature of 6° C. and 12 hours low artificial light. Prior to applying bolting-inductive conditions, vernalized plants are slowly acclimatized for two weeks in climate chambers by stepwise increasing the temperature from 10 to 18° C. Plants are subsequently repotted into to larger pots (2 liter), and monitored for bolting while exposed to a constant temperature of 18° C. and a long-day photoperiod of 17 hours light/7 hours dark.

After transformed plant cells or plants are selected and grown to maturity, those plants showing the trait of interest are identified. The trait can be any of those traits described above. Additionally, to confirm that the trait of interest is due to the expression of the introduced nucleic acid sequence of interest under control of the regulatory nucleotide according to the invention, expression levels or activity of the polypeptide or nucleic acid sequence of interest can be determined by analyzing mRNA expression using Northern blots, RT-PCR or microarrays, or protein expression using immunoblots or Western blots or gel shift assays.

The invention thus relates to plant cells and tissues, to plants derived from such cells and tissues, respectively, to plant material, to the progeny and to seeds derived from such plants, and to agricultural products including processed plant products obtainable by, for example, any one of the transformation methods described below.

Once an expression cassette according the present invention and as described herein before comprising a nucleic acid sequence according to the invention has been transformed into a particular plant species, it may be propagated in that species or moved into other varieties of the same species, particularly including commercial varieties, using traditional breeding techniques. Preferred plants of the invention include gymnosperms, monocots, and dicots, especially agronomically important crop plants, such as rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The genetic properties engineered into the transgenic plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. Use of the advantageous genetic properties of the transgenic plants according to the invention can further be made in plant breeding that aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

One skilled in the art will recognize that the transgenic genotype of the present invention can be introgressed by breeding into other plant lines (preferably sugar beet plant lines) comprising different transgenic or non-transgenic genotypes. This different transgenic or non-transgenic genotype could be any genotype, but a genotype comprising at least one trait of interest is preferred. For example, a sugar beet inbred comprising the transgenic genotype of the present invention can be crossed with a sugar beet inbred line comprising the transgenic genotype of an event resistant to a different virus known to infect sugar beet plants. The resulting seed and progeny plants will have the trait of delayed bolting and the resistance traits in stacked form. For example, a sugar beet inbred with the transgenic genotype of the present invention can be crossed with a sugar beet inbred comprising the transgenic genotype of the glyphosate resistant H7-1 event (European patent application EP-A1-1597373, herein incorporated by reference). The resulting seed and progeny plants have both the resistance trait and the trait of delayed bolting. Further traits, like herbicide resistance, disease resistance or resistance against viruses (i.e., viruses like, for example, BNYVV in either transgenic from or from conventional sources (like Holly or C48) or viruses other than BNYVV) can also used for stacking with transgenic genotype of the present invention. It will be further recognized that other combinations or stacks can be made with the transgenic genotype of the invention and thus these examples should not be viewed as limiting.

One skilled in the art will also recognize that transgenic sugar beet seed comprising the transgenic genotype of the present invention can be treated with various seed-treatment chemicals, including various pesticides and insecticides, to further augment the resistance of the present invention.

The transgenic genotype of the present invention can be introgressed in any sugar beet inbred or hybrid using art recognized breeding techniques. The goal of plant breeding is to combine in a single variety or hybrid various desirable traits. For field crops, these traits may include resistance to insects and diseases (e.g., derived from conventional sources including, but not limited to Holly and C48), tolerance to herbicides, tolerance to heat and drought, greater yield, and better agronomic quality. With mechanical harvesting of many crops, uniformity of plant characteristics such as germination and taproot establishment, growth rate, maturity, and root size, is important.

In another aspect, the present invention provides a method for producing hybrid seeds from which sugar beet plants with a phenotype of delayed bolting. Such methods comprise: (a) providing a sugar beet line with a phenotype of delayed bolting, particularly a transgenic sugar beet plant according to the present invention as a first parent line, (b) providing a second sugar beet line having a different genotype as a second parent line; (c) allowing the plants of the first parent line of step (a) and the plants of the second parent line of step (b) to pollinate each other, let the seed develop, and harvest the hybrid seed, wherein the harvested hybrid seeds are seeds of a sugar beet hybrid plant having a phenotype of delayed bolting. In an embodiment of this aspect, the first parental line provided in step (a) is an inbred sugar beet line comprising one or more or all polynucleotides of the present invention. In a further embodiment of this aspect, the second parental line is selected from the group consisting of (a) an inbred sugar beet plant line resistant to at least one virus affecting sugar beet, such as, for example, Beet necrotic yellow vein virus; (b) an inbred sugar beet plant line resistant to at least one herbicide; and (c) an inbred sugar beet plant line having resistant to at least one disease. Examples of common viruses and diseases affecting sugar beet and sources for resistance against these viruses or diseases are known to the person skilled in the art. Further, herbicides used on sugar beet and sources of resistance against these herbicides are also known to the person skilled in the art.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Plant breeding techniques known in the art and used in a sugar beet plant breeding program include, but are not limited to, recurrent selection, backcrossing, pedigree breeding, restriction length polymorphism enhanced selection, genetic marker enhanced selection and transformation. The development of sugar beet hybrids in a sugar beet plant breeding program requires, in general, the development of homozygous inbred lines, the crossing of these lines, and the evaluation of the crosses. Pedigree breeding and recurrent selection breeding methods are used to develop inbred lines from breeding populations. Sugar beet plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a sugar beet plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included into the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1→F2; F2→F3; F3→F4; F4→F5; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a sugar beet plant-breeding program, elite inbreds can be used as a parental line or starting material or source population and can serve as either the donor or recurrent parent.

A single cross hybrid results from the cross of two inbred lines, each of which has a genotype that complements the genotype of the other. The hybrid progeny of the first generation is designated F1. In the development of commercial hybrids in a sugar beet plant-breeding program, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a sugar beet hybrid in a sugar beet plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in sugar beet, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor exhibited by F1 hybrids is lost in the next generation (F2). Consequently, seed from hybrids is not used for planting stock.

In hybrid seed production it is preferred to eliminate or inactivate pollen production by the female parent. Incomplete removal or inactivation of the pollen provides the potential for self-pollination. This inadvertently self-pollinated seed may be unintentionally harvested and packaged with hybrid seed. Once the seed is planted, it is possible to identify and select these self-pollinated plants. These self-pollinated plants will be genetically equivalent to the female inbred line used to produce the hybrid. Typically these self-pollinated plants can be identified and selected due to their decreased vigor. Female selfs are identified by their less vigorous appearance for vegetative and/or reproductive characteristics. Identification of these self-pollinated lines can also be accomplished through molecular marker analyses.

However, simple and efficient pollination control systems exist which ensure utilizing heterosis by excluding self-pollination in commercial hybrid seed production. If one of the parents is a self-incompatible (SI), cytoplasmic male sterile (CMS) or nuclear male sterile (NMS) plant that is not able to self-pollinate or is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross. Cytoplasmic male sterility (CMS) is a maternally inherited phenomenon, the genetic determinants of which are located in the genome of the cytoplasmic organelles, the mitochondria. Such plants are severely impaired in their ability to produce functional pollen grains. Restorer genes for CMS systems are dominant nuclear genes, which suppress male sterile effects of the cytoplasm. The expression of male sterility in CMS plants is the result of incompatibility between recessive nuclear gene and male sterile specific cytoplasmic genome.

In a preferred embodiment, a CMS system is applied for production of the hybrid sugar beet plants of the present invention. In such a system a male sterile CMS line is used as female parent which is pollinated by a male fertile line used as male parent. The trait of delayed bolting according to the present invention can be present in both the CMS male sterile (female) parent line or the male fertile (male) parent line or even both. Preferably, the trait of delayed bolting is kept on the male sterile side in order to avoid GM contaminations via the pollen containing the trait shed by the male parent.

As is readily apparent to one skilled in the art, the foregoing are only some of the various ways by which the inbred of the present invention can be obtained by those looking to introgress the transgenic genotype of the invention into other sugar beet lines. Other means are available and known to the person skilled in the art, and the above examples are illustrative only.

In general, the second parent line used for the hybrid production can also be a sugar beet plant line having the phenotype of delayed bolting like, for example, a sugar beet plant of the present invention. Preferably, the first parent line and the second parent line employed in the production of the hybrid seed are based on genetically diverse backgrounds. Genetic distance can be measured by the use of molecular markers as described for example in Knaak (1996). However, the second parent line could also be a sugar beet inbred comprising another trait of interest like, for example but not limited to glyphosate resistant (e.g. containing the H7-1 event as described in the European patent application EP-A1-1597373, herein incorporated by reference). The resulting hybrid seed will contain the stacked traits of delayed bolting and herbicide glyphosate. Further traits, like herbicide resistance, disease resistance or resistance against BNYVV from conventional sources (like Holly or C48) or viruses other than BNYVV can also be comprised in the second parent line for stacking with transgenic genotype of the present invention in the hybrid seed. It will be further recognized that other combinations or stacks can be made with the transgenic genotype of the invention and thus these examples should not be viewed as limiting. Another preferred embodiment of the present invention relates to hybrid seed of a sugar beet plant having a phenotype of delayed bolting. In one aspect of the present invention said hybrid seed is produced by the method for producing sugar beet hybrid seed of sugar beet plants having a phenotype of delayed bolting of the present invention. Such methods are known to the person skilled in the art. In yet another aspect of the present invention a hybrid sugar beet plant having a phenotype of delayed bolting is provided that is produced by growing the hybrid seed of the present invention. Preferably, this hybrid plant is not bolting at all, i.e. show complete suppression of the vernalization response. A further preferred embodiment of the present invention relates to a part of said hybrid sugar beet plant of the present invention. Preferably said part is selected from the group comprising seeds, embryos, microspores, zygotes, protoplasts, cells, ovules, pollen, taproots, cotyledons, or other reproductive or vegetative parts or extracts or samples.

According to another aspect of the invention, methods of detecting the presence of a nucleic acid sequence or a chimeric construct of the present invention in a biological sample are provided. Such methods comprise: (a) contacting the sample comprising DNA with a pair of primers that, when used in a nucleic-acid amplification reaction with genomic DNA from a sugar beet carrying a nucleic acid sequence or a chimeric construct of the present invention, produces an amplicon that is diagnostic for a sugar beet of the present invention; (b) performing a nucleic acid amplification reaction, thereby producing the amplicon; and (c) detecting the amplicon. Detection of the amplicon can be conducted by any means well known in the art including but not limited to fluorescent, chemiluminescent, radiological, immunological, or otherwise. In the case in which hybridization is intended to be used as a means for amplification of a particular sequence to produce an amplicon, the production and detection by any means well known in the art of the amplicon is intended to be indicative of the intended hybridization to the target sequence where one probe or primer is utilized, or sequences where two or more probes or primers are utilized.

Further encompassed are methods for producing sugar, wherein a sugar beet plant of the present invention, or cells or tissues, a biological sample or an extract thereof is processed to produce sugar. Further, sugar is provided by the present invention that is produced by the method of producing sugar of the present invention. The method for producing sugar can be any conventional method for producing sugar known to person skilled in the art.

Another preferred aspect relates to a method for producing one or more biofuel(s) selected from the group comprising ethanol, biogas and/or biodiesel, by processing a transgenic sugar beet plant of the present invention, or cells or tissues, or a biological sample or an extract thereof to produce the one or more biofuel(s). The biofuel can be any biofuel produced by aerobic or anaerobic fermentation of plant material. A non-limiting example of a biofuel obtained by aerobic fermentation is bioethanol.

Biofuels that can be obtained by anaerobic fermentation include, but are not limited to biogas and/or biodiesel. Methods of aerobic and/or anaerobic fermentation are known to the person skilled in the art. Further encompassed by the present invention are biofuels selected from the group comprising ethanol, biogas and/or biodiesel as produced by the method for producing one or more biofuel(s) or the present invention.

In another preferred aspect the present invention provides polynucleotide markers which maps at or in close vicinity to the B locus, particularly at a distance of 1 cM upstream of markers MP0176 and GJ01 and co-segregates with marker GJ131 (Möhring S. et al, 2004; Gaafar R. M. et al, 2005) (FIG. 5).

The invention further relates to polynucleotide markers identified in the sugar beet genome including variants and derivatives thereof, which polynucleotide markers are developed based on a nucleic acid sequence which is obtainable from a genomic DNA region that shows perfect co-segregation with the bolting gene (B gene) associated phenotype in sugar beet and wherein the marker allows to discriminate between annual and biennial genotype or between different haplotypes within a plant grouping of sugar beet plants exhibiting a biennial or annual phenotype. In a preferred embodiment the polynucleotide markers of the present invention have a nucleic acid sequence obtainable from one or more of the nucleic acid sequences of the present invention and as described above. Preferably, the polynucleotide markers of the present invention further comprise one or more polymorphisms, particularly a polymorphism that is based on an SNP, an SSR, a deletion or an insertion of at least one nucleotide, but especially a polymorphism based on an SNP, which polymorphism is diagnostic for the B allele at the B locus. Such polynucleotide markers are preferably capable of detecting at least one of the various SNPs present in the different alleles of the genomic sequence set forth as SEQ ID NO: 8 herein and shown in Tables 7-1 (further depicted in FIG. 11) and 7-2 (further depicted in FIG. 12), wherein said polynucleotide marker is capable of differentiating between different alleles, particularly between annual and biennial sugar beet lines. In a preferred embodiment the polynucleotide marker of the present invention are capable of detecting at least one SNP selected from the group comprising SNPs at positions #224, #351, #615, #897, #1082, #1841, #1915, #2334, #11592, #12316, #12490, or #12544 of the sequence set forth as SEQ ID NO: 8 and as shown in Tables 7-1 (further depicted in FIG. 11) and 7-2 (further depicted in FIG. 12). A further aspect of the present invention relates to a set of polynucleotide markers comprising a plurality of the polynucleotide markers of the present invention and described above. In this context, the term "plurality" refers to a set of more than one polynucleotide marker, which preferably consists of two, three or more markers.

In one aspect of the invention, markers may be developed and used which are not explicitly disclosed herein or markers even yet to be identified. Based on the information provided in this application it will be possible, for a skilled person, to identify or develop markers not explicitly disclosed herein but genetically closely linked to, or, preferably, located within the bolting gene or B gene or linked to the markers disclosed herein. The skilled person knows that other markers may provide at least equal utility in screening assays and marker assisted selection.

Molecular markers, preferentially End point TaqMan®, can, for example, be developed based on SNPs characterized from sequenced PCR products that are amplified from annual and biennial plants. Here, several PCR amplifications will be performed in order to cover the whole sequence of the gene. New molecular markers will then be tested within different annual and biennial genetic backgrounds to evaluate the robustness of the molecular test.

In one embodiment, a molecular marker is a DNA fragment amplified by PCR, e.g., a SSR marker or a RAPD marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait.

In a specific embodiment of the invention simple sequence repeat (SSR) markers are used to identify invention-relevant alleles in the parent plants and/or the ancestors thereof, as well as in the progeny plants resulting from a cross of said parent plants.

There are several further methods or approaches available, known to those skilled in the art, which can be used to identify and/or develop markers in linkage disequilibrium and/or linked to and/or located in the B gene region, as well as markers that represent the actual causal mutations responsible for the biennial genotype. Without being fully exhaustive some approaches, known by those skilled in the art, include:

- use of disclosed sequences/markers in hybridization approaches to identify other sequence in the region of interest: primer sequences as disclosed herein and/or marker/gene sequences (or part thereof) that can be determined using the primer sequences as disclosed herein may be used as (hybridization) probes in isolating nucleic acid sequences/genes flanking the markers and/or linked and/or associated and/or specific for the B gene region from a genomic nucleic acid sample and/or RNA or cDNA sample or pool of samples (for example screening of genomic resources like BAC libraries or gDNA or cDNA library screening);
- use of disclosed sequences/markers in PCR approaches to identify other sequence in the region of interest: primer sequences as disclosed herein and/or marker/(candidate) gene sequences (or part thereof) that can be determined using the primer sequences as disclosed may be used as (PCR) amplification primers to amplify a nucleic acid sequence/gene flanking and/or linked to and/or associated with and/or specific for the QTL region from a genomic nucleic acid sample and/or RNA or cDNA sample or pool of samples either or not isolated from a specific plant tissue and/or after specific treatment of the plant and from sugar beet or in principal any other organism with sufficient homology;
- use of disclosed sequences/markers in PCR approaches to identify other sequence in the region of interest: the nucleotide sequences/genes of one or more markers can be determined after internal primers for said marker sequences may be designed and used to further determine additional flanking sequence/genes within the B gene region and/or genetically linked and/or associated with the trait;
- use of disclosed sequences/markers in mapping and/or comparative mapping approaches to identify markers in the same region(s) (positioning of the B gene on other maps): based on positional information and/or marker information as disclosed herein, markers, of any type, may be identified by genetic mapping approaches, eventually (if already needed) by positioning of the disclosed markers (by genetic mapping or extrapolation based on common markers across maps) on a (high density) genetic map(s), and/or integrated genetic or consensus map(s). Markers already known and/or new markers genetically linked and/or positioned in the vicinity of the disclosed markers and/or B gene region may be identified and/or obtained and eventually used in B gene (fine-) mapping and/or B gene cloning and/or MAS breeding applications;
- use of disclosed sequences/markers in 'in-silico' approaches to identify additional sequences/markers/(candidate) genes in B gene region(s): primer sequences as disclosed herein and/or marker/(candidate) gene sequences (or part thereof) that can be determined using the primer sequences as disclosed herein or based on linked markers may be used in 'in-silico' methods to search sequence or protein databases (e.g., BLAST) for (additional) flanking and/or homolog sequences/genes and/or allelic diversity (both genomic and/or cDNA sequences or even proteins and both originating from capsicum and/or any other organism) genetically linked and/or associated with the traits as described herein and/or or located in the B gene region;
- use of disclosed sequences/markers in physical mapping approaches (positioning of B gene on physical map or genome sequence): primer sequences as disclosed herein and/or marker/gene sequences (or part thereof) that can be determined using the primer sequences as disclosed herein or using other markers genetically linked to the markers disclosed herein and/or located in the B gene region may be positioned on a physical map and/or (whole) genome sequence in principal of any organism with sufficient homology to identify (candidate) sequences/markers/genes applicable in B gene (fine-mapping) and/or B gene cloning and/or MAS breeding applications;
- use of disclosed sequences/markers to position B-gene on other (physical) maps or genomes (across species) primer sequences as disclosed herein and/or marker/gene sequences (or part thereof) that can be determined using the primer sequences as disclosed herein may be used in comparative genome or syntheny mapping approaches to identify homolog region and homolog and/or ortholog sequences/(candidate) genes genetically linked and/or positioned in the B gene region and applicable in B gene (fine-mapping) and/or B gene cloning and/or MAS breeding applications;
- use of disclosed sequences/markers to select the appropriate individuals allowing the identification of markers in region of interest by genetic approaches: primer sequences and/or markers as disclosed herein may be used to select individuals with different/contrasting B gene alleles. Genetic association approaches and/or bulk segregant analysis (BSA, Michelmore et al., 1991) can be used to identify markers/genes in the specific region (B gene region) of interest and/or associated or genetically linked to the described traits; or
- use of disclosed information to search for (positional) candidate genes: the disclosed information may be used to identify positional and/or functional candidate genes which may be associated with the described traits and/or genetically linked.

In another specific embodiment of the invention a marker based on a single nucleotide polymorphism is used to identify invention-relevant alleles in the parent plants and/or the ancestors thereof, as well as in the progeny plants resulting from a cross of said parent plants.

The majority of commercial seed productions for sugar beet are done in southern France and northern Italy. In both regions, the presence of annual weed beets can cause pollen contamination in the seed productions, resulting in annuals in the commercial seed. This is not acceptable to a customer, and therefore all commercial seed lots are grown in regions, such as Argentina where no wild beets are growing directly after harvesting the seed. The plants are not vernalized and the presence of bolters is used to identify seed lots contaminated with annuals.

The polynucleotide markers according to the invention may therefore be used for quality control of commercial seed lots by screening of commercial biennial sugar beet seed for annual contaminants and for identifying annuals/biennials in breeding programs, which use the annual trait to speed up the breeding process, or when the annual trait is introduced together with new sources of genetic variation.

Different assays based on the gene sequence according to the invention and as described herein above can thus be developed and used to screen plant material for the presence or absence of the annuality allele.

In the past molecular marker techniques have been developed which can be used for genetic mapping, gene cloning, marker assisted plant breeding and for genome fingerprinting and investigating genetic relationships. Genetic markers are developed based on DNA polymorphisms in the nucleotide sequences of genomic regions and can either be detected by restriction enzymes, or by means of two priming sites.

There are several types of molecular markers that may be used in marker-based selection including restriction fragment length polymorphism (RFLP), random amplification of polymorphic DNA (RAPD), amplified restriction fragment length polymorphism (AFLP), single sequence repeats (SSR) and single nucleotide polymorphisms SNPs.

The information content of the different types of markers may be different depending on the method that was used to obtain the marker data and the population in which the markers were scored. For example, it is not always possible to distinguish genome fragments that are present in homozygous condition from heterozygous fragments. In a heterogeneous population like an $F_2$, co-dominant markers like restriction fragment length polymorphisms (RFLPs, Botstein et al., 1980) and co-dominantly scored amplified fragment length polymorphisms (AFLPs, Vos et al., 1995) yield more information than dominant markers like random amplified polymorphic DNAs (RAPDs, Welsh and McCleland, 1990) and dominantly scored AFLPs. RFLPs are co-dominant and are able to identify a unique locus. RFLP involves the use of restriction enzymes to cut chromosomal DNA at specific short restriction sites, polymorphisms result from duplications or deletions between the sites or mutations at the restriction sites.

AFLP requires digestion of cellular DNA with a restriction enzyme before using PCR and selective nucleotides in the primers to amplify specific fragments. With this method up to 100 polymorphic loci can be measured and only relatively small DNA sample are required for each test.

The most preferred method of achieving such amplification of nucleotide fragments that span a polymorphic region of the plant genome employs the polymerase chain reaction ("PCR") (Mullis et al., 1986), using primer pairs involving a backward primer and a forward primer that are capable of hybridizing to the proximal sequences that define a polymorphism in its double-stranded form.

In contrast to RFLPs, PCR-based techniques require only a small percentage (approximately 10%) of the DNA amount as template to produce large quantities of the target sequence by PCR amplification.

One such PCR based technique is RAPD, which utilizes low stringency polymerase chain reaction (PCR) amplification with single primers of arbitrary sequence to generate strain-specific arrays of anonymous DNA fragments. The method requires only tiny DNA samples and analyses a large number of polymorphic loci. However, the unpredictable behaviour of short primers which is affected by numerous reaction conditions, inheritance in a dominant manner, and population specificity are the main disadvantages of RAPDs.

Microsatellites, or simple sequence repeats (SSRs), simple sequence length polymorphisms (SSLPs), short tandem repeats (STRs), simple sequence motifs (SSMs), and sequence target microsatellites (STMs) represent a class of repetitive sequences which are widely dispersed throughout the genome of eukaryotes. The variation in number and length of the repeats is a source of polymorphism even between closely related individuals. SSR analysis is based on these (short-repeat) sequences which are selectively amplified to detect variations in simple sequence repeats. Such microsatellite sequences can be easily amplified by PCR using a pair of flanking locus-specific oligonucleotides as primers and detect DNA length polymorphisms (Litt and Luty, 1989; Weber and May, 1989).

Mutations at a single nucleotide position resulting in substitutions, deletions or insertions give rise to single nucleotide polymorphisms or SNPs, which occur approximately every 1.3 kb in human (Cooper et al., 1985; Kwok et al., 1996). Most polymorphisms of this type have only two alleles and are also called biallelic loci. Positional cloning based on SNPs may accelerate the identification of disease traits and a range of biologically informative mutations (Wang et al., 1998).

PCR extension assays that efficiently pick up point mutations may be used to detect SNPs. The procedure requires little DNA per sample. Three widely used types of SNP detection assays using PCR method are cleaved amplified polymorphic sequences (CAPS) (Konieczny and Ausubel, 1993; Thiel et al., 2004), derived CAPS (dCAPS) (Michaels and Amasino, 1998; Neff et al., 1998), and single strand conformation polymorphism (SSCP) (Orita et al., 1989).

CAPS polymorphisms are differences in restriction fragment lengths caused by SNPs or INDELs that create or abolish restriction endonuclease recognition sites in PCR amplicons produced by locus-specific oligonucleotide primers. CAPS assays are performed by digesting locus-specific PCR amplicons with one or more restriction enzymes and then separating the digested DNA on agarose or polyacrylamide gels.

dCAPS is a modification of the CAPS technique that allows detection of most single-nucleotide changes by utilizing mismatched PCR primers. Using the method, a restriction enzyme recognition site that includes the SNP is introduced into the PCR product by a primer containing one or more mismatches to template DNA. The PCR product modified in this manner is then subjected to restriction enzyme digestion, and the presence or absence of the SNP is determined by the resulting restriction pattern.

The SSCP technique separates denatured double stranded DNA on a non-denaturing gel, and thus allows the secondary structure, as well as the molecular weight, of single stranded DNA to determine gel mobility.

The ARMS (amplification refractory mutation system)-PCR procedure (Ye et al., 2001) involves the use of a single PCR for SNP genotyping (Fan et al., 2003; Chiapparino et al., 2004). A tetra-primer, employing two primer pairs, is used to amplify two different alleles of a SNP in a single PCR reaction.

Alternative methods may be employed to amplify such fragments, such as the "Ligase Chain Reaction" ("LCR") (Barany, F., 1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., 1988). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al., 1990 have described a nucleic acid detection assay that combines attributes of PCR and OLA (Nickerson et al., 1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of a nucleic acid having the sequence of the resulting "di-oligonucleotide," thereby amplifying the di-oligonucleotide, are also known (Wu and Wallace, 1989), and may be readily adapted to the purposes of the present invention.

In still another embodiment of the invention a marker based on a deletion or an insertion ("INDEL") of at least one nucleotide is used to identify invention-relevant alleles in the parent plants and/or the ancestors thereof, as well as in the progeny plants resulting from a cross of said parent plants. These markers can be developed based on the sequence of the polynucleotides according to the invention and as described herein before.

In particular, the markers according to the present invention can be used in an allelic discrimination assay, particularly in an assay for discriminating between different haplotypes within plant groupings of sugar beet plants exhibiting a biennial genotype. Said assay is based on a set of probe polynucleotides comprising two separate probe molecules that are complementary, for example, to a subregion of the BvPRR7 gene obtainable by PCR amplification based on forward primer PRR7(T1)-F and reverse primer PRR7(T1)-R as given in SEQ ID NO: 13 and SEQ ID NO: 14, respectively, which probe molecules differ only by one base mismatch and are probes PRR7(T1)-VIC (SEQ ID NO: 15) and PRR7(T1)-FAM (SEQ ID NO: 16). Further preferred sets are forward primer PRR7(T6)-F as depicted in SEQ ID NO: 49 and reverse primer PRR7(T6)-R as depicted in SEQ ID NO: 50 together with probes PRR7(T6)-VIC (SEQ ID NO: 51) and PRR7(T6)-FAM (SEQ ID NO: 52), as well as forward primer 1r22(T1)-F as depicted in SEQ ID NO: 55 and reverse primer 1r22(T1)-R as depicted in SEQ ID NO: 56 together with probes rr22(T1)-VIC (SEQ ID NO: 57) and 1r22(T1)-FAM (SEQ ID NO: 58).

Such assays, wherein a set of probe polynucleotides is employed, preferably comprise at least two separate probe molecules which differ by at least one mismatch, particularly by two or more mismatches located at adjacent sites, but especially by one single mismatch, wherein a first probe molecule, particularly a labelled probe molecule, more particularly a probe molecule labelled with a first fluorescent dye and a quencher, represents one allele and a second probe molecule, particularly a labelled probe molecule, more particularly a probe molecule labelled with a second fluorescent dye and a quencher, which is not identical with the first dye, represents the other allele, and wherein said set of probe polynucleotides is used for discriminating between the two allelic variants. Further two different fluorescent labels can be employed, the fluorescence of which can be easily distinguished. For example, a first probe is labelled with a first fluorescent dye (like, for example FAM) and a second probe is labelled with a second fluorescent dye (like, for example VIC). In a preferred embodiment of such an assay of the present invention the amplified fragment obtained in step b) of the allelic discrimination assay of the present invention described above is additionally probed with a second fluorescence-labelled probe molecule comprising a sequence specific for the biennial allele. In this assay an increase of the dye fluorescence of the first probe only is indicative of the presence of the annual allele. The two dyes used in this assay are preferably VIC and FAM. Generally, the assays of the present invention preferably employ two 2 primers (i.e., a pair of primers according to the invention) and at least one probe for the annual allele. A second probe can further be employed, which is a probe for the biennial allele.

In another aspect of the invention, an assay is provided involving markers that can discriminate specifically between annual plants and biennial plants and can thus be used, for example, for quality control of seed lots.

In particular, the invention relates to an assay, which is based on a set of probe polynucleotides comprising two separate probe molecules that are complementary, for example, to a to a subregion of the BvPRR7 gene obtainable by PCR amplification based on forward primer PRR7(T1)-F and reverse primer PRR7(T1)-R as given in SEQ ID NO: 13 and SEQ ID NO: 14, respectively, which probe molecules differ only by one base mismatch and are probes PRR7(T1)-VIC (SEQ ID NO: 15) and PRR7(T1)-FAM (SEQ ID NO: 16). Further preferred sets are forward primer PRR7(T6)-F as depicted in SEQ ID NO: 49 and reverse primer PRR7(T6)-R as depicted in SEQ ID NO: 50 together with probes PRR7(T6)-VIC (SEQ ID NO: 51) and PRR7(T6)-FAM (SEQ ID NO: 52), as well as forward primer 1r22(T1)-F as depicted in SEQ ID NO: 55 and reverse primer 1r22(T1)-R as depicted in SEQ ID NO: 56 together with probes rr22(T1)-VIC (SEQ ID NO: 57) and 1r22(T1)-FAM (SEQ ID NO: 58).

In another aspect the present invention provides a method for identifying annual contaminations in commercial seeds. Preferably this method comprises the use of the marker-based allelic discrimination assay of the present invention and described herein.

The following examples are intended solely to illustrate one or more preferred embodiments of the invention and are not to be construed as limiting the scope of the invention.

EXAMPLES

The following Examples provide illustrative embodiments. In light of the present disclosure and the general level of skill in the art, the skilled person will appreciate that the following Examples are intended to be exemplary only and that numerous changes, modifications, and alterations can be employed without departing from the scope of the presently claimed subject matter.

Example 1

Characterization of the Sugar Beet PRR7 Gene

Example 1.1

Mapping of the Putative PRR7 Homologue from Sugar Beet

Based on a candidate gene approach for the identification and characterization of putative bolting control genes in sugar beet, the EST sequence with accession number CV301305 was identified as the putative beet homologue of PRR7 by means of homology searches using BLAST. SEQ ID NO: 1 shows the nucleotide sequence of EST CV301305. The corresponding amino acid sequence shows the partial presence of a Pseudo Response Regulator receiver (PRR, pfam00072) or Signal Receiver (REC, cd00156) domain (FIG. 1), a hallmark of the PRR gene family that all play key roles in the circadian clock (Nakamichi et al., 2005). FIG. 2 shows the alignment of the amino acid sequence of CV301305 with PRR7, its closest *Arabidopsis* homologue, which has been described as a component of the temperature-sensitive circadian system (Nakamichi et al., 2007; Salomé and McClung 2005). The circadian clock is known to control several developmental processes in plants including flowering time control (Imaizumi and Kay, 2006; Zhou et al., 2007).

Based on the above observations, the putative gene structure of the partial beet PRR7 fragment was deduced using the alignment between the genomic sequence and the mRNA of the *Arabidopsis* PRR7 gene (AT5G02810 and NM_120359, respectively) to the BvPRR7 sugar beet EST (CV301305), which revealed the presence of several putative intronic regions (FIG. 3). Primers PRR7-F and PRR7-R (SEQ ID NOs: 2 and 3) encompassing the third putative intronic region delivered an amplification product of approximately 0.5 Kb when using genomic beet DNA as template. The PCR conditions for the amplification reaction were as follows: primary denaturation at 95° C. for 5 min followed by 35 amplification cycles of 30 seconds at 95° C., 30 seconds at 60° C. and 30 seconds at 72° C. and followed by 5 min at 72° C. PCR experiments were run at a GeneAMP PCR System 9600 instrument from Applied Biosystems Inc. using Platinum Taq DNA polymerase and the corresponding reaction mix from Invitrogen Corporation as recommended by the supplier. Sequence analysis of the PCR product enabled the reconstruction of the genomic sequence around intron 3 of the BvPRR7 gene fragment, and confirmed the presence of an intron of 296 base pairs in length (SEQ ID NO: 4).

The genomic fragment of the BvPRR7 gene was amplified and sequenced across a panel of sugar beet parental lines consisting of 15 biennial and one annual line. All biennial lines revealed monomorphic for BvPRR7 as only two different haplotypes were observed: one biennial allele and one annual allele (Table 1). In order to map BvPRR7 in a population segregating for the annual habit, an assay was developed targeting the SNP at position #160 (SEQ ID NO: 4) using the EndPoint TaqMan® technology. Table 2 summarizes the nucleotide sequences of the primers and probes designed for the PRR7(T1) TaqMan® assay targeting SNP at position #160; the reactions further consisted of the TaqMan® Universal PCR Master Mix, No AmpErase® UNG (2×) from Applied Biosystems Inc. according to the manufacturer's recommendations. The PCR amplification was performed as follows: 95° C. for 10 min followed by 40 cycles of 95° C. for 15 sec and 60° C. for 1 min, using an ABI PRISM 7700 Sequence Detector instrument. EndPoint measurement was performed using the Sequence Detection System 2.0 software.

TABLE 1

Polymorphisms observed between 1 annual and 15 biennial sugar beet lines for the BvPRR7 gene fragment spanning intron 3.

| SEQ ID NO 4: pos. | 87 | 160 | 406 | |
|---|---|---|---|---|
| haplotype#1 | T | T | G | annual |
| haplotype#2 | C | C | A | biennial |

The header row indicates the nucleotide position at the genomic sequence of the BvPRR7 gene fragment (as depicted in SEQ ID NO: 4). The rows titled "haplotype#1" and "haplotype#2" represent the 2 haplotypes observed across the panel of 16 lines.

TABLE 2

Nucleotide sequences of primers and probes corresponding to the TaqMan assay PRR7(T1) for the genotyping of SNP #160

| Precursor names | Nucleotide sequence (5' to 3') | SEQ ID NO: |
|---|---|---|
| PRR7(T1)-F | GAGGTGTCACAGTGTAAGTGTCT | 13 |
| PRR7(T1)-R | AAAGACTGCTACACGAACCACTAAG | 14 |
| PRR7(T1)-FAM | FAM-CTGATGAAAAGCTG-MGB-NFQ | 16 |
| PRR7(T1)-VIC | VIC-CTGATGGAAAGCTG-MGB-NFQ | 15 |

Using the above PRR7(T1) assay, the BvPRR7 gene was mapped in a F2 population of 198 individuals derived from a cross between the annual line and a biennial line polymorphic for the SNP at position #160. BvPRR7 maps at chromosome II at an approximate distance of 1 cM downstream of the GJ131 marker (FIG. 4), a region known to contain the B gene for vernalization-independent flowering (Möhring et al., 2004; Gaafar et al., 2005). The results of the PRR7(T1) assay show a perfect match between the predicted genotype of the B gene and the genotype of the BvPRR7 gene. The genotype of the B gene was predicted based on phenotypic evaluation of the F3 populations derived from the individual F2 plants for vernalization-independent flowering. Table 3 summarizes the graphical representation of the fine-map of the B gene region for 9 individual progeny plants comprising the closest recombination events. The combination of its map position and its biological function relating to the temperature-sensitive circadian rhythm (Salomé and McClung, 2005) obviously make BvPRR7 a strong candidate for the B gene.

TABLE 3

Genotypes for a number of markers including PRR7(T1) mapping around the B gene across nine F2 plants showing recombination events at either side of the B gene. PRR7(T1), as well as 9_27(T2) marker, show a perfect match to the predicted genotype of the B gene. The genotype of the B gene is based on phenotypic evaluation of the F3 populations derived from the individual F2 plants. (B—biennial allele; A—annual allele; H—heterozygous for the annual allele)

| | No. of recombinations | 98775103 | 98775161 | 98775167 | 98775176 | 98775206 | 98775214 | 98775153 | 98775237 | 98775245 |
|---|---|---|---|---|---|---|---|---|---|---|
| E8M4:193 | −5 | B | A | H | H | A | H | H | A | H |
| E05M16:24 | −3 | B | A | H | H | A | B | A | A | H |
| E15M4:162 | −2 | B | A | H | H | A | B | A | H | H |

TABLE 3-continued

Genotypes for a number of markers including PRR7(T1) mapping around the B gene across nine F2 plants showing recombination events at either side of the B gene. PRR7(T1), as well as 9_27(T2) marker, show a perfect match to the predicted genotype of the B gene. The genotype of the B gene is based on phenotypic evaluation of the F3 populations derived from the individual F2 plants.
(B—biennial allele; A—annual allele; H—heterozygous for the annual allele)

|  | No. of recombinations | 98775103 | 98775161 | 98775167 | 98775176 | 98775206 | 98775214 | 98775153 | 98775237 | 98775245 |
|---|---|---|---|---|---|---|---|---|---|---|
| E15M4:159 | −2 | B | A | H | H | A | B | A | H | H |
| GJ131 | −2 | B | A | H | H | A | B | A | H | H |
| 9_27 | 0 | B | H | B | H | A | B | A | H | H |
| PRR7 | 0 | B | H | B | H | A | B | A | H | H |
| B gene | 0 | B | H | B | H | A | B | A | H | H |
| GJ01 | 3 | H | H | B | A | H | B | A | H | H |
| MP0176 | 3 | H | H | B | A | H | B | A | H | H |
| E13M4-196 | 3 | H | H | B | A | H | B | A | H | H |
| E09M08-113 | 3 | H | H | B | A | H | B | A | H | H |
| E09M08-124 | 3 | H | H | B | A | H | B | A | H | H |
| E09M08:03 | 3 | H | H | B | A | H | B | A | H | H |
| E13M04:36 | 3 | H | H | B | A | H | B | A | H | H |
| MS0278 | 3 | H | H | B | A | H | B | A | H | H |
| E09M08-588 | 3 | H | H | B | A | H | B | A | H | H |
| E8M4:174 | 3 | H | H | B | A | H | B | A | H | H |
| E13M04:50 | 3 | H | H | B | A | H | B | A | H | H |
| E16M16:19 | 4 | H | H | B | A | H | B | A | H | B |
| E16M16:17 | 4 | H | H | B | A | H | B | A | H | B |
| E16M16:20 | 4 | H | H | B | A | H | B | A | H | B |

Example 1.2

Recovery of the Full-Length Genomic Sequence of BvPRR7

Using the primers PRR7-F and PRR7-R, a sugar beet BAC library was screened by means of PCR. The library was developed from the biennial commercial cultivar H2O and calculated to represent 6 genome equivalents with an average insert size of 120 Kb (McGrath et al., 2004). DNA pools for this library are distributed by Amplicon Express, Pullman Wash. The PCR conditions for the screening of the DNA pools were as follows: primary denaturation at 95° C. for 5 min followed by 35 amplification cycles of 30 seconds at 95° C., 30 seconds at 60° C. and 30 seconds at 72° C. and followed by 5 min at 72° C. PCR experiments were run at a GeneAMP PCR System 9700 instrument from Applied Biosystems Inc. using Platinum Taq DNA polymerase and the corresponding reaction mix from Invitrogen Corporation as recommended by the supplier. Subsequent screenings of the DNA pools for the presence of the BvPRR7 fragment according to the supplier's instructions resulted in the positive identification of BAC SBA079-L24.

In order to obtain the full-length sequence of the BvPRR7 gene, BAC SBA079-L24 was sent to MWG Biotech AG, Germany for sequence analysis by means of the 454 sequencing technology. Where necessary, gaps between the obtained contigs were filled by regular Sanger sequencing to yield one single genomic sequence for the BvPRR7 gene (SEQ ID NO: 8). Based on the alignment of the genomic sequence to EST CV301305 and on sequence homology to the PRR7 gene from *Arabidopsis*, the putative gene structure of the beet BvPRR7 gene comprising introns and exons was predicted as shown in FIG. 5. The corresponding amino acid sequence of BvPRR7 is shown under SEQ ID NO: 11. Alignment of the amino acid sequence of BvPRR7 to all members of the PRR gene family from *Arabidopsis* including TOC1 (PRR1), PRR3, PRR5, PRR7 and PRR9 illustrates the strong conservation of the Pseudo Response Regulator receiver domain (PRR) motif (pfam00072) near the NH2-terminus and the CCT motif (pfam06203) at the COOH-terminus (FIG. 6). In addition to the PRR gene family from *Arabidopsis*, BvPRR7 also shares strong homology to the PRR7 homologue in cereals as illustrated by the phylogenetic tree shown in FIG. 7. The tree shown in FIG. 7 was constructed by applying the Neighbor-Joining method (Saitou and Nei, 1987) on several members of PRR gene family from several plant species including *Beta vulgaris* BvPRR7, *Arabidopsis thaliana* (TOC1, NP_200946; PRR3, NP_568919; PRR5, NP_568446; PRR7, NP_568107; and PRR9, NP_566085), *Oryza sativa* (PRR37, Q0D3B6), *Hordeum vulgare* (PPD-H1, AAY17586) and *Triticum aestivum* (PPD-D1, ABL09477). The unrooted dendrograms were generated from the alignment of the amino acid sequences using ClustalW, and the phylogenetic tree was displayed by MEGA4 (Tamura et al., 2007). Bootstraps values for 1000 re-samplings are shown on each branch. Surprisingly, the PRR7 homologue in cereals, better known as Ppd, is known to represent a major determinant of the photoperiod response (Turner et al., 2005; Beales et al., 2007) rather than the vernalization response as suggested here for sugar beet.

Example 1.3

Fine-Mapping of the B Locus

Based on the results of the initial mapping described in Example 1.1 above, a large fine-resolution mapping was initiated to saturate the region around molecular markers GJ131 and GJ01 used for mapping and to confirm the correlation between the predicted genotype of the B gene and the genotype of the BvPRR7 gene. A total of 5157 F2 individuals obtained from several populations segregating for the annual habit, were analyzed with the two flanking markers GJ01(T1) and GJ131(T1) (Gaafar et al., 2005). In total 71 F2 plants were identified that have recombined between the two flanking markers. The mapping interval for the B gene was accordingly calculated at 0.69 cM. The recombinant plants were subsequently genotyped using the PRR7(T1) assay described above and the 9_27(T2) and ED031700(T1) assays available for the interval as disclosed in European patent application EP 1 995 320 A1. Table 4 summarizes the nucleotide sequences of the primers and probes designed for the GJ131(T1), 9_27 (T2), ED031700(T1), PRR7(T1) and GJ01(T1) TaqMan® assays; the reactions further employed the TaqMan® Universal PCR Master Mix, No AmpErase® UNG (2×) from Applied Biosystems Inc. according to the manufacturer's recommendations. The PCR amplification was performed as follows: 95° C. for 10 min followed by 40 cycles of 95° C. for 15 sec and 60° C. for 1 min, using an Applied Biosystems 7500 Real-Time PCR System instrument.

TABLE 4

Nucleotide sequences of primers and probes used in the GJ131(T1), 9_27(T2), ED031700(T1), PRR7(T1) and GJ01(T1) TaqMan ® assays, respectively.

| | SEQ ID NO | sequence |
|---|---|---|
| GJ131(T1) Assay | | |
| Forward primer | 17 | GCCCGTACAAACAAAGACTTCTC |
| Reverse primer | 18 | ACGCAGAATGTTGATGATGATACA |
| TaqMan VIC probe | 19 | TCCATCTCTCCACAGCTT |
| TaqMan VAM probe | 20 | TCCATCTCCCCACAGCT |
| 9_27(T2) Assay | | |
| Forward primer | 25 | TGCCAAAACACACATTGTACCTATACA |
| Reverse primer | 26 | TGCCTCTGGCTCCTTGAAG |
| TaqMan VIC probe | 27 | CATCTCTACAACACTACC |
| TaqMan VAM probe | 28 | ATCTCTACAAGACTACC |
| ED031700(T1) Assay | | |
| Forward primer | 21 | TAAAGGTGGTAATTTTAGAGAATTTTAGGA |
| Reverse primer | 22 | GCTCGTTTTGAAAAAATTTGGG |
| TaqMan VIC probe | 23 | TTTAATTCGCATCCTTCT |
| TaqMan VAM probe | 24 | TTAATTCGCAAACTTCT |
| PRR7(T1) Assay | | |
| Forward primer | 13 | GAGGTGTCACAGTGTAAGTGTCT |
| Reverse primer | 14 | AAAGACTGCTACACGAACCACTAAG |
| TaqMan VIC probe | 15 | CTGATGGAAAGCTG |
| TaqMan VAM probe | 16 | CTGATGAAAGCTG |
| GJ01(T1) Assay | | |
| Forward primer | 29 | GAACCCAGGATTACTCGTGAGC |
| Reverse primer | 30 | AAAAGTAGAATAAAATGTAACCTCCTCCATCTC |
| TaqMan VIC probe | 31 | ACGCAAGATAACATCAC |
| TaqMan VAM probe | 32 | ACGCAAGATAACGTCAC |

The allelic status of the B gene was deduced from the phenotypic observations made on the individual F2 plants (i.e. bolting or non-bolting under long-day conditions of 18 hours day and 6 hours night), as well as the corresponding progeny populations obtained by selfing of the F2 plants. Table 5 provides a graphical representation of the fine-resolution map of the B gene region summarizing the genotypic and phenotypic data obtained for the various recombinant plants. The perfect correlation between the genotype of the PRR7 gene and the phenotype across all recombinants allows to conclude that the beet PRR7 homologue is indeed the B gene. When assuming a single recombination event at each side of the B gene, the mapping interval for the B gene is now reduced to 0.02 cM, with the PRR7 gene co-localizing on top of the B gene for the annual habit.

TABLE 5

Graphical representation of the fine-resolution map of the B gene region. "A" and "B" genotypes for each marker correspond to the annual and biennial alleles, respectively. The interval in which the B gene is located is indicated by the two flanking black columns and is based on the phenotypes observed on each F2 recombinant plants.
(B—biennial allele; A—annual allele; H—heterozygous for the annual allele)

| line | F2 phenotype | GJ131(T1) | ED031330 (T1) | 9_27(T2) | B locus | 1R22(T1) | PRR7(T1) | B locus | GJ01(T1) |
|---|---|---|---|---|---|---|---|---|---|
| P1-0580 | annual | A | A | A | | A | A | | H |
| P1-0678 | annual | A | A | A | | A | A | | H |
| P1-0977 | annual | A | A | A | | A | A | | H |
| P1-1383 | annual | A | A | A | | A | A | | H |
| P2-0969 | annual | A | A | A | | A | A | | H |
| P2-1178 | annual | A | A | A | | A | A | | H |
| P3-0103 | annual | A | A | A | | A | A | | H |
| P3-0176 | annual | A | A | A | | A | A | | H |
| P1-0960 | annual | A | H | H | | H | H | | H |
| P2-0116 | annual | A | H | H | | H | H | | H |
| P2-0991 | annual | A | H | H | | H | H | | H |
| P2-2437 | annual | A | H | H | | H | H | | H |
| P1-1026 | annual | H | H | H | | H | H | | A |
| P1-1494 | annual | H | H | H | | H | H | | A |
| P2-1445 | annual | H | H | H | | H | H | | A |
| P2-2294 | annual | H | H | H | | H | H | | A |
| P2-2425 | annual | H | H | H | | H | H | | A |
| P4-0028 | annual | H | H | H | | H | H | | A |
| P4-0054 | annual | H | H | H | | H | H | | A |
| P1-1469 | annual | H | H | H | | A | A | | A |
| P4-0021 | annual | H | H | H | | A | A | | A |
| P3-0161 | annual | H | A | A | | A | A | | A |
| P3-0167 | annual | H | A | A | | A | A | | A |

TABLE 5-continued

| ID | type | 1 | 2 | 3 | 4 | 5 | 6 | 7 |
|---|---|---|---|---|---|---|---|---|
| P1-0630 | annual | H | A | A | | A | A | A |
| P1-1047 | annual | H | A | A | | A | A | A |
| P1-1120 | annual | H | A | A | | A | A | A |
| P1-1406 | annual | H | A | A | | A | A | A |
| P4-0046 | annual | H | A | A | | A | A | A |
| P4-0070 | annual | H | A | A | | A | A | A |
| P1-0549 | biennial | B | B | B | | B | B | H |
| P1-0685 | biennial | B | B | B | | B | B | H |
| P1-0727 | biennial | B | B | B | | B | B | H |
| P1-1102 | biennial | B | B | B | | B | B | H |
| P1-1296 | biennial | B | B | B | | B | B | H |
| P1-1299 | biennial | B | B | B | | B | B | H |
| P1-1435 | biennial | B | B | B | | B | B | H |
| P1-1823 | biennial | B | B | B | | B | B | H |
| P2-2227 | biennial | B | B | B | | B | B | H |
| P4-0020 | biennial | B | B | B | | B | B | H |
| P4-0142 | biennial | B | B | B | | B | B | H |
| P3-0206 | biennial | B | B | B | | B | B | H |
| P5-0019 | biennial | B | B | B | | B | B | H |
| P5-0043 | biennial | B | B | B | | B | B | H |
| P5-0047 | biennial | B | B | B | | B | B | H |
| P1-0335 | annual | B | B | B | H | H | | H |
| P1-0735 | annual | B | B | H | H | H | | H |
| P1-0301 | annual | B | H | H | H | H | | H |
| P1-1818 | annual | B | H | H | H | H | | H |
| P2-0115 | annual | B | H | H | H | H | | H |
| P2-0186 | annual | B | H | H | H | H | | H |
| P2-0239 | annual | B | H | H | H | H | | H |
| P4-0082 | annual | B | H | H | H | H | | H |
| P4-0094 | annual | B | H | H | H | H | | H |
| P4-0114 | annual | B | H | H | H | H | | H |
| P6-0163 | annual | B | H | H | H | H | | H |
| P1-0691 | annual | H | H | H | H | H | | B |
| P1-1016 | annual | H | H | H | H | H | | B |
| P1-1429 | annual | H | H | H | H | H | | B |
| P2-0740 | annual | H | H | H | H | H | | B |
| P4-0015 | annual | H | H | H | H | H | | B |
| P5-0072 | annual | H | H | H | H | H | | B |
| P1-1410 | biennial | H | H | H | B | B | | B |
| P1-0379 | biennial | H | B | B | B | B | | B |
| P1-0390 | biennial | H | B | B | B | B | | B |
| P1-0487 | biennial | H | B | B | B | B | | B |
| P1-0508 | biennial | H | B | B | B | B | | B |
| P1-0632 | biennial | H | B | B | B | B | | B |
| P1-1132 | biennial | H | B | B | B | B | | B |
| P1-1163 | biennial | H | B | B | B | B | | B |
| P2-0415 | biennial | H | B | B | B | B | | B |

Example 1.4

Gene Expression Analysis of BvPRR7

For gene expression analysis, seedlings from annual, biennial and vernalized biennial plants were grown in controlled environment chambers at a constant temperature of 18° C. and a photoperiod of 16 hours light/8 hours dark (LDs) or 8 hours light/16 hours dark (SDs), respectively. Leaf samples were harvested every two hours over a period of 24 hours and total RNA was isolated using the RNAqueous®-4PCR Kit commercialized by Ambion, basically following the supplier's instructions. The RNA samples were converted to cDNA using the RETROscript® Kit (Ambion) starting from 1 μg of total RNA as template. The expression of the BvPRR7 gene was measured by means of quantitative PCR (qPCR) using the Power SYBR® Green PCR Master Mix (Applied Biosystems Inc.) on a Real Time PCR 7500 System instrument. The PCR conditions were as follows: primary denaturation at 95° C. for 10 min followed by 40 amplification cycles of 15 seconds at 95° C. and 1 min at 60° C. The nucleotide sequences of the forward and reverse primer for BvPRR7 are as follows: 5'-TTGGAGGAGGTGTCACAGTTCTAG-3' (SEQ ID NO: 45) and 5'-TGTCATTGTCCGACTCT-TCAGC-3' (SEQ ID NO: 46), respectively. The isocitrate dehydrogenase (BvICDH) gene (AF173666) was used as reference gene for normalizing the expression of BvPRR7. The primer sequences designed for this reference gene consisted of 5'-CACACCAGATGAAGGCCGT-3' (SEQ ID NO: 47) and 5'-CCCTGAAGACCGTGCCAT-3' (SEQ ID NO: 48). Expression levels were calculated as the average of three biological replicates and each qPCR reaction was repeated three times.

As illustrated in FIG. 8, BvPRR7 shows a diurnal oscillation of expression for all three classes of plants (i.e. annual, biennial and vernalized biennial plants) with a peak around 7 h after dawn both under LD (16 hours light/8 hours dark) and SD (8 hours light/16 hours dark) conditions. This experiment confirms the rhythmic and circadian expression of BvPRR7 as described for most of the clock-associated genes identified thus far (McClung, 2006).

Example 1.5

Allelic Variability and Association to the Vernalization Requirement

Using the primer pairs provided in Table 6, the entire coding region of the BvPRR7 gene as well as ±1.0 Kb of its promoter region were amplified and sequenced across a panel of biennial and annual accessions. This panel comprised 3 biennial elite lines from the Syngenta germplasm pool as well as annual and biennial wild and weed beets collected across Europe. The PCR conditions for the amplifications were as follows: primary denaturation at 95° C. for 5 min followed by 35 amplification cycles of 30 seconds at 95° C., 30 seconds at 60° C. and 30 seconds at 72° C. and followed by 5 min at 72° C. PCR experiments were run at a GeneAMP PCR System 9700 instrument from Applied Biosystems Inc. using Platinum Taq DNA polymerase and the corresponding reaction mix from Invitrogen Corporation as recommended by the supplier. The graphical representation of the observed genotypes shows several annual alleles and 2 biennial alleles (cf. Tables 7-1 and 7-2 also shown as (see also FIGS. 10 and 11, respectively). Several polymorphisms show a strong correlation between the allelic variation observed for BvPRR7 and the annual or biennial plant habit. This observation further strengthens the causal relationship between BvPRR7 and the B locus for vernalization independent flowering in sugar beet. Table 7-1 (FIG. 11) shows the polymorphisms identified in the promoter region when comparing the annual and biennial alleles. Plant lines having heterozygous forms of the allele were removed from the analysis. SNP positions indicated in the table are numbered in accordance to SEQ ID NO: 8. Nucleotide positions indicated by an asterisk (*) can be used for the discrimination of the annual and biennial alleles. As can be seen from Table 7-1 (FIG. 11), the SNPs at positions #11592, #12316, #12490 and #12544, respectively, of the promoter region can be used to distinguish all annual alleles from the biennial alleles. The polymorphisms identified in the coding region when comparing the annual and biennial alleles are shown in Table 7-2 (FIG. 12). Plant lines having heterozygous forms were again removed from the analysis. In Table 7-2 (FIG. 12) the SNP and amino acid positions are numbered in accordance to SEQ ID NOs: 9 and 11, respectively. Nucleotide and amino acid positions indicated by an asterisk (*) can be used for the discrimination of the annual and biennial alleles. Amongst the SNPs detected in the coding region, the SNPs at positions #224, #351, #615, #897, #1082, #1841, #1915, and #2334, respectively, can be used to distinguish all annual alleles from the biennial alleles. For the purpose of quality assurance, any one or a combination of more than one of the SNPs detected in the coding region as well as in the promoter region can be used for detecting the presence of the annual allele in commercial seed lots of biennial cultivars by means of molecular markers targeting this one or more SNP(s).

TABLE 6

Nucleotide sequences of primers used for the amplification and sequencing of the coding region as well as of ±1 Kb of the 5' UTR region of the BvPRR7 gene.

| primer ID | SEQ ID NO | sequence 5' | orientation | use in combination with | location on BvPRR7 |
|---|---|---|---|---|---|
| SELA3977 | 33 | CGTGTCGAATATTGATTTACTGAGATC | Forward | SELA3988 | 5' UTR |
| SELA3988 | 34 | TAACCCATCATGTCTTTTCAACAATC | Reverse | SELA3977 | 5' UTR |
| SELA4442 | 35 | AAGAATACCGAGAGTTTTTCCC | Forward | SELA3809 | 5' UTR |
| SELA3809 | 36 | TCACCAATTCTTTATATCATATCATGACA | Reverse | SELA4442 | 5' UTR |
| SELA3810 | 37 | GAGAAAAGGGTTTTAGATGGTAAGTTTT | Forward | SELA3807 | 5' UTR |
| SELA3807 | 38 | CATTTGTTGAAGTAGGTGATAAGGACAA | Reverse | SELA3810 | intron2 |
| SELA3766 | 39 | TTTGATGCTTTTTTCAGGCCA | Forward | SELA3769 | intron2 |
| SELA3769 | 40 | AATATGTGTGAGAAAATGGTGGCA | Reverse | SELA3766 | intron5 |
| SELA3857 | 41 | TCCATTTGAGGAGTAGGTATGATGAG | Forward | SELA3860 | intron5 |
| SELA3860 | 42 | TCTTGAGCTGCTGATCCACGT | Reverse | SELA3857 | exon8 |
| SELA3861 | 43 | CTGCATCTGGTAAGCCTGGTG | Forward | SELA3864 | exon8 |
| SELA3864 | 44 | AATGTGACCCGTAAACGCCT | Reverse | SELA3861 | 3' UTR |

TABLE 7-1

Haplotypes of BvPRR7 within different annual and biennial accesions (see also FIG. 11).

| sources lines phenotype | Spain BATRAN annual | Greece GRE1AN annual | Syngenta annual A610 annual | Italy ITALAN annual | Portugal PORTAN annual | USA USDA-62 annual | Italy I3B10A annual | Italy I3F02B annual | France F1A01RO annual | France F1A02RO annual | France F1D08TA annual | France F1D12TA annual |
|---|---|---|---|---|---|---|---|---|---|---|---|---|
| nucleotide pos. | | | | | | | | | | | | |
| 11360 | A | T | T | T | T | T | T | T | T | T | T | T |
| 11403 | - | G | G | G | G | G | G | G | G | G | G | G |
| 11404 | - | C | C | C | C | C | C | C | C | C | C | C |
| 11405 | - | G | G | G | G | G | G | G | G | G | G | G |
| 11408 | T | G | G | G | G | G | G | G | G | G | G | G |
| 11410 | A | G | G | G | G | G | G | G | G | G | G | G |
| 11411 | A | - | - | - | - | - | - | - | - | - | - | - |
| 11469 | - | - | - | - | - | - | - | - | - | - | - | T |
| 11476 | T | T | - | T | - | T | T | T | T | T | T | T |
| 11477 | G | G | - | G | - | G | G | G | G | G | G | G |
| 11478 | A | A | - | A | - | A | A | A | A | A | A | A |
| 11479 | A | A | - | A | - | A | A | A | A | A | A | A |
| 11480 | T | T | - | T | - | T | T | T | T | T | T | T |
| 11481 | G | G | - | G | - | G | G | G | G | G | G | G |
| 11482 | T | T | - | T | - | T | T | T | T | T | T | T |
| 11483 | G | G | - | G | - | G | G | G | G | G | G | G |
| 11487 | C | C | C | C | C | C | C | C | C | C | C | C |
| 11493 | - | C | C | C | C | C | C | C | C | C | C | C |
| 11494 | - | C | C | C | C | C | C | C | C | C | C | C |
| 11495 | - | A | A | A | A | A | A | A | A | A | A | A |
| 11503 | A | G | G | G | G | G | G | G | G | G | G | G |
| 11561 | A | - | - | - | - | - | - | - | - | - | - | - |
| 11562 | T | - | - | - | - | - | - | - | - | - | - | - |
| 11563 | T | - | - | - | - | - | - | - | - | - | - | - |
| 11564 | C | - | - | - | - | - | - | - | - | - | - | - |
| 11565 | T | - | - | - | - | - | - | - | - | - | - | - |
| 11566 | C | - | - | - | - | - | - | - | - | - | - | - |
| 11567 | A | - | - | - | - | - | - | - | - | - | - | - |
| 11568 | C | - | - | - | - | - | - | - | - | - | - | - |
| 11584 | A | T | T | T | T | T | T | T | T | T | T | T |
| 11592 | - | - | - | - | - | - | - | - | - | - | - | - |
| 11787 | A | A | A | A | A | A | A | A | A | A | A | A |
| 11828 | I | D | D | D | D | D | D | D | D | D | D | D |
| 11939 | A | - | - | - | - | - | - | - | - | - | - | - |
| 11948 | T | G | G | G | G | G | G | G | G | G | G | G |
| 11993 | - | T | T | T | T | T | T | T | T | T | T | T |
| 12211 | C | C | C | C | C | C | C | C | C | C | C | C |
| 12316 | A | A | A | A | A | A | A | A | A | A | A | A |
| 12325 | A | A | A | A | A | A | A | A | A | A | A | A |
| 12404 | - | - | - | - | - | - | - | - | - | - | - | - |
| 12438 | G | G | G | A | A | G | G | G | G | G | G | G |
| 12490 | A | A | A | A | A | A | A | A | A | A | A | A |
| 12512 | G | G | G | G | G | G | G | G | G | G | G | G |
| 12544 | T | T | T | T | T | T | T | T | T | T | T | T |

TABLE 7-1-continued

| sources lines phenotype | France F1E01TA annual | France F2C06SO annual | France F1H01BA annual | France F2B10VA annual | France F2C12SO annual | Italy I3D10A annual | UK U3A10GB biennial | Syngenta O-type O018 biennial | Syngenta P-1 P346 biennial | Syngenta P-2 P402 biennial | target |
|---|---|---|---|---|---|---|---|---|---|---|---|
| nucleotide pos. | | | | | | | | | | | |
| 11360 | T | T | T | T | T | T | A | A | A | A | |
| 11403 | G | G | G | G | G | G | - | - | - | - | |
| 11404 | C | C | C | C | C | C | - | - | - | - | |
| 11405 | G | G | G | G | G | G | - | - | - | - | |
| 11408 | G | G | G | G | G | G | C | C | C | C | |
| 11410 | G | G | G | G | G | G | A | A | A | A | |
| 11411 | - | - | - | - | - | - | A | A | A | A | |
| 11469 | T | T | - | - | - | - | - | - | - | - | |
| 11476 | T | T | T | T | T | T | T | T | T | T | |
| 11477 | G | G | G | G | G | G | G | G | G | G | |
| 11478 | A | A | A | A | A | A | A | A | A | A | |
| 11479 | A | A | A | A | A | A | A | A | A | A | |
| 11480 | T | T | T | T | T | T | T | T | T | T | |
| 11481 | G | G | G | G | G | G | A | A | A | A | |
| 11482 | T | T | T | T | T | T | T | T | T | T | |
| 11483 | G | G | G | G | G | G | G | G | G | G | |
| 11487 | C | C | T | T | T | C | C | C | C | C | |
| 11493 | C | C | C | C | C | C | - | - | - | - | |
| 11494 | C | C | C | C | C | C | - | - | - | - | |
| 11495 | A | A | A | A | A | A | - | - | - | - | |
| 11503 | G | G | G | G | G | G | A | A | A | A | |
| 11561 | - | - | - | - | - | - | A | A | A | A | |
| 11562 | - | - | - | - | - | - | T | T | T | T | |
| 11563 | - | - | - | - | - | - | T | T | T | T | |
| 11564 | - | - | - | - | - | - | C | C | C | C | |
| 11565 | - | - | - | - | - | - | T | T | T | T | |
| 11566 | - | - | - | - | - | - | C | C | C | C | |
| 11567 | - | - | - | - | - | - | A | A | A | A | |
| 11568 | - | - | - | - | - | - | C | C | C | C | |
| 11584 | T | T | T | T | T | T | A | A | A | A | |
| 11592 | - | - | - | - | - | - | A | A | A | A | * |
| 11787 | A | A | A | A | A | A | T | A | A | A | |
| 11828 | D | D | D | D | D | D | D | D | D | D | |
| 11939 | - | - | A | A | A | A | D | D | D | D | |
| 11948 | G | G | T | T | T | T | T | T | T | T | |
| 11993 | T | T | - | - | - | - | - | - | - | - | |
| 12211 | C | C | T | T | T | T | C | C | C | C | |
| 12316 | A | A | A | A | A | A | G | G | G | G | * |
| 12325 | A | A | A | A | A | T | A | A | A | A | |
| 12404 | - | - | - | - | - | G | - | - | - | - | |
| 12438 | G | G | G | G | G | G | G | G | G | G | |
| 12490 | A | A | A | A | A | A | G | G | G | G | * |
| 12512 | G | G | C | C | C | C | G | G | G | G | |
| 12544 | T | T | T | T | T | T | - | - | - | - | * |

TABLE 7-2

Haplotypes of BvPRR7 within different annual and biennial accessions. (see also FIG. 12)

| sources lines phenotype | Spain BATRAN annual | Greece GRE1AN annual | Syngenta annual A610 annual | Italy ITALAN annual | Portugal PORTAN annual | USA USDA-62 annual | Italy I3B10A annual | Italy I3F02B annual | France F1A01RO annual | France F1A02RO annual | France F1D08TA annual | France F1D12TA annual |
|---|---|---|---|---|---|---|---|---|---|---|---|---|
| nucleotide position | | | | | | | | | | | | |
| 92 | T | G | G | G | G | G | G | G | G | G | G | G |
| 224 | C | C | C | C | C | C | C | C | C | C | C | C |
| 351 | T | T | T | T | T | T | T | T | T | T | T | T |
| 615 | T | T | T | T | T | T | T | T | T | T | T | T |
| 724 | G | G | G | G | G | G | G | G | G | G | G | G |
| 749 | G | G | G | G | G | G | G | G | G | G | G | G |
| 845 | C | C | C | C | C | C | C | C | C | C | C | C |
| 897 | G | G | G | G | G | G | G | G | G | G | G | G |
| 986 | T | T | T | T | T | T | T | T | T | T | T | T |
| 1012 | C | T | C | C | C | C | C | C | C | C | C | C |
| 1082 | A | A | A | A | A | A | A | A | A | A | A | A |
| 1100 | A | C | C | C | C | C | C | C | C | C | C | C |
| 1157 | G | G | G | G | G | G | G | G | G | G | G | G |
| 1161 | T | T | T | A | A | T | T | T | T | T | T | T |
| 1253 | A | A | A | A | A | A | A | A | A | A | A | A |
| 1841 | G | G | G | G | G | G | G | G | G | G | G | G |
| 1874 | G | G | A | G | G | G | G | G | G | G | G | G |
| 1915 | T | T | T | T | T | T | T | T | T | T | T | T |
| 1981 | G | A | A | A | A | A | A | A | A | A | A | A |
| 2100 | T | T | T | T | T | T | T | T | T | T | T | T |
| 2104 | G | G | G | G | G | G | G | G | G | G | G | A |
| 2109 | A | A | A | A | A | A | A | A | A | A | A | A |
| 2125 | G | G | A | G | G | G | G | G | G | G | G | G |
| 2154 | A | A | A | A | A | A | A | A | A | A | A | A |
| 2155 | A | A | A | A | A | A | A | A | A | A | A | A |
| 2156 | G | G | G | G | G | G | G | G | G | G | G | G |
| 2157 | T | T | T | T | T | T | T | T | T | T | T | T |
| 2158 | G | G | G | G | G | G | G | G | G | G | G | G |
| 2159 | G | G | G | G | G | G | G | G | G | G | G | G |
| 2253 | T | T | T | T | T | T | T | T | T | T | T | T |
| 2334 | G | G | G | G | G | G | G | G | G | G | G | G |
| amino acid position | | | | | | | | | | | | |
| 31 | V | G | G | G | G | G | G | G | G | G | G | G |
| 75 | P | P | P | P | P | P | P | P | P | P | P | P |
| 117 | N | N | N | N | N | N | N | N | N | N | N | N |
| 242 | E | E | E | E | E | E | E | E | E | E | E | E |

TABLE 7-2-continued

| | | | | | | | | | | | | |
|---|---|---|---|---|---|---|---|---|---|---|---|---|
| 250 | S | S | S | S | S | S | S | S | S | S | S | S |
| 282 | A | A | A | A | A | A | A | A | A | A | A | A |
| 329 | V | V | V | V | V | V | V | V | V | V | V | V |
| 338 | P | S | P | P | P | P | P | P | P | P | P | P |
| 361 | K | K | K | K | K | K | K | K | K | K | K | K |
| 367 | N | T | T | T | T | T | T | T | T | T | T | T |
| 386 | S | S | S | S | S | S | S | S | S | S | S | S |
| 387 | F | F | F | L | L | F | F | F | F | F | F | F |
| 418 | H | H | H | H | H | H | H | H | H | H | H | H |
| 614 | R | R | R | R | R | R | R | R | R | R | R | R |
| 625 | S | S | N | S | S | S | S | S | S | S | S | S |
| 639 | S | S | S | S | S | S | S | S | S | S | S | S |
| 661 | E | K | K | K | K | K | K | K | K | K | K | K |
| 702 | G | G | G | G | G | G | G | G | G | G | G | R |
| 703 | I | I | I | I | I | I | I | I | I | I | I | I |
| 709 | A | A | T | A | A | A | A | A | A | A | A | A |
| 723 | S | S | S | S | S | S | S | S | S | S | S | S |
| 724 | G | G | G | G | G | G | G | G | G | G | G | G |

| sources | France | France | France | France | France | Italy | UK | Syngenta O-type | Syngenta P-1 | Syngenta P-2 | |
|---|---|---|---|---|---|---|---|---|---|---|---|
| lines | F1E01TA | F2C06SO | F1H01BA | F2B10VA | F2C12SO | I3D10A | U3A10GB | O018 | P346 | P402 | |
| phenotype | annual | annual | annual | annual | annual | annual | biennial | biennial | biennial | biennial | target |
| nucleotide position | | | | | | | | | | | |
| 92 | G | G | G | G | G | G | G | G | G | G | |
| 224 | C | C | C | C | C | C | A | A | A | A | * |
| 351 | T | T | T | T | T | T | A | A | A | A | * |
| 615 | T | T | T | T | T | T | C | C | C | C | * |
| 724 | G | G | A | A | A | G | G | G | G | G | |
| 749 | G | G | G | G | G | G | G | T | T | T | |
| 845 | C | C | C | C | C | C | T | C | C | C | |
| 897 | G | G | G | G | G | G | A | A | A | A | * |
| 986 | T | T | T | T | T | G | G | G | G | G | |
| 1012 | C | C | C | C | C | C | C | C | C | C | * |
| 1082 | A | A | A | A | A | A | C | C | C | C | |
| 1100 | C | C | C | C | C | C | C | C | C | C | |
| 1157 | G | G | T | T | T | G | G | G | G | G | |
| 1161 | T | T | T | T | T | T | T | T | T | T | |
| 1253 | A | A | A | A | A | A | A | G | G | G | * |

TABLE 7-2-continued

| | 1 | 2 | 3 | 4 | 5 | 6 | 7 | 8 | 9 | 10 | |
|---|---|---|---|---|---|---|---|---|---|---|---|
| 1841 | G | G | G | G | G | G | A | A | A | A | |
| 1874 | G | G | G | G | G | G | G | G | G | G | * |
| 1915 | T | T | T | T | T | T | C | C | C | C | |
| 1981 | A | A | G | G | G | G | G | G | G | G | |
| 2100 | T | T | T | T | T | C | T | T | T | T | |
| 2104 | A | A | G | G | G | G | G | G | G | G | |
| 2109 | A | A | A | A | A | G | A | A | A | A | |
| 2125 | G | G | G | G | G | G | G | G | G | G | |
| 2154 | A | A | A | A | A | A | - | A | A | A | |
| 2155 | A | A | A | A | A | A | - | A | A | A | |
| 2156 | G | G | G | G | G | G | - | G | G | G | |
| 2157 | T | T | T | T | T | T | - | T | T | T | |
| 2158 | G | G | G | G | G | G | - | G | G | G | |
| 2159 | G | G | G | G | G | G | - | G | G | G | |
| 2253 | T | T | C | C | C | T | T | T | T | T | |
| 2334 | G | G | G | G | G | G | A | A | A | A | * |
| amino acid position | | | | | | | | | | | |
| 31 | G | G | G | G | G | G | G | G | G | G | |
| 75 | P | P | P | P | P | P | H | H | H | H | * |
| 117 | N | N | N | N | N | N | K | K | K | K | * |
| 242 | E | E | K | K | K | E | E | E | E | E | |
| 250 | S | S | S | S | S | S | S | I | I | I | |
| 282 | A | A | A | A | A | A | V | A | A | A | |
| 329 | V | V | V | V | V | G | G | G | G | G | |
| 338 | P | P | P | P | P | P | P | P | P | P | |
| 361 | K | K | K | K | K | K | T | T | T | T | * |
| 367 | T | T | T | T | T | T | T | T | T | T | |
| 386 | S | S | I | I | I | S | S | S | S | S | |
| 387 | F | F | F | F | F | F | F | F | F | F | |
| 418 | H | H | H | H | H | H | R | R | R | R | |
| 614 | R | R | R | R | R | R | H | H | H | H | * |
| 625 | S | S | S | S | S | S | S | S | S | S | |
| 639 | S | S | S | S | S | S | P | P | P | P | * |
| 661 | K | K | E | E | E | E | E | E | E | E | |
| 702 | R | R | G | G | G | G | G | G | G | G | |
| 703 | I | I | I | I | I | M | I | I | I | I | |
| 709 | A | A | A | A | A | A | A | A | A | A | |
| 723 | S | S | S | S | S | S | - | S | S | S | |
| 724 | G | G | G | G | G | G | - | G | G | G | |

Example 1.6

Allelic Discrimination Between Annual and Biennial Sugar Beet Plants

The presence of 'bolters', i.e. sugar beet plants carrying the annual B allele, in commercial seed lots due to the influx of annual pollen during the hybrid seed production, represents a major quality parameter in the production and marketing of sugar beet. For quality control in seed production it is thus important to have a means allowing to distinguish between annual and biennial plants.

For allelic discrimination DNA is isolated from plants or seeds to be tested by employing conventional DNA isolation methods. The DNA is then tested in a TaqMan® assay targeting SNP at position #2334 in the coding region. The nucleotide sequences used in this assay were as follow: PRR7(T6)-F: 5'-GCTATCGGTATTCCTTCCTTTGTTT-3' (SEQ ID NO: 49), PRR7(T6)-R: 5'-CTCGTGTTCGTGGGCAATT-3' (SEQ ID NO: 50), PRR7(T6)-VIC: 5'-VIC-CTCGTACCTG-GCGCAC-MGB-NFQ-3' (SEQ ID NO: 51) and PRR7(T6)-FAM: 5'-FAM-CTCGCACCTGGCGCAC-MGB-NFQ-3' (SEQ ID NO: 52). The PCR reaction further consisted of the TaqMan® Universal PCR Master Mix and No AmpErase® UNG (2×) from Applied Biosystems Inc. according to the manufacturer's recommendations. The PCR amplification was performed as follows: 95° C. for 10 min followed by 40 cycles of 95° C. for 15 sec and 60° C. for 1 min, using a Real Time PCR 7500 System instrument. EndPoint measurement was performed using the Sequence Detection System 2.0 software. If the analysis shows a substantial increase in VIC dye fluorescence only, this indicates homozygosity for Allele X (i.e. homozygosity for the biennial allele). Substantial increase in FAM dye fluorescence only indicates homozygosity for Allele Y (i.e. homozygosity for the annual allele). If both fluorescent signals are substantially increased, the plant is heterozygous (i.e. an annual plant with heterozygosity for the B locus).

FIG. 9 shows the result of an allelic discrimination assay of a set of annual and biennial individual plants.

Nucleotide sequences can be similarly used in this assay and provide similar results (i.e., which allow to discriminate between annual and biennial individual plants) are as follow: 1r22(T1)-F: 5'-GATAAATTCTGACCCGCATCACA-3' (SEQ ID NO: 55), 1r22(T1)-R: 5'-GGACTGAGT-TGATAATAATCAACTTTCC-3' (SEQ ID NO: 56), 1r22(T1)-VIC: 5'-VIC-CTAGCGCAATTTC-MGB-NFQ-3' (SEQ ID NO: 57) and 1r22(T1)-FAM: 5'-FAM-AGCTAGCGCCCAATT-MGB-NFQ-3' (SEQ ID NO: 58).

Example 2

Transgenic Validation of BvPRR7 by Means of a Complementation Study

The annual plant habit conferred by the B gene behaves as a single dominant trait; the requirement for vernalization in biennial plants accordingly is recessive. The transformation of an annual allele of BvPRR7 into a biennial genotype thus is predicted to bestow the annual flowering behavior onto the biennial acceptor genotype. There should thus be no need to vernalize the transgenic plants to induce bolting as the transformed annual allele of BvPRR7 is supposed to overrule the need for vernalization conferring the annual habit. To verify this hypothesis, the coding sequence of an annual allele of BvPRR7 under the control of an annual promoter together with a terminator fragment was transformed into biennial genotype G018. The plasmid map of the binary vector carrying the gene cassettes for both the PMI selectable marker gene and the annual BvPRR7 allele is shown in FIG. 10. The experimental procedure used for the transformation of sugar beet was essentially as disclosed by Chang et al., 2002 using sugar beet meristems as explant material and the phosphomannose isomerase (PMI) gene as selectable marker. SEQ ID NO: 53 depicts the nucleotide sequence of the coding region of the annual PRR7 allele (nucleotides 1306 to 3672 of SEQ ID NO: 49) downstream of 1,3 kb of its promoter region (nucleotides 1 to 1305 of SEQ ID NO: 49). Transgenic shoots were checked for PMI activity (Joersbo et al., 1998) and subsequently rooted, potted in soil and transferred to the greenhouse. Negative controls consisted of shoots of both non-transgenic annual and biennial sugar beet plants that underwent the same in vitro regeneration procedure, but without Agrobacterium infection and mannose selection. Plants were grown in growth chambers at a constant temperature of 18° C. and a photoperiod of 17 hours light and 7 hours dark.

Under these conditions (without induction of bolting by applying cold temperatures) the non-transgenic biennial controls do not show any signs of bolting within an observation period of up to 12 weeks, whereas the annual control plants start to bolt normally within 6 to 8 weeks. Contrary to the non-transgenic biennial control plants, a substantial number of transgenic events starts bolting within four to ten weeks and basically behaves as annual plants despite their biennial genetic background. Transgenic plants that bolted and flowered are cross-pollinated with a biennial maintainer line to produce offspring. Progeny plants are tested for PMI activity and subsequently monitored for bolting and flowering without vernalization. These progeny plants show a one to one segregation ratio and a perfect correlation between PMI activity and the annual habit. These data confirm the causal relationship between BvPRR7 and vernalization-independent flowering in sugar beet.

Example 3

Transgenic Suppression of BvPRR7 Confers Bolting Resistance

Since BvPRR7 plays a key role in the vernalization response in sugar beet, BvPRR7 represents an obvious candidate for engineering bolting resistance by suppressing the vernalization response. For this purpose a BvPRR7 cDNA fragment of 0.6 Kb (SEQ ID NO: 1) was assembled into an RNAi cassette under the control of the constitutive Ubi3 promoter from Arabidopsis (Norris et al., 1993). The inverted repeat of the BvPRR7 fragment is separated by the second intron from the potato StLS1 gene (Eckes et al., 1986; Vancanneyt et al., 1990) to stabilize the RNAi cassette, but also to improve the efficiency of the RNAi phenomenon (Wang and Waterhouse, 2001; Smith et al., 2000). The plasmid map of the binary vector carrying the RNAi gene cassette for BvPRR7 and the PMI selectable marker gene is shown in FIG. 10. The RNAi cassette was transformed into the biennial genotype G018 and selection for PMI-positive shoots was carried out as described in the previous example. PMI-positive shoots and non-transgenic controls were rooted and transferred to the greenhouse for an acclimatization period of two weeks minimum at 18° C. prior to the vernalization treatment. Once well-established, the transgenic plants were exposed to the vernalization treatment consisting of a period of 14 weeks at a constant temperature of 6° C. and 12 hours low artificial light. Prior to applying bolting-inductive conditions, vernalized plants were slowly acclimatized for two weeks in climate chambers by stepwise increasing the temperature from 10 to 18° C. Plants were subsequently repotted into to larger pots (2 liter), and monitored for bolting while exposed to a constant temperature of 18° C. and a long-day photoperiod of 17 hours light/7 hours dark. Non-transgenic control plants started bolting between four to six weeks post vernalization. Transgenic plants suppressed for BvPRR7 frequently showed a delay in bolting ranging from only two weeks to more than two months. A few events did not show any bolting behavior at all under the conditions applied in the greenhouse. Apart from the delay in bolting and flowering, transgenic plants developed normally and showed no phenotypic aberrations. In general, plants delayed in bolting show a higher leaf number at the time of bolting as a result of the prolonged vegetative stage.

REFERENCES

Abe J., Guan G.-P. and Shimamoto Y., 1997. A gene complex for annual habit in sugar beet (Beta vulgaris L.). Euphytica 94: 129-135.

Barany F., 1991. Genetic Disease Detection and DNA Amplification Using Cloned Thermostable Ligase. Proc. Natl. Acad. Sci. USA, 88:189-93.

Batzer M. A., Carlton J. E. and Deininger P. L., 1991. Enhanced evolutionary PCR using oligonucleotides with inosine at the 3'-terminus. Nucleic Acids Res. 19:5081.

Beales J., Turner A., Griffiths S., Snape J. W. and Laurie D. A., 2007. A Pseudo-Response Regulator is misexpressed in the photoperiod insensitive Ppd-D1a mutant of wheat (Triticum aestivum L.). Theor. Appl. Genet. 115: 721-733.

Botstein D., White R. L., Skolnick M. and Davis R. W., 1980. Construction of genetic linkage map in man using restriction length polymorphisms. Am. J. Hum. Genet., 32: 314-331.

Brunke K. J. and Wilson S. L., 1993. Brassica hsp80 promoter. EP0559603

Chang Y.-F., Zhou H., Dunder E. M., Rouse S. N., Gu W. and Boutreau E., 2002. Methods for stable transformation of plants. WO 02/14523

Chiapparino E., Lee D. and Donini P., 2004. Genotyping single nucleotide polymorphisms in barley by tetra-primer ARMS-PCR. Genome 47:414-420.

Cooper D. N., Smith B. A., Cooke H. J. et al., 1985. An estimate of unique DNA sequence heterozygosity in the human genome. Hum. Genet. 69:201-205.

Eckes P., Rosahl S., Schell J. and Willmitzer L., 1986. Isolation and characterization of a light-inducible, organ-specific gene from potato and analysis of its expression after tagging and transfer into tobacco and potato shoots. Mol Gen Genet 205, 14-22.

English J. J., Mueller E. and Baulcombe D. C., 1996. Suppression of virus accumulation in transgenic plants exhibiting silencing of nuclear genes. Plant Cell 8:179-188.

Fan J. B., Oliphant A., Shen R., Kermani B. G., Garcia F., Gunderson K. L., Hansen M., et al., 2003. Highly parallel SNP genotyping. Cold Spring Harb Symp Quant Biol 68:69-78.

Felsenstein J., 1985. Confidence limits on phylogenies: An approach using the bootstrap. Evolution 39:783-791.

Gaafar R. M., Hohmann U. and Jung C., 2005. Bacterial artificial chromosome-derived molecular markers for early bolting in sugar beet. Theor. Appl. Genet. 110, Number 6: 1027-1037.

Imaizumi T. and Kay S. A., 2006. Photoperiodic control of flowering: not only by coincidence. Trends Plant Science 11: 550-557.

Joersbo M., Donaldson I., Kreiberg K., Petersen S. G., Brunstedt J. and Okkels F. T., 1998. Analysis of mannose selection used for transformation of sugar beet. Mol Breeding 4:111-117.

Konieczny A. and Ausubel F. M., 1993. A procedure for mapping *Arabidopsis* mutations using co-dominant ecotype-specific PCR-based markers, Plant J. 4, pp. 403-410.

Kwok P. Y., Deng Q., Zakeri H., Taylor S. L. and Nickerson D. A., 1996. Increasing the information content of STS-based genome maps: Identifying polymorphisms in mapped STSs. Genomics 31: 123-126.

Landegren U., Kaiser R., Sanders J. and Hood L., 1988. A ligase-mediated gene detection technique. Science 241 4869, pp. 1077-1080.

Litt M. and Luty J. A., 1989. Hypervariable microsatellite revealed by in-vitro amplification of a dinucleotide repeat in the cardiac muscle actin gene. Am J Hum Genet 44: 397-401.

McClung C. R., 2006. Plant circadian rhythms. Plant Cell 18: 792-803.

McGrath J. M., Shaw R. S., de los Reyes B. G. and Weiland J. J., 2004. Construction of a Sugar Beet BAC Library from a Hybrid with diverse Traits. Plant Mol Biol Rep 22: 23-28.

Michaels S. D. and Amasino R. M., 1998. A robust method for detecting single-nucleotide changes as polymorphic markers by PCR. The Plant Journal 14(3): 381-385.

Möhring S., Salamini F. and Schneider K., 2005. Multiplexed, linkage group-specific SNP marker sets for rapid genetic mapping and fingerprinting of sugar beet (*Beta vulgaris* L.). Molecular Breeding, Volume 14, Number 4: 475-488.

Mullis K. B., Faloona F. A., Scharf S., Saiki R., Horn G. and Erlich H., 1986. Specific enzymatic amplification of DNA in vitro: the polymerase chain reaction. Cold Spring Harbor Symp Quant Biol 51:263-273.

Nakamichi N., Kita M., Ito S., Sato E., Yamashino T. and Mizuno T., 2005. PSEUDO-RESPONSE REGULATORS, PRR9, PRR7 and PRR5, together play essential roles close to the circadian clock of *Arabidopsis thaliana*. Plant Cell Physiol., 46: 686-698.

Neff M. M., Neff J. D., Chory J. and Pepper A. E., 1998. dCAPS, a simple technique for the genetic analysis of single nucleotide polymorphisms: experimental applications in *Arabidopsis thaliana* genetics. Plant J 14: 387-392.

Nickerson D. A., Kaiser R., Lappin S., Stewart J., Hood L. and Landegren U., 1990. Automated DNA diagnostics using an ELISA-based oligonucleotide ligation assay. Proc. Natl. Acad. Sci. USA. 1990 November; 87(22):8923-7.

Norris S. R., Meyer S. E. and Callis J., 1993. The intron of *Arabidopsis thaliana* polyubiquitin genes is conserved in location and is a quantitative determinant of chimeric gene expression. Plant Mol Biol 21: 895-906.

Ohtsuka E., Matsuki S., Ikehara M., Takahashi Y. and Matsubara K., 1985. An alternative approach to deoxyoligonucleotides as hybridization probes by insertion of deoxyinosine at ambiguous codon positions, J. Biol. Chem. 260 (5):2605-2608.

Okamuro J. K. and Goldberg R. B., 1989. Regulation of Plant Gene Expression: General Principles. Biochemistry of Plants, vol. 15:1-82.

Orita M., Suzuki Y., Sekiya T. and Hayashi K., 1989. Rapid and sensitive detection of point mutations and DNA polymorphism using he polymerase chain reaction. Genomics 5:874-879.

Pearson W. R., 1990. Rapid and Sensitive Sequence Comparison with FASTP and FASTA. Methods in Enzymology 183, 63-98.

Rossolini G. M., Cresti S., Ingianni A., Cattani P., Riccio M. L. and Satta G., 1994. Use of deoxyinosine-containing primers vs degenerate primers for polymerase chain reaction based on ambiguous sequence information, Mol. Cell Probes 8 (1994), pp. 91-98.

Ruiz M. T., Voinnet O. and Baulcombe D. C., 1998. Initiation and maintenance of virus-induced gene silencing. Plant Cell 10, 937-946.

Salomé P. A. and McClung C. R., 2005. PSEUDO-RESPONSE REGULATOR 7 and 9 are partially redundant genes essential for the temperature responsiveness of the *Arabidopsis* circadian clock. Plant Cell 17: 791-803.

Saitou N. and Nei M., 1987. The neighbor-joining method: A new method for reconstructing phylogenetic trees. Molecular Biology and Evolution 4:406-425.

Segev D., 1990. PCT Pub. No. WO 90/01069.

Smith N. A., Singh S. P., Wang M. B., Stoutjesdijk P. A. Green A. G. and Waterhouse P. M., 2000. Total silencing by intron-spliced hairpin RNAs. Nature 407: 319-320.

Smith T. F. and Waterman M. S., 1981. Advances in Applied Mathematics. 2, 482-489.

Tamura K., Dudley J., Nei M. and Kumar S., 2007. MEGA4: Molecular Evolutionary Genetics Analysis (MEGA) software version 4.0. Molecular Biology and Evolution 24:1596-1599.

Thiel T., Kota R., Grosse I., Stein N. and Graner A., 2004. SNP2CAPS: a SNP and INDEL analysis tool for CAPS marker development. Nucleic Acids Res 32(1): e5.

Tijssen P., 1993. Laboratory Techniques in Biochemistry and Molecular Biology-Hybridization with Nucleic Acid Probes part I chapter 2 "Overview of principles of hybridization and the strategy of nucleic acid probe assays" Elsevier, New York.

Turner A., Beales J., Faure S., Dunford R. P. and Laurie D. A., 2005. The Pseudo-Response Regulator Ppd-H1 provides adaptation to photoperiod in barley. Science 310: 1031-1034.

Vancanneyt G., Schmidt R., O'Connor-Sanchez A., Willmitzer L. and Rocha-Sosa M., 1990. Construction of an intron-containing marker gene: Splicing of the intron in transgenic plants and its use in monitoring early events in *Agrobacterium*-mediated plant transformation. Mol. Gen. Genet. 220: 245-250.

Vandesompele J., De Preter K., Pattyn F., Poppe B, Van Roy N., De Paepe A. and Speleman F., 2002. Accurate normalization of real-time quantitative RT-PCR data by geometric averaging of multiple internal control genes. Genome Biology 3: 1-11.

Vos P., Hogers R., Bleeker M., et al. 1995. AFLP: a new technique for DNA fingerprinting. Nucleic Acids Research 23(21):4407-4414.

Wang D. G., Fan J. B., Siao C. J. et al., 1998. Large-scale identification, mapping, and genotyping of single-nucleotide polymorphisms in the human genome. Science 15, 1077-82.

Wang M. B. and Waterhouse P. M., 2001. Application of gene silencing in plants. Curr. Opin. Plant Biol 5:124-150.

Weber J. L. and May P. E., 1989. Abundant class of human DNA polymorhisms which can be typed using the polymerare chain reaction. Am. J. Hum. Genet. 44,388-396.

Welsh J. and McCleland M., 1990. Fingerprinting genomes using PCR with arbitrary primers. Nucleic Acids Research 18 (24):7213-7218.

Wu D. Y. and Wallace R. B., 1989. Genomics 4:560-569.

Ye S., Dhillon S., Ke X., Collins A. R. and Day I. N., 2001. An efficient procedure for genotyping single nucleotide polymorphisms. Nucleic Acids Res., 29, E88-E88.

Zhou Y., Sun X.-D. and Ni M., 2007. Timing of photoperiodic flowering: light perception and circadian clock. J. Integrative Plant Biol. 49: 28-34.

Zuckerkandl E. and Pauling L., 1965. Evolutionary divergence and convergence in proteins, pp. 97-166 in Evolving Genes and Proteins, edited by V. Bryson and H. J. Vogel. Academic Press, New York.

The invention claimed is:

1. An expression cassette comprising a chimeric gene comprising the nucleic acid sequence as set forth in SEQ ID NO: 54 that is operably linked to a heterologous regulatory element which is functional in plants.

2. The expression cassette according to claim 1, wherein said expression cassette is comprising a nucleic acid molecule sequence encoding a dsRNA which is capable of targeting mRNA produced by transcription of the DNA sequence encoding the B protein for degradation.

3. A plant transformation vector and/or plant expression vector comprising the expression cassette of claim 1.

4. A transgenic sugar beet plant having a phenotype of delayed bolting, or cells, tissues or seeds thereof, each comprising the plant transformation vector of claim 3, wherein said transgenic sugar beet plant exhibits a phenotype of delayed bolting.

5. A method of transforming sugar beet plants, comprising utilizing the expression cassette of claim 1.

6. A plant cell comprising an expression cassette of claim 2.

* * * * *

```
                       SEQUENCE LISTING

<160> NUMBER OF SEQ ID NOS: 58

<210> SEQ ID NO 1
<211> LENGTH: 840
<212> TYPE: DNA
<213> ORGANISM: Beta vulgaris

<400> SEQUENCE: 1
gctcctgtca ttatgatgtc atctcatgat tcgatgggtt tagtcttaaa gtgcttatcc      60
aagggcgctg ttgactttct ggtgaagcct ataagaaaaa acgaacttaa aaacctttgg     120
cagcatgttt ggaggaggtg tcacagttct agtggtagtg gaagtgaaag ctgtgtaagg     180
aatggaaaat ccataggaag caagagggct gaagagtcgg acaatgacac tgacatcaat     240
gaggaagatg ataacagaag cattggttta caagctcggg atggaagtga caatggaagt     300
gggacccaga gttcatggac aaaaagggct gcagaagttg agagccccca accacagtct     360
acatgggagc aagcaactga tccacctgat agcacttgtg ctcaggtcat ttatccaatg     420
tctgaggcat ttgccagcag ctggatgcct ggatccatgc aggaacttga tggacaggat     480
catcaatatg acaatgtccc aatgggaaag gatttggaga ttggagtacc tagaatttca     540
gattcacggc taaatggacc aaacaaaacg gttaagttag caactactgc tgaggaaaac     600
caatattcac agttagacct caaccaggaa aatgatggtc gaagttttga tgaagagaac     660
ctggagatga ataatgataa acctaaaagt gagtggatta acaggctat gaactcacca      720 ggaaaagttg aagaacatcg tagaggaaat aaagtatctg atgcaccacc cgaaatttca     780
aaataaagga caaaggcatg caacatgtcg aggatatgcc ttctcttgtg ctcagtctga     840

<210> SEQ ID NO 2
<211> LENGTH: 23
<212> TYPE: DNA
<213> ORGANISM: Artificial
<220> FEATURE:
<223> OTHER INFORMATION: oliginucleotide sequence - Primer PRR7-F

<400> SEQUENCE: 2
atgtcatctc atgattcgat ggg                                              23

<210> SEQ ID NO 3
<211> LENGTH: 21
<212> TYPE: DNA
<213> ORGANISM: Artificial
<220> FEATURE:
<223> OTHER INFORMATION: Oligonucleotide sequence - Primer PRR7-R

<400> SEQUENCE: 3
tcagccctct tgcttcctat g                                                21

<210> SEQ ID NO 4
<211> LENGTH: 493
<212> TYPE: DNA
<213> ORGANISM: Beta vulgaris
```

<400> SEQUENCE: 4

```
atgtcatctc atgattcgat gggtttagtc ttaaagtgct tatccaaggg cgctgttgac      60
tttctggtga agcctataag aaaaaatgaa cttaaaaacc tttggcagca tgtttggagg     120
aggtgtcaca gtgtaagtgt ctttacattt tccagctttt catcagctta gtggttcgtg     180
tagcagtctt tcagattttc gaactttcta gcacatatga caaattaaac ctgcatgcta     240
attcccgatt agataatgga ataagctctt tcagctggtc ttttacttct ttctcttctc     300
ctcttatgaa aaactggtat gccactatgc atcttgttcc aggtgtttgt ttagtgtttc     360
tttcctttat tcgtttttttt gttttttattt ttaattttaa ttttaattttt tcctcattct     420
tttttttagtc tagtggtagt ggaagtgaaa gctgtgtaag gaatggaaaa tccataggaa     480
gcaagagggc tga                                                        493
```

<210> SEQ ID NO 5
<211> LENGTH: 493
<212> TYPE: DNA
<213> ORGANISM: Beta vulgaris

<400> SEQUENCE: 5

```
atgtcatctc atgattcgat gggtttagtc ttaaagtgct tatccaaggg cgctgttgac      60
tttctggtga agcctataag aaaaaatgaa cttaaaaacc tttggcagca tgtttggagg     120
aggtgtcaca gtgtaagtgt ctttacattt tccagctttt catcagctta gtggttcgtg     180
tagcagtctt tcaaattttc gaactttcta gcacatatga caaattaaac ctgcatgcta     240
attcccgatt agataatgga ataagctctt tcagctggtc ttttacttct ttctcttctc     300
ctcttatgaa aaactggtat gccactatgc atcttgttcc aggtgtttgt ttagtgtttc     360
tttcctttat tcgtttttttt gttttttattt ttaattttaa ttttagttttt tcctcattct     420
tttttttagtc tagtggtagt ggaagtgaaa gctgtgtaag gaatggaaaa tccataggaa     480
gcaagagggc tga                                                        493
```

<210> SEQ ID NO 6
<211> LENGTH: 493
<212> TYPE: DNA
<213> ORGANISM: Beta vulgaris

<400> SEQUENCE: 6

```
atgtcatctc atgattcgat gggtttagtc ttaaagtgct tatccaaggg cgctgttgac      60
tttctggtga agcctataag aaaaaaygaa cttaaaaacc tttggcagca tgtttggagg     120
aggtgtcaca gtgtaagtgt ctttacattt tccagctttty catcagctta gtggttcgtg     180
tagcagtctt tcaratttc gaactttcta gcacatatga caaattaaac ctgcatgcta     240
attcccgatt agataatgga ataagctctt tcagctggtc ttttacttct ttctcttctc     300
ctcttatgaa aaactggtat gccactatgc atcttgttcc aggtgtttgt ttagtgtttc     360
tttcctttat tcgtttttttt gttttttattt ttaattttaa ttttarttttt tcctcattct     420
tttttttagtc tagtggtagt ggaagtgaaa gctgtgtaag gaatggaaaa tccataggaa     480
gcaagagggc tga                                                        493
```

<210> SEQ ID NO 7
<211> LENGTH: 15037
<212> TYPE: DNA
<213> ORGANISM: Beta vulgaris

<400> SEQUENCE: 7

```
attattgtac atayawgacy atttacgtaa ctaaattaaa aaaagtttta aaaatgcaaa      60
acagaaaata aaatcaaata tcgacatttg gaaatttata atagaaatga ataaaaataa     120
gggagaaata aatgaagaac aaaataaatg agaaagagaa ttaaaatggt tcttgaaaaa     180
taaatgagag agaaaaggag ggaatgagtg agtgatgaga gagaaagagc tggcccactt     240
tcaaaaattc tgccaaaagc ctgccaaatt ttggccctcc taaaagcatc aaaactacgt     300
agttttggcc aaggtgtagg atgctcatcc tacacctccg tgcaggatct aaattgcgct     360
tagaaatagg gtctcctaat atttctctac tagcatttt tgcacgcgat gcgtgcttga     420
atttttttca agatagaaac tcgattttt tcgacgtatg taaaagtcaa aatttaaaca     480
ttagacatac aaagtataat tgttttagt tacaaaattt aattggttta gtctctgtaa     540
cttgagtttc tcaccagtct tttttttttt tttttttttt tttactttca aagttaaatt     600
ctatgaacaa aatagaaatt ttattgaatt tatctatgat ttctaatatt actccctccg     660
acccaaaata tagttcccat ttccctttt tcacggtaat ttatgcaaat agaatataag     720
agggatagta aagatttttt gtttatttaa ataaatgttg tatgggaaaa gatgatttta     780
ggagagaaag tagagaataa ttggtgaaag agtattaatt gtaacatttt ggttgaataa     840
acaaaggaaa aaacaaaatt caagaagcaa ataaatgaga attgtttcct tgaataatgc     900
aaaagtgggt tttaattccc aaaatatgcc caaaaataaa aaaattccct gtgtaccgtc     960
cacgtaagac ggcacgcgag attttttttt cctacttcaa tacaaccgct acttaaagta    1020
gcggtttact gatttttttt tttatctact taggtaaaac cttggcgctg agtgatataa    1080
ctcgctactt caagtagcga tttactgaaa tccccaactc catagtttga tatgtgcttg    1140
caacattttg cccaggtaaa ccgctactca gggtagcggt ttatgtgtat aaaccgctac    1200
ttaaagtagc ggtttatttt aatataaacc actattgtga gtagcggttt acgtgggcaa    1260
aaacaaaaaa aaaaatagtt tctcgcgtgt cgtcctacgt ggacggtacg cagggaattt    1320
tttaattttt gggcatattt tgggaactaa aacccacttt tgcattattc aaggaaaaaa    1380
ttcaaataaa tgatgggaca cggttttct agacaaatta cgaaaaaatg tggaactaaa    1440
tatgaaaatg gaaactatat tttgggacac ccaaaatgga aatgggaatt atattttggg    1500
acggagggag tataattttt tagttgattt ttgaattaag tatactactt catatattgt    1560
taagaaactg gacacttgga tttcaagtca aattttgtg agtatgtatt gacgttgtag    1620
tgtattggtt gtagtttgta agttaatttt tgttttgta aagttactc atttgagtga    1680
tttgtataat gtaaattatg caattctatg attttagttg acttgtgagt gattgttata    1740
attttatttc catatttttt atttgaatct ccctttggtt tgtatgtgaa tttgtaattt    1800
agaaaggcaa agggtaaaa tagtctcttc attcgggaac accatagttc ccctccttcc    1860
cttatataat aaagatgatg atgattttg ataataatga tttgtaagtg aattatgtga    1920
atgttttgt atgtattgac gtcctagtat attagtttta gtttgtaagt taatttttt    1980
gtttttgtaa agtttcccga tcatttgagt gattttcgtg atttttgtg attttctcaa    2040
ttctatgagt gatttgtaaa gtttcttgat ataagtgatt tctgagtggt gttgaattaa    2100
tttccggtgg ctttgttaga accccatttt agtattgaca tttctttgt aatttagaaa    2160
gggaaagggg ggtaaaatag gcatttcaaa aaaggacacc attgctcccc ccttcccttta    2220
tgtaattgag atatcttaaa agaataccga gagtttttc ccataaagga gtattttttt    2280
taaaattttt tccataaagg agtattat agtaccaagt tgatttccca aatcattatc    2340
```

```
cttgcgcaaa ttgcataatg gagatatttg gtgttgacgt gtgaatatgg ggccataata    2400
ataggaggtc aaaaacaaaa ctacaagggt taaaatcgtc acaatattaa acaagcatct    2460
cacattctca ctggtcactt tttttaacc tattaaaaga acaaacctttt aactctcctc    2520 acaatctgac acgtgtcgaa tattgattta ctgagatcaa tttagatcct ctcccttaga    2580
ctcttctgtc ttctcagtac agctttagat ctcaacctcc atgtcagcaa agttaccta    2640 cgtgtcatcc tacgtggcct ctccttctac ccctcactcc tccacgtcaa cattttcctc    2700
caaaattaaa aaatcatttt tttattatat ttacttgaat gtatataata atgtctactg    2760
atcttcttct ttagaactat ctccttctct cattggaacc tcaaaatcat tcttatttta    2820
tttcgagaaa aggaaaaaaa agcacatctt ttttgaagat taatttgtgg attattattg    2880
agcttcatcg tattaaaaaa catagtaaaa gttctttcct catttgtctt tttattcatc    2940 taatttttttt tagtgaagaa ccctaatttt gtttgtgaat tctcaagttc aagttttgat    3000 ttgggtatttt tttttgatga aatttgtgca gctgtaggat gttatcgtgc tgagaaaagg    3060
gttttagatg gtaagttttt ttttctttga tttctctctc ctactttttt ttttgttttg    3120
ctttagataa tactgtcatg atatgatata aagaattggt gatttgggta gtttatttaa    3180
cctatgatta tgtgttatttt gttttgatct ttcaatttat ctggtgctgt gtgtatatat    3240
gttttgtttt tcttcaagta tttggttatt attgaagtgg gtaattagga atttgctact    3300
aatctatgga tttgggttct gttgtgatta atttactata gatttgaggt ttaatttatg    3360
ttttataggt tagaaaagga aatcaatgat ttgtttgtgg atttgagtag attgtttgtt    3420
agtgtgtgta tgatgatatt aacttccatt attcttcccc aaattagggg taattgatgg    3480
ttttttgcat accgaaggcg tattctcttt gatgatggag tgattgttga aaagacatga    3540
tgggttaaag ttgcaggatt atttcatttc aataaacata attgatcaat ttggatctgt    3600
tgaatgaggt tgattcacaa aaatgaagat gggcccggtg ttgccaagtc ggtggcagag    3660
cttaatcaac atatagttgc tgtgaaaaaa gaaggtaggg gtagggttgc aggtgaaggg    3720
caggggcttt ccgaggagga cgaactgaga attattgagg atggtgaaga tgcaaacagc    3780
aggcgttctt tgagttctgt tcagcttcca gttcatactc acaggcatca gccacaagta    3840 caacccccagg ggagagtctg ttgggagagg tttctcccctg ttggatctcc taaggttttg    3900
ctcgtagaaa gtgatgactc aactcgtcat attgttagtg ctttgctacg gaaatgtagc    3960
tatgaaggtg atttgatctg ttttaatccc atatatgcaa tgtcttgtcc ttatcaccta    4020
cttcaacaaa tgattaagag aattgtactc cctcgttcca aaataatagc aacacttagc    4080
cttcccgtag actttaggga gcgtttggtt catattatgg tatgggtttg gaattaggaa    4140 tgaaccaag gtggtatggg gttggaactt gatacttaat accttgtatt tggtttcatt    4200
taggaatgaa aaaatttctt ttatttgata cctagaggta aggtatgagc catacccacc    4260
tccccccatg ggtttctaaa ccccatacct tatgggtttg aggtatgggt ttaaaattta    4320
aaaataagtt aaacaaacac taggtatgtg ttttgttcat tccaaaccca tacctcatac    4380
ctaaaactag tgaaccaaac accccccttaa ggatcttggg acaaagggaa tccattacta    4440
gatctggtga cattaatacc taagtttaca tcagtttcac ttaaatcctt cgttttaaaa    4500
aaagtaaaaa aacctgttag tctgagtaag tttactaatt tttgttctaa aattcaacac    4560
attatctaca tgcaagcact tactagtaca atacaactca aacaatatat gcatcctatc    4620
tgttcacaat gaaccgaaaa ctaatctttt catacccttg tttgatgctt ttttcaggcc    4680
```

-continued

```
atacaaattt ctttaaccta aattgcctcc tcagtcactg ttcaaaattg cagttttaac    4740
atcctcaaga ccatgtgatg tactgttaga ttatattaag accctattgt aaataaagca    4800
tgtatagtgg aataaaatgc atgtcttcct acttttttt gggggtcatg aactcattgt     4860
ttgatatttt gcagttgtag gggtgccaaa tggcatagaa gcatggaaaa tcttagaaga    4920
tttgagcaat cagattgacc tagttttaac tgaggtagtc acatcaggac tctctggtat    4980
aggtcttctg tccaagataa tgagtcacaa aagctgccag aatactcctg tcattagtga    5040
gctttcgttc cttgttgtat tagtgtatgt tctgtatttg attttctttc tttgtgcata    5100
tcttgccttg tttttacaa ttatttagat tttagatgaa aatgtatact cattttatgg      5160
tctttagctg caacatttga ttattttgtg tgcagtgatg tcatctcatg attcgatggg    5220
tttagtctta aagtgcttat ccaagggcgc tgttgactt ctggtgaagc ctataagaaa      5280
aaacgaactt aaaaacctt ggcagcatgt ttggaggagg tgtcacagtg taagtgtctt      5340
tacattttcc agcttccat cagcttagtg gttcgtgtag cagtctttca aattttcgaa      5400
ctttctagca catgacaa attaaacctg catgctaatt cccgattaga taatggaata       5460
agctctttca gctggtcttt tacttctttc tcttctcctc ttatgaaaaa ctggtatgcc    5520
actatgcatc ttgttccagg tgtttgttta gtgtttcttt cctttattcg ttttttttgtt   5580 tttatttta attttaattt taattttcc tcattctttt tttagtctag tggtagtgga       5640
agtgaaagct gtgtaaggaa tgaaaatcc ataggaagca agagggctga agagtcggac      5700
aatgacactg acatcaatga ggaagatgat aacagaagca ttggtttaca agctcgggat    5760
ggaagtgaca atggaagtgg gacccaggta gtgctaaccc ctgtaatatt aaacttccta    5820
tagtaggtgt ggttaatgtg acgctgttaa ggccttttgg gtggttgctt ctagttcact    5880
aaggataata agaaatagct cgctattgat agttagggca cctcaatatc acctcctctt    5940
gtatgtttgt tgaactacat ttttagccag acttgagtat tttatcctga aggatagaac    6000
aggtgcattt ttggttgcgg ttgttagttg ttactgttat gcaaagacta ttgccaccat    6060
tttctcacac atatttaaca tggaagtgtc ctaaccaccc cccaacccaa aaatgggag     6120 ggagaaatta ctggagatgg gaagaagtt acataaaaag ttagtcgttt gggtcatgat     6180
tgtttgttgt atttgcaaag ttagcgcgtt ctcttcctgg atgcttcaaa ataagctgat    6240
gcaccataaa gtaccactct tggcttcacc tgttggtgtg gacccaacca atgtaccctt    6300
gttgatctcg agatagacaa agaggaagtt taatttctct ttatatgtta tctctcttca   6360
atttgttagc agctatgtct ctttcgtgga catttagaac ccatgttagg ttcatattta    6420
tagttaggtg attgtatcaa aattgccatc acaataaaca gaacattaat ttctattggg    6480
aaggattcaa ggatcaaata tacaggaaag agcagtgtag gagatatcat cttgttgaac   6540 aacaaagaa acattaacat caactggtga taatctttgc aagattggat gacaaaatga     6600
ggagtcgatc taatataaaa caaattggga actgtcagct atatcctgca tatcaagaat    6660
ggagaccttt aagaaaagta agaccatttt ttgttgggaa gtcaagccat tgtcccagtt    6720
tccttgtgaa atttagttca tcttagcttt cttctaccaa catgaattct ctttcctttc    6780
agcccttgca aacttggttt tatgctaatt atcagtgttt ccttcattta gtacgctgag    6840
agggtttatt tggttgatca aagaatactt gatgaccttg aggtagatgc tctacatgga    6900
gaagttcctc taagtgtaca aagaatctag ttcgaccaac tttgatttag gaagagataa    6960
cacgatcacc tcgtggtcta gactctggag aggtcaaagt gtgcaaaggg gtatttttga   7020
aagacaatgg cttgttgatt catgactgaa attggatggt cgtgactgag catatactat    7080
```

```
tagtggttct cttctaaggt gatataagta tgtgataacc caatcctgta tatttcttcg   7140
aggacatcaa ttgtgctact attctagggt gctggagacc catacatata gagccattga   7200
caattaacac aaacttcaac cacttatttt tatttcattt aagctatcaa tccctaagaa   7260
agagcccatc caagctcctg ctttaggtgc atccctccc ttttcagcta gtgcacaaaa    7320
aatgaacttt cgagatagac tgctaaattt gctttgtcaa aagacaaaa ttttgataca    7380 caactgtaat tgcattttat gacacttacg ctgatatatc tgcaagtgaa gttgatatgc   7440
aaaaactatg tagcctcctt cgtctacggt aatagatctc cgtcaatgtg atgcttgtgt   7500
gccatcataa aatgatattg ggtctttaga ctctgttact ctacagctga aggatcttag   7560
ccttggcatt tatatccttt ttatccaaaa gttaaaaaaa gcggaccgtt tgacccatgt   7620
aaggaaaaag gaaggaatc gagaaagaca aaggagggga aagaagttaa atctcctaaa    7680
aagcttgttt tgtgcggtga gagagggagc gacttgaaat tgccattgat gatgattggt   7740
tcacaattgt aatcgaaatc aaactcactc tctctctctc tctctctctt atcaccccc    7800 tcaaactata acatcacagt cctttaaacg tgactgtttc gggggatagt gactggtagg   7860
gatgggcaag ggtcgggtct ggctggaccc tagacccgga ccctaatttt ttttttgtaga   7920 cccaaacccg daccctaagg gtctgaaaaa attggaccct gacccagacc cttagggtct   7980
gaagggtcta gagggtcagg agggtccagg cttaaatttt ttatttgcc aaattttag     8040 cattattaat atcaataatc atttgaaatt cgcatgaaac aaacacaaaa aaaatcgca    8100 tgaatcaaac acaaaattc gcatgaaaca aacactaaca tataattga aaaaacgaa      8160 acaaacacaa acttataaac gaaaaaaatt gaaacaaca caattccaaa catataaact   8220 gaaaaaaaa acgaaacaaa cacaatatata caaactgaaa aaagaagaa acaaacacaa    8280 cttacataag agttcagaat gggtgttata gtttatgttt tagtcattta gaaaatcaat   8340
ttgttttttt tttaaagtta aaatgtatat attaaataag tttagggtct aaggtgttgg   8400
aacatttata gggtaatggg tttgaaactc atatgggtat gtactagaag aggaggaggt   8460
ctagtatgca aaaggttaga gtgcatcaag tggtaacaac gcgcattgtt ataccaatgt   8520
cgcgagtcgc gacaggcgtc gcgggtcgcg accagcgcct cgcgagcttc ttcgcatgtc   8580
gcgacgcgtc ttctgccttg gaatgcgaaa aaatgcctcg gcggttttat atccgttgtg   8640
atgctttgtt gatcattta atgactttta aggtctttta atcagtagat taaaggcctt   8700
tgatgagtga ttaagatggg ggttatgtga ttaacctctc tagtcaatga aatgttgatt   8760
atgcttatat aaccttttgga ttcctatgag tgaggagtta gaagaaaatc agaattttct   8820
atactctctc aaaagtcttc ttgcttagct taagagaaac cttgcaatct tctcttgagt   8880
gttcttcaca aacacaaaac acaagttctt gttgattcac ttagaagatc atctaagtgg   8940
attgtttctc tccattgtat ctcattagtt atttcgtgtt aacccggtga tcctagaggg   9000
gcgaaattaa actaattgga aagcgtagtt tccgtgcctt ggagtgggat atccggttct   9060
ctcattgatc acaagcctaa cataagggtc gggtctgggt ccaaatttta agacccggac   9120
ccggacccta aaaattcac ttggacccag acccggaccc ggactcttag ggtctgaaaa    9180
agttggaccc aaacccttaa attagggtcg gtccaacag ggtccgggta gggtcttga    9240 cccatgccca tccctagtga ttgggtagcc cattgcagaa tattgagaac gcaatataaa   9300 gggtgttga gaaagagggt tttgagtgta ttgtttaaga aagttgggaa aggaatgaga   9360
gatgaagtac agaagaaaac gtctagaaag tgaagcatgg gagtctgttt ctttctttt    9420
```

```
tcctaaagtt tcccaccaaa tgtcccttaa gtggttcagc cacgcctttg acaagctta    9480
ccaccaagct ccccatccca gatcatattt gaatcaaaca tctttctttt tttagaatat   9540
tcttttttg tgcatgaaag ccaattccat gagatatgta ccttatattt ctctaaaata    9600
tataaataat tgatgaagca attttcagat cattagataa gcgttctaca aagaaccat    9660
cttttttgc ttccttgtgt acttggaaaa tgtagttccc atatataatt ttaccatggc    9720
agtacttcta tagaccacta agttcttcgc ttgtgcaacc tatagtgcat ttaagagggt   9780
ttaggtatag acagccttca ctttcaattg gttagagtct acctccagta tcactgacag   9840
aattttcaat aggaacttct gtcataactt aattcgcaga aagcactaac taaacaaccc   9900
cttagttctt tagttaagcg cttgattggt cacatccagc ttttagtttt tagtatggag   9960
atttataaag tagtatgact tgagttgaat agtgaacgta agattagaca tatttatata   10020
gtcgtgttaa ttttggaaac tgacaggagt gactagaaac cacttttttt gtgtccaaaa   10080
tttccatata ttgttttta aaaaaactgc taaatcacga tgataacaaa caaaccttac     10140
acaggtaccg gaatgatatt gaaacaaatt gaggttagtg ataagccata atcccttacc   10200
ttgaaattca gaggctgtct gctgcagtct ctatcatctt cttatttcac taaatcaatt   10260
attacctgct tcaacctcaa cggtccgagg cttagacatt gtgtctttga tagtatcatc   10320
acagctgaaa attaatgtgt actttcttct atttaaatac catttgagag tgcctttggt   10380
agtcattatg aatgtcgtga gatcacaatc cgtgaaatat agttttcatc acattcttac   10440
ctgcatgtgt aaggaaaagt atagcgttag tgttcaatct tttgctactt ctggtgactg   10500
gtcaatggtc aaagtatgca gcatgatttt gtgtttgtca gtttcttctt taaataagtg   10560
tgaactgctc tagtctaagt tgctcgaact cttaaaaagt gttggacttg ttagttgtta   10620
catgtataca atgttgattg ggtgggcttt tccatatatt attatatttg ttgaatcaca   10680
atgaagtacc tatttccatt tgaggagtag gtatgatgag gttagtaggg agtttgagtg   10740
ttaaaggtta tgtgaagatg taaaaattca ctgacaatga gaccttagta tccgacggtc   10800
ggaattttac caattttatt gccttgttac cttttctattt ttacttagta tttccttttc   10860
ataaattttt gtgatctaga gttcatggac aaaaagggct gcagaagttg agagccccca   10920
accacagtct acatgggagc aagcaactga tccacctgat agcacttgtg ctcaggtcat   10980
ttatccaatg tctgaggcat ttgccagcag ctggatgcct ggatccatgc aggaacttga   11040
tggacaggat catcaatatg gtatgtggta ctgtatttga tagaagttac aataatgtgt   11100
aaactgaaac cacttaatga cctagtatcc atctgtatca gacaatgtcc caatgggaaa   11160
ggatttggag attggagtac ctagaatttc agattcacgg ctaaatggac caaacaaaac   11220
ggttaagtta gcaactactg ctgaggaaaa ccaatattca cagttagacc tcaaccagga   11280
aaatgatggt cgaagttttg atgaagagaa cctggagatg aataatgata aacctaaaag   11340
tgagtggatt aaacaggcta tgaactcacc aggaaaagtt gaagaacatc gtagaggaaa   11400
taaagtatct gatgcaccac ccgaaatttc caaaataaag acaaaggca tgcaacatgt     11460
cgaggatatg ccttctcttg tgctcagtct gaagaggttg ggtgatattg cagacacgag   11520
cactaatgtc tcagaccaga atattgttgg gcgttcagag ctttcagcct tcaccaggta   11580
tgctagagaa ggtgaaactt gaatttatat aatggacaag tggacaatat ctcatttta    11640
aattgttgca ggtacaattc aggcacaact ggtaaccagg gtcaaacagg taatgttggc   11700
agttgctctc caccaaataa tagttcagaa gcagcaaagc agtcccattt tgatgctcca   11760
catcaaattt cgaatagcag tagtaacaat aacaatatgg gctctactac taataagttc   11820
```

```
ttcaaaaagc ctgctatgga cattgataag acacctgcaa aatcaacagt caactgttct  11880
catcattcac atgtgtttga gccagtgcaa agttcccata tgtctaataa taaccttact  11940
gcatctggta agcctggtgt tggctccgta aatggtatgc tgcaagaaaa cgtaccagta  12000
aatgctgttc tgccgcaaga aaataacgtg gatcagcagc tcaagattca gcaccaccat  12060
cactaccatc attacgatgt ccatagtgta cagcagctac caaaggtttc tgttcaacat  12120
aatatgccca aaagcaagga tgtgacagca cccccacagt gtgggtcttc aaacacttgt  12180
agatcgccaa ttgaagcaaa tgttgccaat tgcagtttga atggaagtgg tagtggaagc  12240
aatcatggga gcaatttcct taatggaagt agtgctgctg tgaatgttga aggaacaaac  12300
atggtcaatg atagtgggat agctgcaaaa gatggtgctg aaaatggaag tggtagtgga  12360
agtggaagtg gtagtggtag tggtgttggt gtggatcaaa gtcgatcagc tcaacgagaa  12420
gctgccttga ataaattccg tctcaagcgt aaagaaagat gctttgacaa aaaggtaata  12480
ctccaaattc tctccagaat gtttatactt ggacatctag tatgtacatc cttgaatcta  12540
aactgtaaaa gctgaatttc agaataaaaa acacaaatta tatcaagtat gaaggcagag  12600
tattgtagta attatagttt ttctggtatg gaattagtac ttacatttac cagaagcctg  12660
ctgtcacaag ccataaattg atcatcaagc aacaataatt tggccatttc ttgcttgtat  12720
tgaaagtgag atgacttcaa acttatttgt gtatcatcac atcaggtgcg atatcaaagc  12780
agaaagaagt tagcagatca aagacctcgt gttcgtgggc aattcgtgcg ccaggtacga  12840
gaaaacaaag gaaggaatac cgatagctaa caccaattct ttccacaagt tgctgccaag  12900
atcatttatg ccactctgat gtcagctgtc ttcatatgta caaatttcga attttatgtg  12960
tgcatgaggt gctaaatact gtcaaacctc agtgattctg tttggtttag ctgtagaaaa  13020
gacatctttt cctttgtgtt ttcatggttc ttattttgag ctgtgttcac tactttttat  13080
aacatggtag cccctggttg cctttggaaa taagcttttc cttaaaggtg tgatgcatat  13140
aatcttgttt ggtgttagat tatatgatca tttcttcagg cgtttacggg tcacattttc  13200
cggaatcctt tcaaacgcga ttccggaaac aatggctcat attttctttt ggtttcaagg  13260
agaaggctat ttaaaacaga aaagatttag gttacagaaa tcagtgatga agcaatgagt  13320
ttcattatag aataggtaga agtaggggt gttttttccg tactcttgag atagaaagtg  13380
gggatagatt ctttggactc gtcagaaagg aataatatag ttgtctacct ttttcatttt  13440
tagttcttgt aggagtttta ttccacttcc atttttgtaa aatttaggag ttgtaaggac  13500
gtgtaaagag aatctgccat ccagatttta accgacggta aatttgttct tttcatgttt  13560
tctcaagtaa ctataatgtt ttcatcgaat ctatagggat tttctaatgt gtacctgata  13620
gaggcacaca gtaacaataa tataagtaca tatattcttt aagaataatg acatagtaat  13680
tatattttta atacaaataa aagatgtcct tatgtaatga aacaaataac ttttccttga  13740
aggtatgcca taattaatta ctttattttg aagatatttt atatttagtt tgggtagtgg  13800
aactactaaa taaaaatatg gttatagtaa catgtactca tgtgcgaacc gaaaaaaacc  13860
ctatgctttc tctaaaagtt cccaaaccct tgagcttata gccccgacgg cccagcgcag  13920
gcttgctgga gcgccgcgtc gctcaccctg tcgccgacga gcctgcatgt cgtatcgttc  13980
ggtcttctga aggtttagtt ttccctgttc ctctttgtgt tattcatcgt tcccatcccc  14040
catgtctccc cttccctgt cagtggttgt cggcctcccc ttccctatt aatggttgtc  14100
ggcctcccct tcccttcccc ctaatagtgg ttgttggtct cccttccc tttcatgttg  14160
```

```
tcaagttgtt cctttccccg ttctccctttt tcctagtcct cttttggtgt tcttgttgtt    14220
gttagtttag tggctttggt tggttagttc ggctgagtgc ttcgtcgtcg tatgcccttc    14280
cttgttcccc tatttggttt tggttatgtt ggggtttcgg ttaacccgt  tcccatgctt    14340 aaacgtggga gggcctcagg atttagatat aaaggtcatc attctcgcgc ttagacgtga    14400
gagggattaa gtgttcaggg ataagggctc cgttcctgcg cttaaacgtg ggagaactta    14460
aaggttctag gttttacagg agttttggga ttggaaagta tatgaactct gtttggcaga    14520
agatgacagt gcaatgtggg gattaatcat ttcgttttct tccttttaa  taagttagtc    14580 tcttattatg agagtttttct attagttcta atccccttaa tttcttgtag ggggtgtaag    14640
tctagtttgt cgttgtttag tatatctagt tcgagaagct cgaaagtttg aggttgtgga    14700
aaaatgtact tactggttgc agatcaagaa tattaagacg aatgtttgac ttcaatttac    14760
tattgcatca ggtaggaaat atggtgagtc atcgaatatc cattatggtt ggaatagtac    14820
catatcatgg aagcggtttc gaagcgtgta tattagtaaa atagatgaag atattcaaat    14880
cgatgtttta gattatcttt tatgtacgta agggtcatta ttgttgtaga tgttgtatgg    14940 tttttttaatt taatgataat ttttccttat tcccacttaa aagtaaacaa tgcattcatg    15000
tgcacatatt agtacatata tttgtatata catctcg                             15037

<210> SEQ ID NO 8
<211> LENGTH: 24128
<212> TYPE: DNA
<213> ORGANISM: Beta vulgaris

<400> SEQUENCE: 8
maaacgttgt gatcatctaa tattattgaa tatattatct ccataactta tcctaatatt      60
atttagttta ttcacttga  tcgaggacaa aatccttcaa tctcccactt gtctaagaac     120
aagtgtgtaa ccttcaaact ccttaagtcg cttaatgtct aacttgatga catgataaca     180
tcatatgttc atcataacaa tattcaagtc gttccttgaa atctgagttt gaactgtcga     240
aacaaatgat taacttctta atccatttga gcacggccat gcattttcag ttctcactct     300
tcaagaggcc aagacaccaa tcctaactct taggaggact tatccaatct tgtatgacca     360
aagctcccac tcaattcata gcagttccaa tcgctgcttt tataacctcc ttttacggca     420
cggcgttttg cagcgtcaag aacatactaa tccttaagta agaacagttt catactcatg     480
tcaaaggaat ccactaaata tattaataag agtctcataa accttttaga gaactcccac     540
taggtctgcc cagcgtgtat caactataca agcctatgca aatgactaga catctccatg     600
tccctatagc ccatgaaact gcgctatcaa tcaacttgca atctagtcca tgaaattgaa     660
tcatttacgt tcaacttaat gattcgaact agggactaag gtatattata actcctgttc     720
actggataga gttccattcg tcaaatcacg tatttgacaa ttctatcaaa cgttataaaa     780
tactttgaac gttttattta atactaaacc aagattaaat aagaacaaaa cttttattga     840
taaacataaa cataacatat caaagcgagt aattataact gtgaactaat taaaagtaaa     900
tagtacacaa ttaaacccac tctcctatat gcttaagccc tatagcccta gtatgactct     960
catgcttggg ctgtggcaaa ggtttagtca aaggatcagc gacattacta tccgtatgaa    1020
ccttgcaaac tattacatcc tttctctcaa cgatttctcg aatgagatga aactttctaa    1080
gtacatgttt acatctttga tgtgatcttg gttccttaga ctgagctatg gcaccattgt    1140
tatcacaatg taaaacaata ccatctccaa cactaggcac tactcctagc tccagaatga    1200
acttcttcat ccaaacggct tcctttgctg catctgctgc agcaatatac tcagcttctg    1260
```

```
tcgtagaatc agcgacagtg ctttgctttg aacttttcca gctcactgcc cctccattta   1320
gacaaaagat gaaaccagat tgggatcgga aatcatcttt gtcagtttgg aaacttgcat   1380
ctgtgtaacc ctcaacaatt aacttacttt tacctccata cactaagaaa ttatccttag   1440
tccttctcaa gtactttagg atattcttag ctgcactcca gtgtgcgtca cctggatttg   1500
attggaatct gctacacatg ctcaaggcat atgaaacatc tgggcgagta caaatcatgg   1560
agtacataat ggagcctata gctgacgcat aaggaacatt actcattcgc ttaatctcat   1620
caggcccaga aggacactga gtcttgctaa gcgacactcc atgttgcatg ggtaggaagc   1680
ctctcttaga gttttccatg ttgaacttag tgacgatctt atctatataa gttcgttggc   1740
taagtccgat catcctctta gacctatccc tatagatctt gatccccaaa atatactcgg   1800
cgttttcgag gtcttcata gaaaacaac ttttaacca ttccttgact gactcaagca   1860
tgggaatgtt gtttcctatg agaagtatgt catctacata caagaccaag aagactatgt   1920
tactcccact ttccttcttg taaacacaag actcttctcc atttttaaga aaccaaact   1980 ctttgattgc ctcatcaaaa cgaagattcc aactccgtga tgcttgcttc aatccataaa   2040 tggattttg aagcttacat accctcctag gattttctgg atccacaaaa ccctccggct   2100
gtgtcatata cacatcctct ttcaagaacc cattcaagaa agcggttttg acatccattt   2160
gccaaatctc gtaatcatag aaggcggcga tcgctaggag tatccgaacg gatttaagca   2220
tggctaccgg tgaaaaggtt tcgtcatagt ctataccatg aacttgcttg aaccctttg   2280 caaccaacct tgctttgtaa acctgaatat taccatcctt gtctgttttc actttgaaaa   2340
cccatttgca accaataggt gtgatcccat cgggcaaatc taccaagtcc catacttgat   2400
tttcagacat ggatgccatt tcggacctca tggcttcgag ccattttcg gagtcttcac   2460 tcatcaaagc ttgcttgtaa gtagtaggtt cctcaaattc taaaatcatt atctcagaat   2520
tttcagttaa caagaaatca acaaacctct tggttggtat tcttgttcta ctagacttac   2580
gaggggctgc aacaggagaa atttcttct caacaatatg agaattttcg cacgaattag   2640
attcgagtgg gacaatagga ggttcgtgta cgggatgcac gtcctccaac acttggtcag   2700
ttatgggaga agattcctcc aaaggaggaa ctacttcaag cccaacatct ggctcttgtg   2760
tcgttgtctc taacatagga tgaactatgt ccatttgttg atcttctcga acttcttcga   2820
gaaatacatt actcccactt gccttttggg aaataaaatc ttttttccaaa aagacaccac   2880 gacgagcaac aaacactttg ccctcagtgc gattgtagaa gtaatagccc ttggtttcct   2940
ttggataacc cacaaagaaa cacttatctg atttagggc gagtttatct gaaagtaaac   3000
gctttacata aacctcacat ccccaaatac gtagaaaaga caagtttgga acttttccac   3060
tccatatctc atatggtgtc ttatctactg cctttgatgg agttctatta agtgtgaaag   3120
tagcagtttc gagagcatat ccccagaagg atattggaag atcagcaaaa ctcatcatag   3180
accgaaccat atcaagtaga gttcgattcc tcctttccga acaccattc aactgaggtg   3240 ttccaggcgg agtgagttgt gaaagaattc cacaactctt caagtgatca ttaaactctt   3300
ggctcaaata ttcaccacca cgatcggatc gcagtgcttt gattgttttg ccaagctggt   3360
tttggacttc attttggaat tctttgaatt tttcaaatga ttccgactta tgcttcatta   3420
aatagacata tccatatcta cttaaatcgt ccgtaaaagt aatgaagtat ccaaaccctc   3480
ccctagcttt tgtgctcatt ggtccacata catccagtatg tattaggccc aatagatcac   3540
tgaccttttc acccttcca gtaaaaggtg actttgtcat tttacccatt aaacatgatt   3600
```

| | | | | | |
|---|---|---|---|---|---|
| cacacacatc | aaatggctca | aagtcaaaag | atgttagaag | tccatcttta | tgcaacttct | 3660 |
| gaatgcgttt | cgcgtttatg | tgtcctaaac | gacaatgcca | taagtaagta | ggattagtat | 3720 |
| cgcttgttct | atgtttttg | ttgtctatgt | taaggacatc | tttgtctaag | tctaggtaat | 3780 |
| atagaccatt | agacctctta | gcagtggcat | aaaacattga | attcaaataa | acagagaaac | 3840 |
| aacctttctc | aattgtaaat | gaaaacccctt | cattatccaa | aacaggaata | gaaataatgt | 3900 |
| ttttggtaat | agcaggaacg | taataacaat | tattaagctc | taatattaat | ccagaaggca | 3960 |
| aaggtagact | ataagtccca | actgcaacgg | cggcaactct | tgcaccattt | ccaactcgca | 4020 |
| gttccacctc | tcctttagcc | aaggttctac | tccttcttag | tccctgcaca | ttcgaagtaa | 4080 |
| tgtgagaaac | acaaccggta | tcaaataccc | aagaagtaga | tgttgctaaa | ttaatgtcaa | 4140 |
| tgacatagat | acctgaagaa | gaagcccag | acttcttatc | cttcaagtac | tttgggcagt | 4200 |
| tacgcttcca | atgacctatt | tgatcacaat | agaagcactt | ggcatttgcg | gccacctttg | 4260 |
| gctttgcctt | tgcctgtggc | ttaatagcag | tcttagtggc | aacttgcttg | cccttatctt | 4320 |
| gcttttcttt | gccagcccat | tccttcttaa | aaccctttc | ctttgaacc | ataagaactt | 4380 |
| ccttcttagg | tgcaatagtg | atgttttgct | cggcagtcat | gagcatccca | tgcaactcag | 4440 |
| caagggtttt | cgacacccca | ttcatattga | aattcaatcg | aaacgtattg | aacccttat | 4500 |
| gaagtgagtg | cagaatgatg | tcagtagcca | actcttggct | ataaggaaag | cccaacctct | 4560 |
| ccatggcttc | aaaataacca | atcatttcga | agacatgagt | ggcgaccggc | ttgccttcaa | 4620 |
| ctaacgaaca | ctcaagaata | gccttgtgag | tttcataccct | ctctatccga | gcttgttgtt | 4680 |
| gaaacatggt | tttcaactgt | cggataatgc | tataggcatc | caagcttgca | aacctctttt | 4740 |
| gaaggcttgg | ttccatagcc | gctagcataa | ggcaagtaac | aattactgac | ctttctgcaa | 4800 |
| cggcctatg | ggcctcttc | tcagcatcag | tagaggtagt | agttaaaact | gggatcggtg | 4860 |
| tttcaagaac | atcctctcga | ccttcggacc | taagaacaat | tcttagattc | ctttcccaat | 4920 |
| caaggaagtt | gttcccgttc | aatttatcct | tctcaaggat | tgaacgtaag | ttaaaaggtg | 4980 |
| aattattgtt | gttaccagac | atgatatcta | catagaagat | gcaaaaagta | taagtatgtt | 5040 |
| tatcataata | gcttttaaca | aatttttaaac | acttaaaat | aaaagctatg | cacttgacca | 5100 |
| atttaatgt | gtcccttttg | aatcaagtgg | ttctaagatc | ctatcaaaca | tgatttataa | 5160 |
| gtggactttg | gcctcaactt | aaaaccaagt | ttaaaggta | agtaaactcc | tttactaatt | 5220 |
| acaacaattg | taactcttag | ttaatgggtg | attgctaagg | tgattacgct | cccaggtaag | 5280 |
| gaagttaccc | acaacgttgg | ggagagcctt | cctaatccta | gacagagcat | gtcacccaaa | 5340 |
| cacaaaaacc | cataaacttt | gctacaaaat | ccaaaaccgt | tttgatgatt | tgttgggcc | 5400 |
| aaaccaaact | aaacttgcaa | atttcggaaa | tttactctac | ttagcccaag | attgaaagta | 5460 |
| atactctgct | ttggcagaac | ctattactaa | cgatcaagtt | ttagtaggtg | tttatttgga | 5520 |
| atagcaaaaa | cccaatattt | tatttaaggg | acctaagtaa | attattatgt | tgatttaatt | 5580 |
| gctagtgaac | atttaaataa | ttaaatcaca | agcataataa | acttagaaag | catttaaaag | 5640 |
| caatatttaa | atgcataaaa | ttaaatatga | tcctagtatg | gccctaaac | ctaaagacta | 5700 |
| ctctttaaga | ctcccttgtt | gaatcaccat | ggatctccat | ccttgtgctt | cataggataa | 5760 |
| gattgaatca | ccattcttct | tattaatact | tgaataaata | ttttttgaaa | ttataaacta | 5820 |
| aaaaattaca | aaaatacca | acgatgcgta | gatcgtattt | agattacaaa | aatacattaa | 5880 |
| cgatacgcat | atcgtatttt | ctatccagt | tttgggccat | actagtcacc | gcatgcattc | 5940 |
| ataatatcat | atatacaaaa | acatgcattt | taatcaacta | ttaaaataaa | ttatcatgtt | 6000 |

```
ttaacaactt taaaacataa taacaccatg aagatttaat cacacattaa atcctatggt    6060
tggtaccttg agacaaaatt taatcatatt agaatttcgt ctcacaaagg ctttaaaata    6120
ttaatctaac aaatttaatc atattaaact taaagaaaaa ttaaagcaat tgtaggcacc    6180
acatataatt taatcatatt aaaaacaaaa acttaacatg atgactaacc acataaaaag    6240
ggcatgaaag aattaatcaa ctattaatac taacaaccta acatgtaatt aacatcataa    6300
aaaaataata atagttacta actccttagt aaccccattt aaaattaact agtcaattat    6360
cacatataat taactaataa aattaaagct cattatttaa ttcaattatg acttaaatat    6420
aaaattaatc accattaatt aatttatttg caaattggaa tatactcaaa aacaagaaaa    6480
agaaagaaaa aaaaaaaaaa agcaggctgc caaggcagca gtgtacactg ccacctcagt    6540
gccggccacc tgcgcgacca ccagaaacga ccagaacctg ccaccgcgtc gctggccacg    6600
gcgaccagca ccggcagcac tgcagcgcag gcagcaggcc gcgccaacag cagcgcccag    6660
cgcaggaagc tcgcgccgcg cgagccacca cgacgccggc cacagtccgg cggcacgcca    6720
gccaccatgt cggtcgaatt ccggtggacc ttccccccttt ccctttcaat tatcatcaac    6780
ccttgtgcat aattgaatga aagttacaac aaattgattt ggggaaaaaa ttagggttca    6840
tatcaatttt gttttaaaaa aaamcatgaa ctaacacaaa aaatctgata ttttgtgatg    6900
tgagatttca attttgagta taatatatat ttatatatat acatwaaaat ccaatttta    6960
tgtttccaat caattaatat cataatatca attatgcaaa taaattcata tataaagccc    7020
tcccttaatt gaattaaaaa atgaaataaa acatgcatca acatgatcat attaatctat    7080
gcaataggct aactgatacc actgtaggaa cttagatgca taatgcggaa aatcaagtat    7140
caaatacttg tacatctatc ccaagatcat tgcataaatt agtatgaatc aaacaatagt    7200
atagaattat acctttgatg cgtatgttcc tcttgtcacc aaacttctag tggagatcac    7260
cttagaacgt caagcgccgt tcctctaatg ttggtccacg aacaacactt ggatcaccac    7320
gtatgctagt acggaagaga gaaaaacact ctcttacttt tgtggtgagg gccgaaaatg    7380
agtgtgaaaa gactaaggga aaaatcagat ttttcactct agaagttgta aagtgtata    7440
tccacctttg taacccata tcaatatata aggtggttac aaaagaggtg tttcatgagg    7500
ctttatttts cctcataatg tcatacatta tgagtctaat aaactcatga gttacaactc    7560
ttcccatcca tcatcaaacc gcgcaaccca tttcacaaat ggatttggat aaatatccaa    7620
gtgtcattac ttgtgtgacc tcataggact caatgatatt agtagttggc cctaatcata    7680
ttagtccaac aaaccacaat tagcttctag caaaacgttg tgatcatcta atattattga    7740
atatattatc tccataactt atcctaatat tatttagttt attacacttg atcgaggaca    7800
aaatccttca caaatgcata tggtttgatg tacaataata tacgagtgta catttgggta    7860
ttttcaatga tcaaagtaat gaccatcagt gtacattgtg atttatcctt atttacgttg    7920
gttgcggtac cttttttatta ttattattag ctccacctac agttgcatgt acatgcacgt    7980
acctagcatg tacactttgt tgacattcat gtacattaac cgggttaacg ttacaattat    8040
gttgttatgt gttgaccttt tgttttaata ctcgtattga gtttttttg tttgttgt      8100
gtctatatca caaggattgt actttggatg tctattattg ttcattgtgt gttattgacg    8160
attttatggg gggatgtcat tgtgcatttt gattttgtta atgaacaacc acgaagccaa    8220
gaatgtacaa agaaacataa tagaataaaa gtaacccaat tcctaaagct gatgtcaagt    8280
gagtaatttg caatctttgt acactggtgt gttgatgttt gttcgcttat gaaattcaat    8340
```

```
atgtacaatt atagtcatat acctcatagt gctccaggtg ccacaaaaaa aactcaatat    8400
gggtattaaa acaaaaggtc aatacataac aacatgattg caacccagtt aatgtacatg    8460
aatgtcaaca aagtgtacat gcaaggtacg tgcatgtaca tgcaactgta tgtggagcta    8520
ataataaaaa aaggtaccgc aaccaacgta aataaggata aatcacaatg tacactgatg    8580
gtcattactt tgatcactga aaataaggat acattattgt ttgattgaat gttcactgga    8640
tatgactcaa tgtacaaata ttctagcaag attgttcaat tattaagcct gaatgtacaa    8700
tgttgttatg actgaatgtt caagttattt tatagagctg actttgttct gtgtacatta    8760
aagttgcgtt aatgatcatt gtgtatgact aaatatacat tagcttcact aacatgcgtg    8820
cataacatat tctatagaca caaacaaaac aaaaaaaaac tcaatatggg tactagatta    8880
aaaggtcaac acataacaac ctgattgtaa cccagttaat gtacatgaat gtcaacaaag    8940
tgtacatgca aggtacgtgc atgtacatgc aactgtagat ggagctaata ataaaaaaaa    9000
ggttccacaa ccaacgtaaa taaggataaa tcacaatgta cactgatggt cattactttg    9060
atcactgaaa atacccaaat gtacactcgt atattattgt acatcaaacc atatgcattt    9120
gttacattaa aaaagttttt aaaaatgcaa aacagaaaat aaaatcaaat atcgacattt    9180
ggaaatttat aatagaaatg aataaaaata agggagaaat aaatgaagaa caaaataaat    9240
gagaaagaga attaaaatgg ttcttgaaaa ataaatgaga gagaaaagga gggaatgagt    9300
gagtgatgag agagaaagag ctggcccact ttcaaaaatt ctgccaaaag cctgccaaat    9360
tttggccctc ctaaaagcat caaaactacg tagttttggc caaggtgtag gatgctcatc    9420
ctacacctcc gtgcaggatc taaattgcgc ttagaaatag ggtctcctaa tatttctcta    9480
ctagcatttt ttgcacgcga tgcgtgcttg aattttttc aagatagaaa ctcgattttt    9540
ttcgacgtat gtaaaagtca aaatttaaac attagacata caaagtataa ttgtttttag    9600
ttacaaaatt taattggttt agtctctgta acttgagttt ctcaccagtc tttttttttt    9660
ttttttttt ttttactttc aaagttaaat tctatgaaca aaatagaaat tttattgaat    9720
ttatctatga tttctaatat tactccctcc gacccaaaat atagttccca tttccctttt    9780
ttcacggtaa tttatgcaaa tagaatataa gagggatagt aaagattttt tgtttattta    9840
aataaatgtt gtatgggaaa agatgatttt aggagagaaa gtagagaata attggtgaaa    9900
gagtattaat tgtaacattt tggttgaata acaaaggaa aaaacaaaat tcaagaagca    9960
aataaatgag aattgtttcc ttgaataatg caaagtggg ttttaattcc caaaatatgc   10020
ccaaaaataa aaaaattccc tgtgtaccgt ccacgtaaga cggcacgcga gattttttt   10080
tcctacttca atacaaccgc tacttaaagt agcggtttac tgatttttt ttttatctac   10140
ttaggtaaaa ccttggcgct gagtgatata actcgctact tcaagtagcg atttactgaa   10200
atccccaact ccatagtttg atatgtgctt gcaacatttt gcccaggtaa accgctactc   10260
agggtagcgg tttatgtgta taaaccgcta cttaaagtag cggtttattt taatataaac   10320
cactattgtg agtagcggtt tacgtgggca aaaacaaaaa aaaaaatagt ttctcgcgtg   10380
tcgtcctacg tggacggtac gcagggaatt ttttaatttt tgggcatatt tgggaacta   10440
aaacccactt tgcattatt caaggaaaaa attcaaataa atgatgggac acggttttc   10500
tagacaaatt acgaaaaaat gtggaactaa atatgaaat ggaaactata ttttgggaca   10560
cccaaaatgg aaatgggaat tatatttttgg gacggaggga gtataatttt ttagttgatt   10620
tttgaattaa gtatactact tcatatattg ttaagaaact ggacacttgg atttcaagtc   10680
aaatttttgt gagtatgtat tgacgttgta gtgtattggt tgtagtttgt aagttaattt   10740
```

```
ttgttttttgt aaagtttact catttgagtg atttgtataa tgtaaattat gcaattctat  10800
gattttagtt gacttgtgag tgattgttat aattttattt ccattatttt tatttgaatc  10860
tcccttggt  ttgtatgtga atttgtaatt tagaaaggca aagggtaaa  atagtctctt  10920
cattcgggaa caccatagtt ccctccttc  ccttatataa taaagatgat gatgatttt   10980
gataataatg atttgtaagt gaattatgtg aatgttttg  tatgtattga cgtcctagta  11040
tattagtttt agtttgtaag ttaattttt  tgttttgta  aagtttccg  atcatttgag  11100
tgattttcgt gatttttgt  gatttctca  attctatgag tgatttgtaa agtttcttga  11160
tataagtgat ttctgagtgg tgttgaatta atttccggtg gctttgttag aaccccattt  11220
tagtattgac atttcttttg taatttagaa agggaaaggg gggtaaaata ggcatttcaa  11280
aaaaggacac cattgctccc cccttcccctt atgtaattga gatatcttaa aagaataccg 11340
agagttttt  cccataaagg agtatttttt ttaaaattt  ttccataaag gagtatttat  11400
tagtaccaag ttgatttccc aaatcattat ccttgcgcaa attgcataat ggagatattt  11460
ggtgttgacg tgtgaatatg gggccataat aataggaggt caaaaacaaa actacaaggg  11520
ttaaaatcgt cacaatatta aacaagcatc tcacattctc actggtcact ttttttaac   11580
ctattaaaag aacaaacctt taactctcct cacaatctga cacgtgtcga atattgattt  11640
actgagatca atttagatcc tctcccttag actcttctgt cttctcagta cagctttaga  11700
tctcaacctc catgtcagca aagttacctt acgtgtcatc ctacgtggcc tctccttcta  11760
cccctcactc ctccacgtca acatttcct  ccaaaattaa aaaatcattt ttttattata  11820
tttacttgaa tgtatataat aatgtctact gatcttcttc tttagaacta tctccttctc  11880
tcattggaac ctcaaaatca ttcttatttt atttcgagaa aaggaaaaaa aagcacatct  11940
tttttgaaga ttaatttgtg gattattatt gagcttcatc gtattaaaaa acatagtaaa  12000
agttctttcc tcatttgtct ttttattcat ctaatttttt ttagtgaaga accctaattt  12060
tgtttgtgaa ttctcaagtt caagttttga tttgggtatt ttttttgatg aaatttgtgc  12120
agctgtagga tgttatcgtg ctgagaaaag ggttttagat ggtaagtttt ttttctttg   12180
atttctctct cctactttt  ttttgtttt  gctttagata atactgtcat gatatgatat  12240
aaagaattgg tgatttgggt agttatttta acctatgatt atgtgttatt tgttttgatc  12300
tttcaattta tctggtgctg tgtgtatata tgttttgttt ttcttcaagt atttggttat  12360
tattgaagtg ggtaattagg aatttgctac taatctatgg atttgggttc tgttgtgatt  12420
aatttactat agatttgagg tttaatttat gttttatagg ttagaaaagg aaatcaatga  12480
tttgtttgtg gatttgagta gattgtttgt tagtgtgtgt atgatgatat taacttccat  12540
tattcttccc caaattaggg gtaattgatg gttttttgca taccgaaggc gtattctctt  12600
tgatgatgga gtgattgttg aaaagacatg atgggttaaa gttgcaggat tatttcattt  12660
caataaacat aattgatcaa tttggatctg ttgaatgagg ttgattcaca aaaatgaaga  12720
tgggcccggt gttgccaagt cggtggcaga gcttaatcaa catatagttg ctgtgaaaaa  12780
agaaggtagg ggtagggttg caggtgaagg gcagggggctt tccgaggagg acgaactgag  12840
aattattgag gatggtgaag atgcaaacag caggcgttct tgagttctg  ttcagcttcc  12900
agttcatact cacaggcatc agccacaagt acaaccccag gggagagtct gttgggagag  12960
gtttctccct gttggatctc ctaaggtttt gctcgtagaa agtgatgact caactcgtca  13020
tattgttagt gctttgctac ggaaatgtag ctatgaaggt gatttgatct gttttaatcc  13080
```

```
catatatgca atgtcttgtc cttatcacct acttcaacaa atgattaaga gaattgtact    13140
ccctcgttcc aaaataatag caacacttag ccttcccgta gactttaggg agcgtttggt    13200
tcatattatg gtatgggttt ggaattagga atgaaaccaa ggtggtatgg ggttggaact    13260
tgatacttaa taccttgtat ttggtttcat ttaggaatga aaaaatttct tttatttgat    13320
acctagaggt aaggtatgag ccatacccac ctccccccat gggtttctaa accccatacc    13380
ttatgggttt gaggtatggg tttaaaattt aaaataagt taaacaaaca ctaggtatgt     13440
gttttgttca ttccaaaccc atacctcata cctaaaacta gtgaaccaaa caccccctta    13500
aggatcttgg gacaaaggga atccattact agatctggtg acattaatac ctaagtttac    13560
atcagtttca cttaaatcct tcgttttaaa aaagtaaaa aaacctgtta gtctgagtaa     13620
gtttactaat ttttgttcta aaattcaaca cattatctac atgcaagcac ttactagtac    13680
aatacaactc aaacaatata tgcatcctat ctgttcacaa tgaaccgaaa actaatcttt    13740
tcataccctt gtttgatgct tttttcaggc catacaaatt tctttaacct aaattgcctc    13800
ctcagtcact gttcaaaatt gcagttttaa catcctcaag accatgtgat gtactgttag    13860
attatattaa gaccctattg taaataaagc atgtatagtg gaataaaatg catgtcttcc    13920 tactttttt tgggggtcat gaactcattg tttgatattt tgcagttgta ggggtgccaa     13980
atggcataga agcatggaaa atcttagaag atttgagcaa tcagattgac ctagttttaa    14040
ctgaggtagt cacatcagga ctctctggta taggtcttct gtccaagata atgagtcaca    14100
aaagctgcca gaatactcct gtcattagtg agctttcgtt ccttgttgta ttagtgtatg    14160
ttctgtattt gattttcttt ctttgtgcat atcttgcctt gttttttaca attatttaga    14220
ttttagatga aaatgtatac tcattttatg gtctttagct gcaacatttg attattttgt    14280
gtgcagtgat gtcatctcat gattcgatgg gtttagtctt aaagtgctta tccaagggcg    14340
ctgttgactt tctggtgaag cctataagaa aaaacgaact taaaaacctt tggcagcatg    14400
tttggaggag gtgtcacagt gtaagtgtct ttacattttc cagctttcca tcagcttagt    14460
ggttcgtgta gcagtctttc aaattttcga actttctagc acatatgaca aattaaacct    14520
gcatgctaat tcccgattag ataatggaat aagctctttc agctggtctt ttacttcttt    14580
ctcttctcct cttatgaaaa actggtatgc cactatgcat cttgttccag gtgtttgttt    14640
agtgtttctt tcctttattc gtttttttgt tttatttttt aatttaatt ttaattttc     14700 ctcattcttt ttttagtcta gtggtagtgg aagtgaaagc tgtgtaagga atggaaaatc    14760
cataggaagc aagagggctg aagagtcgga caatgacact gacatcaatg aggaagatga    14820
taacagaagc attggtttac aagctcggga tggaagtgac aatggaagtg ggacccaggt    14880
agtgctaacc cctgtaatat taaacttcct atagtaggtg tggttaatgt gacgctgtta    14940
aggccttttg ggtggttgct tctagttcac taaggataat aagaaatagc tcgctattga    15000
tagttagggc acctcaatat cacctcctct tgtatgtttg ttgaactaca ttttagcca     15060 gacttgagta ttttatcctg aaggatagaa caggtgcatt tttggttgcg gttgttagtt    15120
gttactgtta tgcaaagact attgccacca ttttctcaca catatttaac atggaagtgt    15180
cctaaccacc ccccaaccca aaaaatggga gggagaaatt actggagatg ggaaagaagt    15240
tacataaaaa gttagtcgtt tgggtcatga ttgtttgttg tatttgcaaa gttagcgcgt    15300
tctcttcctg gatgcttcaa aataagctga tgcaccataa agtaccactc ttggcttcac    15360
ctgttggtgt ggacccaacc aatgtaccct tgttgatctc gagatagaca aagaggaagt    15420
ttaatttctc tttatatgtt atctctcttc aatttgttag cagctatgtc tctttcgtgg    15480
```

```
acatttagaa cccatgttag gttcatattt atagttaggt gattgtatca aaattgccat    15540
cacaataaac agaacattaa tttctattgg gaaggattca aggatcaaat atacaggaaa    15600
gagcagtgta ggagatatca tcttgttgaa caacaaaaga aacattaaca tcaactggtg    15660
ataatctttg caagattgga tgacaaaatg aggagtcgat ctaatataaa acaaattggg    15720
aactgtcagc tatatcctgc atatcaagaa tggagacctt taagaaaagt aagaccattt    15780
tttgttggga agtcaagcca ttgtcccagt ttccttgtga aatttagttc atcttagctt    15840
tcttctacca acatgaattc tctttccttt cagcccttgc aaacttggtt ttatgctaat    15900
tatcagtgtt tccttcattt agtacgctga gagggtttat ttggttgatc aaagaatact    15960
tgatgacctt gaggtagatg ctctacatgg agaagttcct ctaagtgtac aaagaatcta    16020
gttcgaccaa ctttgattta ggaagagata acacgatcac ctcgtggtct agactctgga    16080
gaggtcaaag tgtgcaaaag ggtattttg aaagacaatg gcttgttgat tcatgactga     16140
aattggatgg tcgtgactga gcatatacta ttagtggttc tcttctaagg tgatataagt    16200
atgtgataac ccaatcctgt atatttcttc gaggacatca attgtgctac tattctaggg    16260
tgctggagac ccatacatat agagccattg acaattaaca caaacttcaa ccacttattt    16320
ttatttcatt taagctatca atccctaaga aagagcccat ccaagctcct gctttaggtg    16380
catcccctcc cttttcagct agtgcacaaa aaatgaactt tcgagataga ctgctaaatt    16440
tgctttgtca agaagacaaa attttgatac acaactgtaa ttgcatttta tgacacttac    16500
gctgatatat ctgcaagtga agttgatatg caaaaactat gtagcctcct tcgtctacgg    16560
taatagatct ccgtcaatgt gatgcttgtg tgccatcata aaatgatatt gggtctttag    16620
actctgttac tctacagctg aaggatctta gccttggcat ttatatcctt tttatccaaa    16680
agttaaaaaa agcggaccgt tgacccatg taaggaaaaa ggaaaggaat cgagaaagac      16740
aaaggagggg aaagaagtta aatctcctaa aaagcttgtt ttgtgcggtg agagagggag    16800
cgacttgaaa ttgccattga tgatgattgg ttcacaattg taatcgaaat caaactcact    16860
ctctctctct ctctctctct tatcaccccc ctcaaactat aacatcacag tcctttaaac    16920
gtgactgttt cggggatag tgactggtag ggatgggcaa gggtcgggtc tggctggacc      16980
ctagacccgg accctaattt tttttgtag acccaaaccc ggaccctaag ggtctgaaaa    17040
aattggacct tgacccagac ccttagggtc tgaagggtct agagggtcag gagggtccag    17100
gcttaaattt tttattttgc caaattttta gcattattaa tatcaataat catttgaaat    17160
tcgcatgaaa caaacacaaa aaaaaatcgc atgaatcaaa cacaaaaatt cgcatgaaac    17220
aaacactaac atataaattg aaaaaaacga aacaaacaca aacttataaa cgaaaaaaat    17280
tgaaacaaac acaattccaa acatataaac tgaaaaaaaa aacgaaacaa acacaaatat    17340
acaaactgaa aaaagaaga aacaaacaca acttacataa gagttcagaa tgggtgttat     17400
agtttatgtt ttagtcattt agaaaatcaa tttgtttttt ttttaaagtt aaaatgtata    17460
tattaaataa gtttagggtc taaggtgttg gaacatttat agggtaatgg gtttgaaact    17520
catatgggta tgtactagaa gaggaggagg tctagtatgc aaaaggttag agtgcatcaa    17580
gtggtaacaa cgcgcattgt tataccaatg tcgcgagtcg cgacaggcgt cgcgggtcgc    17640
gaccagcgcc tcgcgagctt ctcgcatgt cgcgacgcgt cttctgcctt ggaatgcgaa      17700
aaaatgcctc ggcggtttta tatccgttgt gatgcttgt tgatcatttt aatgactttt      17760
aaggtctttt aatcagtaga ttaaaggcct ttgatgagtg attaagatgg gggttatgtg    17820
```

```
attaacctct ctagtcaatg aaatgttgat tatgcttata taacctttgg attcctatga   17880
gtgaggagtt agaagaaaat cagaattttc tatactctct caaaagtctt cttgcttagc   17940
ttaagagaaa ccttgcaatc ttctcttgag tgttcttcac aaacacaaaa cacaagttct   18000
tgttgattca cttagaagat catctaagtg gattgtttct ctccattgta tctcattagt   18060
tatttcgtgt taacccggtg atcctagagg ggcgaaatta aactaattgg aaagcgtagt   18120
ttccgtgcct tggagtggga tatccggttc tctcattgat cacaagccta acataagggt   18180
cgggtctggg tccaaatttt aagacccgga cccggaccct aaaaaattca cttggaccca   18240
gacccggacc cggactctta gggtctgaaa aagttggacc caaaccctta aattagggtc   18300
gggtccaaca gggtccgggt agggtcttgg acccatgccc atccctagtg attgggtagc   18360
ccattgcaga atattgagaa cgcaatataa aggggtgttg agaaagaggg ttttgagtgt   18420
attgtttaag aaagttggga aaggaatgag agatgaagta cagaagaaaa cgtctagaaa   18480
gtgaagcatg gggagtctgtt tcttttcttt ttcctaaagt ttcccaccaa atgtccctta   18540
agtggttcag ccacgccttt ggacaagctt accaccaagc tccccatccc agatcatatt   18600
tgaatcaaac atctttcttt ttttagaata ttctttttttt gtgcatgaaa gccaattcca   18660
tgagatatgt accttatatt tctctaaaat atataaataa ttgatgaagc aattttcaga   18720
tcattagata agcgttctac aaaagaacca tcttttttg cttccttgtg tacttggaaa   18780
atgtagttcc catatataat tttaccatgg cagtacttct atagaccact aagttcttcg   18840
cttgtgcaac ctatagtgca tttaagaggg tttaggtata gacagccttc actttcaatt   18900
ggttagagtc tacctccagt atcactgaca gaattttcaa taggaacttc tgtcataact   18960
taattcgcag aaagcactaa ctaaacaacc ccttagttct ttagttaagc gcttgattgg   19020
tcacatccag ctttagttt ttagtatgga gatttataaa gtagtatgac ttgagttgaa   19080
tagtgaacgt aagattagac atatttatat agtcgtgtta attttggaaa ctgacaggag   19140
tgactagaaa ccactttttt tgtgtccaaa atttccatat attgttttttt aaaaaaactg   19200
ctaaatcacg atgataacaa acaaacctta cacaggtacc ggaatgatat tgaaacaaat   19260
tgaggttagt gataagccat aatcccttac cttgaaattc agaggctgtc tgctgcagtc   19320
tctatcatct tcttatttca ctaaatcaat tattacctgc ttcaacctca acggtccgag   19380
gcttagacat tgtgtctttg atagtatcat cacagctgaa aattaatgtg actttcttc   19440
tatttaaata ccatttgaga gtgcctttgg tagtcattat gaatgtcgtg agatcacaat   19500
ccgtgaaata tagttttcat cacattctta cctgcatgtg taaggaaaag tatagcgtta   19560
gtgttcaatc ttttgctact tctggtgact ggtcaatggt caaagtatgc agcatgattt   19620
tgtgtttgtc agtttcttct ttaaataagt gtgaactgct ctagtctaag ttgctcgaac   19680
tcttaaaaag tgttggactt gttagttgtt acatgtatac aatgttgatt gggtgggctt   19740
ttccatatat tattatattt gttgaatcac aatgaagtac ctatttccat ttgaggagta   19800
ggtatgatga ggttagtagg gagtttgagt gttaaaggtt atgtgaagat gtaaaaattc   19860
actgacaatg agaccttagt atccgacggt cggaatttta ccaatttat tgccttgtta   19920
cctttctatt tttacttagt atttccttt cataaattt tgtgatctag agttcatgga   19980
caaaaagggc tgcagaagtt gagagccccc aaccacagtc tacatgggag caagcaactg   20040
atccacctga tagcacttgt gctcaggtca tttatccaat gtctgaggca tttgccagca   20100
gctggatgcc tggatccatg caggaacttg atggacagga tcatcaatat ggtatgtggt   20160
actgtatttg atagaagtta caataatgtg taaactgaaa ccacttaatg acctagtatc   20220
```

```
catctgtatc agacaatgtc ccaatgggaa aggatttgga gattggagta cctagaattt    20280
cagattcacg gctaaatgga ccaaacaaaa cggttaagtt agcaactact gctgaggaaa    20340
accaatattc acagttagac ctcaaccagg aaaatgatgg tcgaagtttt gatgaagaga    20400
acctggagat gaataatgat aaacctaaaa gtgagtggta taaacaggct atgaactcac    20460
caggaaaagt tgaagaacat cgtagaggaa ataaagtatc tgatgcacca cccgaaattt    20520
ccaaaataaa ggacaaaggc atgcaacatg tcgaggatat gccttctctt gtgctcagtc    20580
tgaagaggtt gggtgatatt gcagacacga gcactaatgt ctcagaccag aatattgttg    20640
ggcgttcaga gctttcagcc ttcaccaggt atgctagaga aggtgaaact tgaatttata    20700
taatggacaa gtggacaata tctcattttt aaattgttgc aggtacaatt caggcacaac    20760
tggtaaccag ggtcaaacag gtaatgttgg cagttgctct ccaccaaata atagttcaga    20820
agcagcaaag cagtcccatt ttgatgctcc acatcaaatt tcgaatagca gtagtaacaa    20880
taacaatatg ggctctacta ctaataagtt cttcaaaaag cctgctatgg acattgataa    20940
gacacctgca aaatcaacag tcaactgttc tcatcattca catgtgtttg agccagtgca    21000
aagttcccat atgtctaata taaccttac tgcatctggt aagcctggtg ttggctccgt    21060
aaatggtatg ctgcaagaaa acgtaccagt aaatgctgtt ctgccgcaag aaaataacgt    21120
ggatcagcag ctcaagattc agcaccacca tcactaccat cattacgatg tccatagtgt    21180
acagcagcta ccaaaggttt ctgttcaaca taatatgccc aaaagcaagg atgtgacagc    21240 accccccacag tgtgggtctt caaacacttg tagatcgcca attgaagcaa atgttgccaa    21300
ttgcagtttg aatggaagtg gtagtggaag caatcatggg agcaatttcc ttaatggaag    21360
tagtgctgct gtgaatgttg aaggaacaaa catggtcaat gatagtggga tagctgcaaa    21420
agatggtgct gaaaatggaa gtggtagtgg aagtggaagt ggtagtggta gtggtgttgg    21480
tgtggatcaa agtcgatcag ctcaacgaga agctgccttg aataaattcc gtctcaagcg    21540
taaagaaaga tgctttgaca aaaaggtaat actccaaatt ctctccagaa tgtttatact    21600
tggacatcta gtatgtacat ccttgaatct aaactgtaaa agctgaattt cagaataaaa    21660
aacacaaatt atatcaagta tgaaggcaga gtattgtagt aattatagtt tttctggtat    21720
ggaattagta cttacattta ccagaagcct gctgtcacaa gccataattt gatcatcaag    21780
caacaataat ttggccattt cttgcttgta ttgaaagtga gatgacttca aacttatttg    21840
tgtatcatca catcaggtgc gatatcaaag cagaagaag ttagcagatc aaagacctcg    21900
tgttcgtggg caattcgtgc gccaggtacg agaaaacaaa ggaaggaata ccgatagcta    21960
acaccaattc tttccacaag ttgctgccaa gatcatttat gccactctga tgtcagctgt    22020
cttcatatgt acaaatttcg aatttatgt gtgcatgagg tgctaaatac tgtcaaacct    22080
cagtgattct gtttggttta ggctgtagaa agacatcttt tcctttgtgt tttcatggtt    22140
cttattttga gctgtgttca ctactttta taacatggta gccctggtt gcctttggaa    22200 ataagctttt ccttaaaggt gtgatgcata taatcttgtt tggtgttaga ttatatgatc    22260
atttcttcag gcgtttacgg gtcacatttt ccggaatcct ttcaaacgcg attccggaaa    22320
caatggctca tattttcttt tggtttcaag gagaaggcta tttaaaacag aaaagattta    22380
ggttacagaa atcagtgatg aagcaatgag tttcattata gaataggtag aagtaggggg    22440
tgttttttcc gtactcttga gatagaaagt ggggatagat tctttggact cgtcagaaag    22500
gaataatata gttgtctacc ttttcattt ttagttcttg taggagtttt attccacttc    22560
```

-continued

```
cattttttgta aaatttagga gttgtaagga cgtgtaaaga gaatctgcca tccagatttt    22620
aaccgacggt aaatttgttc ttttcatgtt ttctcaagta actataatgt tttcatcgaa    22680
tctataggga ttttctaatg tgtacctgat agaggcacac agtaacaata atataagtac    22740
atatattctt taagaataat gacatagtaa ttatatttt aatacaaata aaagatgtcc    22800
ttatgtaatg aaacaaataa cttttccttg aaggtatgcc ataattaatt actttatttt    22860
gaagatattt tatatttagt ttgggtagtg gaactactaa ataaaaatat ggttatagta    22920
acatgtactc atgtgcgaac cgaaaaaaac cctatgcttt ctctaaaagt tcccaaaccc    22980
ttgagcttat agccccgacg gcccagcgca ggcttgctgg agcgccgcgt cgctcaccct    23040
gtcgccgacg agcctgcatg tcgtatcgtt cggtcttctg aaggtttagt tttccctgtt    23100
cctctttgtg ttattcatcg ttcccatccc ccatgtctcc ccttcccctg tcagtggttg    23160
tcggcctccc cttcccctat taatggttgt cggcctcccc ttcccttttcc cctaatagtg    23220
gttgttggtc tccccttccc ctttcatgtt gtcaagttgt tcctttcccc gttctcccctt    23280
ttcctagtcc tcttttggtg ttcttgttgt tgttagttta gtggctttgg ttggttagtt    23340
cggctgagtg cttcgtcgtc gtatgcccctt ccttgttccc ctatttggtt ttggttatgt    23400
tggggtttcg gttaacccccg ttcccatgct taaacgtggg agggcctcag gatttagata    23460
taaaggtcat cattctcgcg cttagacgtg agagggatta agtgttcagg gataagggct    23520
ccgttcctgc gcttaaacgt gggagaactt aaaggttcta ggttttacag gagttttggg    23580
attggaaagt atatgaactc tgtttggcag aagatgacag tgcaatgtgg ggattaatca    23640
tttcgttttc ttcctttta ataagttagt ctcttattat gagagttttc tattagttct    23700
aatccccttta atttcttgta gggggttgtaa gtctagtttg tcgttgttta gtatatctag    23760
ttcgagaagc tcgaaagttt gaggttgtgg aaaaatgtac ttactggttg cagatcaaga    23820
atattaagac gaatgtttga cttcaattta ctattgcatc aggtaggaaa tatggtgagt    23880
catcgaatat ccattatggt tggaatagta ccatatcatg gaagcggttt cgaagcgtgt    23940
atattagtaa aatagatgaa gatattcaaa tcgatgtttt agattatctt ttatgtacgt    24000
aagggtcatt attgttgtag atgttgtatg gttttttaat ttaatgataa tttttccttta    24060
ttcccactta aaagtaaaca atgcattcat gtgcacatat tagtacatat atttgtatat    24120
acatctcg                                                                24128
```

<210> SEQ ID NO 9
<211> LENGTH: 2367
<212> TYPE: DNA
<213> ORGANISM: Beta vulgaris

<400> SEQUENCE: 9

```
atgaggttga ttcacaaaaa tgaagatggg cccggtgttg ccaagtcggt ggcagagctt      60
aatcaacata tagttgctgt gaaaaaagaa ggtaggggta gggttgcagg tgaagggcag     120
gggctttccg aggaggacga actgagaatt attgaggatg tgaagatgc aaacagcagg     180
cgttctttga gttctgttca gcttccagtt catactcaca ggcatcagcc acaagtacaa     240
ccccagggga gagtctgttg ggagaggttt ctccctgttg gatctcctaa ggttttgctc     300
gtagaaagtg atgactcaac tcgtcatatt gttagtgctt tgctacggaa atgtagctat     360
gaagttgtag gggtgccaaa tggcatagaa gcatggaaaa tcttagaaga tttgagcaat     420
cagattgacc tagtttttaac tgaggtagtc acatcaggac tctctggtat aggtcttctg     480
tccaagataa tgagtcacaa aagctgccag aatactcctg tcattatgat gtcatctcat     540
```

```
gattcgatgg gtttagtctt aaagtgctta tccaagggcg ctgttgactt tctggtgaag      600
cctataagaa aaaacgaact taaaaacctt tggcagcatg tttggaggag gtgtcacagt      660
tctagtggta gtggaagtga agctgtgta aggaatggaa atccatagg aagcaagagg        720 gctgaagagt cggacaatga cactgacatc aatgaggaag atgataacag aagcattggt      780
ttacaagctc gggatggaag tgacaatgga agtgggaccc agagttcatg gacaaaaagg      840
gctgcagaag ttgagagccc ccaaccacag tctacatggg agcaagcaac tgatccacct      900
gatagcactt gtgctcaggt catttatcca atgtctgagg catttgccag cagctggatg      960
cctggatcca tgcaggaact tgatggacag gatcatcaat atgacaatgt cccaatggga    1020
aaggatttgg agattggagt acctagaatt tcagattcac ggctaaatgg accaaacaaa    1080
acggttaagt tagcaactac tgctgaggaa accaatatt cacagttaga cctcaaccag     1140
gaaaatgatg gtcgaagttt tgatgaagag aacctggaga tgaataatga taaacctaaa    1200
agtgagtgga ttaaacaggc tatgaactca ccaggaaaag ttgaagaaca tcgtagagga    1260
aataaagtat ctgatgcacc acccgaaatt tccaaaataa aggacaaagg catgcaacat    1320
gtcgaggata tgccttctct tgtgctcagt ctgaagaggt tgggtgatat tgcagacacg    1380
agcactaatg tctcagacca gaatattgtt gggcgttcag agctttcagc cttcaccagg    1440
tacaattcag gcacaactgg taaccagggt caaacaggta atgttggcag ttgctctcca    1500
ccaaataata gttcagaagc agcaaagcag tcccattttg atgctccaca tcaaatttcg    1560
aatagcagta gtaacaataa caatatgggc tctactacta ataagttctt caaaaagcct    1620
gctatggaca ttgataagac acctgcaaaa tcaacagtca actgttctca tcattcacat    1680
gtgtttgagc cagtgcaaag ttcccatatg tctaataata accttactgc atctggtaag    1740
cctggtgttg gctccgtaaa tggtatgctg caagaaaacg taccagtaaa tgctgttctg    1800
ccgcaagaaa ataacgtgga tcagcagctc aagattcagc accaccatca ctaccatcat    1860
tacgatgtcc atagtgtaca gcagctacca aaggtttctg ttcaacataa tatgcccaaa    1920
agcaaggatg tgacagcacc cccacagtgt gggtcttcaa acacttgtag atcgccaatt    1980
gaagcaaatg ttgccaattg cagtttgaat ggaagtggta gtggaagcaa tcatgggagc    2040
aatttcctta atggaagtag tgctgctgtg aatgttgaag aacaaacat ggtcaatgat     2100 agtgggatag ctgcaaaaga tggtgctgaa atggaagtg gtagtggaag tggaagtggt     2160
agtggtagtg gtgttggtgt ggatcaaagt cgatcagctc aacgagaagc tgccttgaat    2220
aaattccgtc tcaagcgtaa agaaagatgc tttgacaaaa aggtgcgata tcaaagcaga    2280
aagaagttag cagatcaaag acctcgtgtt cgtgggcaat tcgtgcgcca ggtacgagaa    2340
aacaaaggaa ggaataccga tagctaa                                        2367
```

<210> SEQ ID NO 10
<211> LENGTH: 2367
<212> TYPE: DNA
<213> ORGANISM: Beta vulgaris

<400> SEQUENCE: 10

```
atgaggttga ttcacaaaaa tgaagatggg cccggtgttg ccaagtcggt ggcagagctt       60
aatcaacata tagttgctgt gaaaaaagaa ggtaggggta gggttgcagg tgaagggcag      120 gggcttttccg aggaggacga actgagaatt attgaggatg tgaagatgc aaacagcagg     180 cgttctttga gttctgttca gcttccagtt catactcaca ggcctcagcc acaagtacaa      240
```

```
ccccagggga gagtctgttg ggagaggttt ctccctgttg gatctcctaa ggttttgctc    300
gtagaaagtg atgactcaac tcgtcatatt gttagtgctt tgctacggaa ttgtagctat    360
gaagttgtag gggtgccaaa tggcatagaa gcatggaaaa tcttagaaga tttgagcaat    420
cagattgacc tagttttaac tgaggtagtc acatcaggac tctctggtat aggtcttctg    480
tccaagataa tgagtcacaa aagctgccag aatactcctg tcattatgat gtcatctcat    540
gattcgatgg gtttagtctt aaagtgctta tccaagggcg ctgttgactt tctggtgaag    600
cctataagaa aaaatgaact taaaaacctt tggcagcatg tttggaggag gtgtcacagt    660
tctagtggta gtggaagtga aagctgtgta aggaatggaa atccataggg aagcaagagg    720
gctgaagagt cggacaatga cactgacagc aatgaggaag atgataacag aagcattggt    780
ttacaagctc gggatggaag tgacaatgga agtgggaccc agagttcatg gacaaaaagg    840
gctgcagaag ttgagagccc ccaaccacag tctacatggg agcaagcaac tgatccgcct    900
gatagcactt gtgctcaggt catttatcca atgtctgagg catttgccag cagctggatg    960
cctggatcca tgcaggaact tgatgtacag gatcatcaat atgacaatgt cccaatggga   1020
aaggatttgg agattggagt acctagaatt tcagattcac ggctaaatgg accaaacaaa   1080
aaggttaagt tagcaactac tgctgaggaa accaatatt cacagttaga cctcaaccag    1140
gaaaatgatg gtcgaagttt tgatgaagag aacctggaga tgaataatga taaacctaaa   1200
agtgagtgga ttaaacaggc tatgaactca ccaggaaaag ttgaagaaca tcatagagga   1260
aataaagtat ctgatgcacc acccgaaatt tccaaaataa aggacaaagg catgcaacat   1320
gtcgaggata tgccttctct tgtgctcagt ctgaagaggt tgggtgatat tgcagacacg   1380
agcactaatg tctcagacca gaatattgtt gggcgttcag agctttcagc cttcaccagg   1440
tacaattcag gcacaactgg taaccagggt caaacaggta atgttggcag ttgctctcca   1500
ccaaataata gttcagaagc agcaaagcag tcccattttg atgctccaca tcaaatttcg   1560
aatagcagta gtaacaataa caatatgggc tctactacta ataagttctt caaaaagcct   1620
gctatggaca ttgataagac acctgcaaaa tcaacagtca actgttctca tcattcacat   1680
gtgtttgagc cagtgcaaag ttcccatatg tctaataata accttactgc atctggtaag   1740
cctggtgttg gctccgtaaa tggtatgctg caagaaaacg taccagtaaa tgctgttctg   1800
ccgcaagaaa ataacgtgga tcagcagctc aagattcagc gccaccatca ctaccatcat   1860
tacgatgtcc ataatgtaca gcagctacca aaggtttctg ttcaacataa tatgtccaaa   1920
agcaaggat tgcacagcacc cccacagtgt gggtcttcaa acacttgtag atcgccaatt    1980
aaagcaaatg ttgccaattg cagtttgaat ggaagtggta gtggaagcaa tcatgggagc   2040
aatttcctta tggaagtag tgctgctgtg aatgttgaag aacaaacat ggtcaatgat     2100
agtgggatag ctgcaaaaga tggtactgaa aatggaagtg gtagtggaag tggaagtggt   2160
agtggtagtg gtgttggtgt ggatcaaagt cgatcagctc aacgagaagc tgccttgaat   2220
aaattccgtc tcaagcgtaa agaaagatgc tttgacaaaa aggtgcgata tcaaagcaga   2280
aagaagttag cagatcaaag acctcgtgtt cgtgggcaat tcgtgcgcca ggtgcgagaa   2340
aacaaaggaa ggaataccga tagctaa                                      2367

<210> SEQ ID NO 11
<211> LENGTH: 788
<212> TYPE: PRT
<213> ORGANISM: Beta vulgaris

<400> SEQUENCE: 11
```

-continued

```
Met Arg Leu Ile His Lys Asn Glu Asp Gly Pro Gly Val Ala Lys Ser
1               5                   10                  15

Val Ala Glu Leu Asn Gln His Ile Val Ala Val Lys Lys Glu Gly Arg
            20                  25                  30

Gly Arg Val Ala Gly Glu Gly Gln Gly Leu Ser Glu Glu Asp Glu Leu
        35                  40                  45

Arg Ile Ile Glu Asp Gly Glu Asp Ala Asn Ser Arg Arg Ser Leu Ser
50                  55                  60

Ser Val Gln Leu Pro Val His Thr His Arg His Gln Pro Gln Val Gln
65              70                  75                  80

Pro Gln Gly Arg Val Cys Trp Glu Arg Phe Leu Pro Val Gly Ser Pro
                85                  90                  95

Lys Val Leu Leu Val Glu Ser Asp Asp Ser Thr Arg His Ile Val Ser
            100                 105                 110

Ala Leu Leu Arg Lys Cys Ser Tyr Glu Val Val Gly Val Pro Asn Gly
        115                 120                 125

Ile Glu Ala Trp Lys Ile Leu Glu Asp Leu Ser Asn Gln Ile Asp Leu
    130                 135                 140

Val Leu Thr Glu Val Val Thr Ser Gly Leu Ser Gly Ile Gly Leu Leu
145                 150                 155                 160

Ser Lys Ile Met Ser His Lys Ser Cys Gln Asn Thr Pro Val Ile Met
                165                 170                 175

Met Ser Ser His Asp Ser Met Gly Leu Val Leu Lys Cys Leu Ser Lys
            180                 185                 190

Gly Ala Val Asp Phe Leu Val Lys Pro Ile Arg Lys Asn Glu Leu Lys
        195                 200                 205

Asn Leu Trp Gln His Val Trp Arg Arg Cys His Ser Ser Ser Gly Ser
    210                 215                 220

Gly Ser Glu Ser Cys Val Arg Asn Gly Lys Ser Ile Gly Ser Lys Arg
225                 230                 235                 240

Ala Glu Glu Ser Asp Asn Asp Thr Asp Ile Asn Glu Glu Asp Asp Asn
                245                 250                 255

Arg Ser Ile Gly Leu Gln Ala Arg Asp Gly Ser Asp Asn Gly Ser Gly
            260                 265                 270

Thr Gln Ser Ser Trp Thr Lys Arg Ala Ala Glu Val Glu Ser Pro Gln
        275                 280                 285

Pro Gln Ser Thr Trp Glu Gln Ala Thr Asp Pro Pro Asp Ser Thr Cys
    290                 295                 300

Ala Gln Val Ile Tyr Pro Met Ser Glu Gly Ala Phe Ala Ser Ser Trp Met
305                 310                 315                 320

Pro Gly Ser Met Gln Glu Leu Asp Gly Gln Asp His Gln Tyr Asp Asn
                325                 330                 335

Val Pro Met Gly Lys Asp Leu Glu Ile Gly Val Pro Arg Ile Ser Asp
            340                 345                 350

Ser Arg Leu Asn Gly Pro Asn Lys Thr Val Lys Leu Ala Thr Thr Ala
        355                 360                 365

Glu Glu Asn Gln Tyr Ser Gln Leu Asp Leu Asn Gln Glu Asn Asp Gly
    370                 375                 380

Arg Ser Phe Asp Glu Glu Asn Leu Glu Met Asn Asn Asp Lys Pro Lys
385                 390                 395                 400

Ser Glu Trp Ile Lys Gln Ala Met Asn Ser Pro Gly Lys Val Glu Glu
                405                 410                 415
```

His Arg Arg Gly Asn Lys Val Ser Asp Ala Pro Pro Glu Ile Ser Lys
                420                 425                 430

Ile Lys Asp Lys Gly Met Gln His Val Glu Asp Met Pro Ser Leu Val
            435                 440                 445

Leu Ser Leu Lys Arg Leu Gly Asp Ile Ala Asp Thr Ser Thr Asn Val
        450                 455                 460

Ser Asp Gln Asn Ile Val Gly Arg Ser Glu Leu Ser Ala Phe Thr Arg
465                 470                 475                 480

Tyr Asn Ser Gly Thr Thr Gly Asn Gln Gly Gln Thr Gly Asn Val Gly
                485                 490                 495

Ser Cys Ser Pro Pro Asn Asn Ser Ser Glu Ala Ala Lys Gln Ser His
            500                 505                 510

Phe Asp Ala Pro His Gln Ile Ser Asn Ser Ser Ser Asn Asn Asn Asn
        515                 520                 525

Met Gly Ser Thr Thr Asn Lys Phe Phe Lys Lys Pro Ala Met Asp Ile
    530                 535                 540

Asp Lys Thr Pro Ala Lys Ser Thr Val Asn Cys Ser His His Ser His
545                 550                 555                 560

Val Phe Glu Pro Val Gln Ser Ser His Met Ser Asn Asn Asn Leu Thr
                565                 570                 575

Ala Ser Gly Lys Pro Gly Val Gly Ser Val Asn Gly Met Leu Gln Glu
            580                 585                 590

Asn Val Pro Val Asn Ala Val Leu Pro Gln Glu Asn Asn Val Asp Gln
        595                 600                 605

Gln Leu Lys Ile Gln His His His Tyr His Tyr Asp Val His
610                 615                 620

Ser Val Gln Gln Leu Pro Lys Val Ser Val Gln His Asn Met Pro Lys
625                 630                 635                 640

Ser Lys Asp Val Thr Ala Pro Pro Gln Cys Gly Ser Ser Asn Thr Cys
                645                 650                 655

Arg Ser Pro Ile Glu Ala Asn Val Ala Asn Cys Ser Leu Asn Gly Ser
            660                 665                 670

Gly Ser Gly Ser Asn His Gly Ser Asn Phe Leu Asn Gly Ser Ser Ala
        675                 680                 685

Ala Val Asn Val Glu Gly Thr Asn Met Val Asn Asp Ser Gly Ile Ala
    690                 695                 700

Ala Lys Asp Gly Ala Glu Asn Gly Ser Gly Ser Gly Ser Gly Ser Gly
705                 710                 715                 720

Ser Gly Ser Gly Val Gly Val Asp Gln Ser Arg Ser Ala Gln Arg Glu
                725                 730                 735

Ala Ala Leu Asn Lys Phe Arg Leu Lys Arg Lys Glu Arg Cys Phe Asp
            740                 745                 750

Lys Lys Val Arg Tyr Gln Ser Arg Lys Lys Leu Ala Asp Gln Arg Pro
        755                 760                 765

Arg Val Arg Gly Gln Phe Val Arg Gln Val Arg Glu Asn Lys Gly Arg
    770                 775                 780

Asn Thr Asp Ser
785

<210> SEQ ID NO 12
<211> LENGTH: 788
<212> TYPE: PRT
<213> ORGANISM: Beta vulgaris

<400> SEQUENCE: 12

-continued

```
Met Arg Leu Ile His Lys Asn Glu Asp Gly Pro Gly Val Ala Lys Ser
1               5                  10                 15

Val Ala Glu Leu Asn Gln His Ile Val Ala Val Lys Lys Glu Gly Arg
            20                  25                 30

Gly Arg Val Ala Gly Glu Gly Gln Gly Leu Ser Glu Glu Asp Glu Leu
        35                  40                 45

Arg Ile Ile Glu Asp Gly Glu Asp Ala Asn Ser Arg Arg Ser Leu Ser
50                  55                  60

Ser Val Gln Leu Pro Val His Thr His Arg Pro Gln Pro Gln Val Gln
65                  70                  75                 80

Pro Gln Gly Arg Val Cys Trp Glu Arg Phe Leu Pro Val Gly Ser Pro
                85                  90                 95

Lys Val Leu Leu Val Glu Ser Asp Asp Ser Thr Arg His Ile Val Ser
            100                 105                110

Ala Leu Leu Arg Asn Cys Ser Tyr Glu Val Val Gly Val Pro Asn Gly
        115                 120                125

Ile Glu Ala Trp Lys Ile Leu Glu Asp Leu Ser Asn Gln Ile Asp Leu
130                 135                 140

Val Leu Thr Glu Val Val Thr Ser Gly Leu Ser Gly Ile Gly Leu Leu
145                 150                 155                160

Ser Lys Ile Met Ser His Lys Ser Cys Gln Asn Thr Pro Val Ile Met
                165                 170                175

Met Ser Ser His Asp Ser Met Gly Leu Val Leu Lys Cys Leu Ser Lys
            180                 185                190

Gly Ala Val Asp Phe Leu Val Lys Pro Ile Arg Lys Asn Glu Leu Lys
        195                 200                 205

Asn Leu Trp Gln His Val Trp Arg Arg Cys His Ser Ser Ser Gly Ser
210                 215                 220

Gly Ser Glu Ser Cys Val Arg Asn Gly Lys Ser Ile Gly Ser Lys Arg
225                 230                 235                240

Ala Glu Glu Ser Asp Asn Asp Thr Asp Ser Asn Glu Glu Asp Asp Asn
                245                 250                255

Arg Ser Ile Gly Leu Gln Ala Arg Asp Gly Ser Asp Asn Gly Ser Gly
            260                 265                270

Thr Gln Ser Ser Trp Thr Lys Arg Ala Ala Glu Val Glu Ser Pro Gln
        275                 280                 285

Pro Gln Ser Thr Trp Glu Gln Ala Thr Asp Pro Pro Asp Ser Thr Cys
290                 295                 300

Ala Gln Val Ile Tyr Pro Met Ser Glu Gly Ala Phe Ala Ser Ser Trp Met
305                 310                 315                320

Pro Gly Ser Met Gln Glu Leu Asp Val Gln Asp His Gln Tyr Asp Asn
                325                 330                335

Val Pro Met Gly Lys Asp Leu Glu Ile Gly Val Pro Arg Ile Ser Asp
            340                 345                350

Ser Arg Leu Asn Gly Pro Asn Lys Val Lys Leu Ala Thr Thr Ala
        355                 360                 365

Glu Glu Asn Gln Tyr Ser Gln Leu Asp Leu Asn Gln Glu Asn Asp Gly
370                 375                 380

Arg Ser Phe Asp Glu Glu Asn Leu Glu Met Asn Asn Asp Lys Pro Lys
385                 390                 395                400

Ser Glu Trp Ile Lys Gln Ala Met Asn Ser Pro Gly Lys Val Glu Glu
                405                 410                415
```

His His Arg Gly Asn Lys Val Ser Asp Ala Pro Pro Glu Ile Ser Lys
                420                 425                 430

Ile Lys Asp Lys Gly Met Gln His Val Glu Asp Met Pro Ser Leu Val
            435                 440                 445

Leu Ser Leu Lys Arg Leu Gly Asp Ile Ala Asp Thr Ser Thr Asn Val
        450                 455                 460

Ser Asp Gln Asn Ile Val Gly Arg Ser Glu Leu Ser Ala Phe Thr Arg
465                 470                 475                 480

Tyr Asn Ser Gly Thr Thr Gly Asn Gln Gly Gln Thr Gly Asn Val Gly
                485                 490                 495

Ser Cys Ser Pro Pro Asn Asn Ser Ser Glu Ala Ala Lys Gln Ser His
            500                 505                 510

Phe Asp Ala Pro His Gln Ile Ser Asn Ser Ser Ser Asn Asn Asn Asn
        515                 520                 525

Met Gly Ser Thr Thr Asn Lys Phe Phe Lys Lys Pro Ala Met Asp Ile
        530                 535                 540

Asp Lys Thr Pro Ala Lys Ser Thr Val Asn Cys Ser His His Ser His
545                 550                 555                 560

Val Phe Glu Pro Val Gln Ser Ser His Met Ser Asn Asn Asn Leu Thr
                565                 570                 575

Ala Ser Gly Lys Pro Gly Val Gly Ser Val Asn Gly Met Leu Gln Glu
            580                 585                 590

Asn Val Pro Val Asn Ala Val Leu Pro Gln Glu Asn Val Asp Gln
        595                 600                 605

Gln Leu Lys Ile Gln Arg His His Tyr His Tyr Asp Val His
610                 615                 620

Asn Val Gln Gln Leu Pro Lys Val Ser Val Gln His Asn Met Ser Lys
625                 630                 635                 640

Ser Lys Asp Val Thr Ala Pro Pro Gln Cys Gly Ser Ser Asn Thr Cys
                645                 650                 655

Arg Ser Pro Ile Lys Ala Asn Val Ala Asn Cys Ser Leu Asn Gly Ser
            660                 665                 670

Gly Ser Gly Ser Asn His Gly Ser Asn Phe Leu Asn Gly Ser Ser Ala
        675                 680                 685

Ala Val Asn Val Glu Gly Thr Asn Met Val Asn Asp Ser Gly Ile Ala
        690                 695                 700

Ala Lys Asp Gly Thr Glu Asn Gly Ser Gly Ser Gly Ser Gly Ser Gly
705                 710                 715                 720

Ser Gly Ser Gly Val Gly Val Asp Gln Ser Arg Ser Ala Gln Arg Glu
                725                 730                 735

Ala Ala Leu Asn Lys Phe Arg Leu Lys Arg Lys Glu Arg Cys Phe Asp
            740                 745                 750

Lys Lys Val Arg Tyr Gln Ser Arg Lys Lys Leu Ala Asp Gln Arg Pro
        755                 760                 765

Arg Val Arg Gly Gln Phe Val Arg Gln Val Arg Glu Asn Lys Gly Arg
        770                 775                 780

Asn Thr Asp Ser
785

<210> SEQ ID NO 13
<211> LENGTH: 23
<212> TYPE: DNA
<213> ORGANISM: Artificial
<220> FEATURE:
<223> OTHER INFORMATION: oligonucleotide sequence - Primer PRR7(T1)-F

```
<400> SEQUENCE: 13
gaggtgtcac agtgtaagtg tct                                              23

<210> SEQ ID NO 14
<211> LENGTH: 25
<212> TYPE: DNA
<213> ORGANISM: Artificial
<220> FEATURE:
<223> OTHER INFORMATION: oligonucleotide sequence - Primer PRR7(T1)-R

<400> SEQUENCE: 14
aaagactgct acacgaacca ctaag                                            25

<210> SEQ ID NO 15
<211> LENGTH: 14
<212> TYPE: DNA
<213> ORGANISM: Artificial
<220> FEATURE:
<223> OTHER INFORMATION: oligonucleotide sequence - Probe PRR7(T1)-VIC

<400> SEQUENCE: 15
ctgatggaaa gctg                                                        14

<210> SEQ ID NO 16
<211> LENGTH: 14
<212> TYPE: DNA
<213> ORGANISM: Artificial
<220> FEATURE:
<223> OTHER INFORMATION: oligonucleotide sequence - Probe PRR7(T1)-FAM

<400> SEQUENCE: 16
ctgatgaaaa gctg                                                        14

<210> SEQ ID NO 17
<211> LENGTH: 23
<212> TYPE: DNA
<213> ORGANISM: Artificial
<220> FEATURE:
<223> OTHER INFORMATION: oligonucleotide sequence - Primer GJ131(T1)-F

<400> SEQUENCE: 17
gcccgtacaa acaaagactt ctc                                              23

<210> SEQ ID NO 18
<211> LENGTH: 24
<212> TYPE: DNA
<213> ORGANISM: Artificial
<220> FEATURE:
<223> OTHER INFORMATION: oligonucleotide sequence - Primer GJ131(T1)-R

<400> SEQUENCE: 18
acgcagaatg ttgatgatga taca                                             24

<210> SEQ ID NO 19
<211> LENGTH: 18
<212> TYPE: DNA
<213> ORGANISM: Artificial
<220> FEATURE:
<223> OTHER INFORMATION: oligonucleotide sequence - Probe GJ131(T1)-VIC

<400> SEQUENCE: 19
tccatctctc cacagctt                                                    18

<210> SEQ ID NO 20
```

```
<211> LENGTH: 17
<212> TYPE: DNA
<213> ORGANISM: Artificial
<220> FEATURE:
<223> OTHER INFORMATION: oligonucleotide sequence - Probe GJ131(T1)-FAM

<400> SEQUENCE: 20
tccatctccc cacagct                                                17

<210> SEQ ID NO 21
<211> LENGTH: 30
<212> TYPE: DNA
<213> ORGANISM: Artificial
<220> FEATURE:
<223> OTHER INFORMATION: oligonucleotide sequence - Primer ED031700(T1)-
      F

<400> SEQUENCE: 21
taaaggtggt aattttagag aattttagga                                  30

<210> SEQ ID NO 22
<211> LENGTH: 22
<212> TYPE: DNA
<213> ORGANISM: Artificial
<220> FEATURE:
<223> OTHER INFORMATION: oligonucleotide sequence - Primer 031700(T1)-R

<400> SEQUENCE: 22
gctcgttttg aaaaaatttg gg                                          22

<210> SEQ ID NO 23
<211> LENGTH: 18
<212> TYPE: DNA
<213> ORGANISM: Artificial
<220> FEATURE:
<223> OTHER INFORMATION: oligonucleotide sequence - Probe ED031700(T1)-
      VIC

<400> SEQUENCE: 23
tttaattcgc atccttct                                               18

<210> SEQ ID NO 24
<211> LENGTH: 17
<212> TYPE: DNA
<213> ORGANISM: Artificial
<220> FEATURE:
<223> OTHER INFORMATION: oligonucleotide sequence - Probe ED031700(T1)-
      FAM

<400> SEQUENCE: 24
ttaattcgca aacttct                                                17

<210> SEQ ID NO 25
<211> LENGTH: 27
<212> TYPE: DNA
<213> ORGANISM: Artificial
<220> FEATURE:
<223> OTHER INFORMATION: oligonucleotide sequence - Primer 9_27(T2)-F

<400> SEQUENCE: 25
tgccaaaaca cacattgtac ctataca                                     27

<210> SEQ ID NO 26
<211> LENGTH: 19
<212> TYPE: DNA
<213> ORGANISM: Artificial
<220> FEATURE:
```

```
<223> OTHER INFORMATION: oligonucleotide sequence - Primer 9_27(T2)-R

<400> SEQUENCE: 26
tgcctctggc tccttgaag                                                19

<210> SEQ ID NO 27
<211> LENGTH: 18
<212> TYPE: DNA
<213> ORGANISM: Artificial
<220> FEATURE:
<223> OTHER INFORMATION: oligonucleotide sequence - Probe 9_27(T2)-VIC

<400> SEQUENCE: 27
catctctaca acactacc                                                 18

<210> SEQ ID NO 28
<211> LENGTH: 17
<212> TYPE: DNA
<213> ORGANISM: Artificial
<220> FEATURE:
<223> OTHER INFORMATION: oligonucleotide sequence - 9_27(T2)-FAM

<400> SEQUENCE: 28
atctctacaa gactacc                                                  17

<210> SEQ ID NO 29
<211> LENGTH: 22
<212> TYPE: DNA
<213> ORGANISM: Artificial
<220> FEATURE:
<223> OTHER INFORMATION: oligonucleotide sequence - Primer GJ01(T1)-F

<400> SEQUENCE: 29
gaacccagga ttactcgtga gc                                            22

<210> SEQ ID NO 30
<211> LENGTH: 33
<212> TYPE: DNA
<213> ORGANISM: Artificial
<220> FEATURE:
<223> OTHER INFORMATION: oligonucleotide sequence - Primer GJ01(T1)-R

<400> SEQUENCE: 30
aaaagtagaa taaaatgtaa cctcctccat ctc                                33

<210> SEQ ID NO 31
<211> LENGTH: 17
<212> TYPE: DNA
<213> ORGANISM: Artificial
<220> FEATURE:
<223> OTHER INFORMATION: oligonucleotide sequence - Probe GJ01(T1)-VIC

<400> SEQUENCE: 31
acgcaagata acatcac                                                  17

<210> SEQ ID NO 32
<211> LENGTH: 17
<212> TYPE: DNA
<213> ORGANISM: Artificial
<220> FEATURE:
<223> OTHER INFORMATION: oligonucleotide sequence - Probe GJ01(T1)-FAM

<400> SEQUENCE: 32
acgcaagata acgtcac                                                  17
```

<210> SEQ ID NO 33
<211> LENGTH: 27
<212> TYPE: DNA
<213> ORGANISM: Artificial
<220> FEATURE:
<223> OTHER INFORMATION: oligonucleotide sequence - Primer SELA3977

<400> SEQUENCE: 33
cgtgtcgaat attgatttac tgagatc                                              27

<210> SEQ ID NO 34
<211> LENGTH: 26
<212> TYPE: DNA
<213> ORGANISM: Artificial
<220> FEATURE:
<223> OTHER INFORMATION: oligonucleotide sequence - Primer SELA3988

<400> SEQUENCE: 34
taacccatca tgtcttttca acaatc                                               26

<210> SEQ ID NO 35
<211> LENGTH: 23
<212> TYPE: DNA
<213> ORGANISM: Artificial
<220> FEATURE:
<223> OTHER INFORMATION: oligonucleotide sequence - Primer SELA4442

<400> SEQUENCE: 35
aagaataccg agagtttttt ccc                                                  23

<210> SEQ ID NO 36
<211> LENGTH: 29
<212> TYPE: DNA
<213> ORGANISM: Artificial
<220> FEATURE:
<223> OTHER INFORMATION: oligonucleotide sequence - Primer SELA3809

<400> SEQUENCE: 36
tcaccaattc tttatatcat atcatgaca                                            29

<210> SEQ ID NO 37
<211> LENGTH: 28
<212> TYPE: DNA
<213> ORGANISM: Artificial
<220> FEATURE:
<223> OTHER INFORMATION: oligonucleotide sequence - Primer SELA3810

<400> SEQUENCE: 37
gagaaaaggg ttttagatgg taagtttt                                             28

<210> SEQ ID NO 38
<211> LENGTH: 28
<212> TYPE: DNA
<213> ORGANISM: Artificial
<220> FEATURE:
<223> OTHER INFORMATION: oligonucleotide sequence - Primer 3807

<400> SEQUENCE: 38
catttgttga agtaggtgat aaggacaa                                             28

<210> SEQ ID NO 39
<211> LENGTH: 21
<212> TYPE: DNA
<213> ORGANISM: Artificial
<220> FEATURE:
<223> OTHER INFORMATION: oligonucleotide sequence - Primer SELA3766

```
<400> SEQUENCE: 39
tttgatgctt ttttcaggcc a                                          21

<210> SEQ ID NO 40
<211> LENGTH: 24
<212> TYPE: DNA
<213> ORGANISM: Artificial
<220> FEATURE:
<223> OTHER INFORMATION: oligonucleotide sequence - Primer SELA3769

<400> SEQUENCE: 40
aatatgtgtg agaaaatggt ggca                                       24

<210> SEQ ID NO 41
<211> LENGTH: 26
<212> TYPE: DNA
<213> ORGANISM: Artificial
<220> FEATURE:
<223> OTHER INFORMATION: oligonucleotide sequence - Primer SELA3857

<400> SEQUENCE: 41
tccatttgag gagtaggtat gatgag                                     26

<210> SEQ ID NO 42
<211> LENGTH: 21
<212> TYPE: DNA
<213> ORGANISM: Artificial
<220> FEATURE:
<223> OTHER INFORMATION: oligonucleotide sequence - Primer SELA3860

<400> SEQUENCE: 42
tcttgagctg ctgatccacg t                                          21

<210> SEQ ID NO 43
<211> LENGTH: 21
<212> TYPE: DNA
<213> ORGANISM: Artificial
<220> FEATURE:
<223> OTHER INFORMATION: oligonucleotide sequence - Primer SELA3861

<400> SEQUENCE: 43
ctgcatctgg taagcctggt g                                          21

<210> SEQ ID NO 44
<211> LENGTH: 20
<212> TYPE: DNA
<213> ORGANISM: Artificial
<220> FEATURE:
<223> OTHER INFORMATION: oligonucleotide sequence - Primer SELA3864

<400> SEQUENCE: 44
aatgtgaccc gtaaacgcct                                            20

<210> SEQ ID NO 45
<211> LENGTH: 24
<212> TYPE: DNA
<213> ORGANISM: Artificial
<220> FEATURE:
<223> OTHER INFORMATION: oligonucleotide sequence- forward Primer for
     BvPRR7 for gene expression analysis

<400> SEQUENCE: 45
ttggaggagg tgtcacagtt ctag                                       24

<210> SEQ ID NO 46
```

```
<211> LENGTH: 22
<212> TYPE: DNA
<213> ORGANISM: Artificial
<220> FEATURE:
<223> OTHER INFORMATION: oligonucleotide sequence- reverse Primer for
      BvPRR7 for gene expression analysis

<400> SEQUENCE: 46
tgtcattgtc cgactcttca gc                                              22

<210> SEQ ID NO 47
<211> LENGTH: 19
<212> TYPE: DNA
<213> ORGANISM: Artificial
<220> FEATURE:
<223> OTHER INFORMATION: oligonucleotide sequence- forward Primer for
      BvlCDH for gene expression analysis

<400> SEQUENCE: 47
cacaccagat gaaggccgt                                                  19

<210> SEQ ID NO 48
<211> LENGTH: 18
<212> TYPE: DNA
<213> ORGANISM: Artificial
<220> FEATURE:
<223> OTHER INFORMATION: oligonucleotide sequence- Reverse Primer for
      BvlCDH for gene expression analysis

<400> SEQUENCE: 48
ccctgaagac cgtgccat                                                   18

<210> SEQ ID NO 49
<211> LENGTH: 25
<212> TYPE: DNA
<213> ORGANISM: Artificial
<220> FEATURE:
<223> OTHER INFORMATION: oligonucleotide sequence - Primer PRR7(T6)-F

<400> SEQUENCE: 49
gctatcggta ttccttcctt tgttt                                           25

<210> SEQ ID NO 50
<211> LENGTH: 19
<212> TYPE: DNA
<213> ORGANISM: Artificial
<220> FEATURE:
<223> OTHER INFORMATION: oligonucleotide sequence - Primer PRR7(T6)-R

<400> SEQUENCE: 50
ctcgtgttcg tgggcaatt                                                  19

<210> SEQ ID NO 51
<211> LENGTH: 16
<212> TYPE: DNA
<213> ORGANISM: Artificial
<220> FEATURE:
<223> OTHER INFORMATION: oligonucleotide sequence - Probe PRR7(T6)-VIC

<400> SEQUENCE: 51
ctcgtacctg gcgcac                                                     16

<210> SEQ ID NO 52
<211> LENGTH: 16
<212> TYPE: DNA
<213> ORGANISM: Artificial
<220> FEATURE:
```

<223> OTHER INFORMATION: oligonucleotide sequence - Probe PRR7(T6)-FAM

<400> SEQUENCE: 52
ctcgcacctg gcgcac  16

<210> SEQ ID NO 53
<211> LENGTH: 3672
<212> TYPE: DNA
<213> ORGANISM: Beta vulgaris

<400> SEQUENCE: 53

| | | | | | |
|---|---|---|---|---|---|
| aaaaaatttc | cataaaggtg | tatttattag | gcgtagcggt | tgatttccca | aatcattatc | 60 |
| cttgcgcaaa | ttgcataatg | gagatatttg | gtgttgacgt | ggggccataa | ccataatagg | 120 |
| gggtcaaaaa | caaaactaca | agggttaaaa | tcgtcacaat | attaaacaag | catctcactg | 180 |
| gtcacttttt | ttttacctat | taaagaacaa | acctttaact | ctcctcacaa | tctgccacgt | 240 |
| gtcgaataat | tgatttactg | agatcaattt | agatcctctc | ccttagactc | ttctcagtac | 300 |
| agctttagat | ctcaacctcc | atgtcagcaa | agttacctta | cgtgtcatcc | tacgtggcct | 360 |
| ctccttctac | ccctcactcc | tccacgtcaa | cattttcctc | caaaattaaa | aaatcatttt | 420 |
| tttattatat | ttacttgaat | gtatataata | atgtctactg | atcttcttct | ttagaactat | 480 |
| ctccttctct | cattggaacc | tcaaaatcat | tcttatttta | tttcgagaaa | aggaaaaaaa | 540 |
| agcacatctg | ttttgaagat | taatttgtgg | attattattg | agcttcatcg | tatttaaaaa | 600 |
| acatagtaaa | agttctttcc | tcatttgtct | ttttattcat | ctaattttt | tagtgaagaa | 660 |
| ccctaattttt | gtttgtgaat | tctcaagttc | aagttttgat | ttgggtattt | tttttgatga | 720 |
| aatttgtgca | gctgtaggat | gttatcgtgc | tgagaaaagg | gttttagatg | gtaagttttt | 780 |
| tttttctttg | atttctctct | cctacttttt | tttttgtttt | gctttagata | atactgtcat | 840 |
| gatatgatat | aaagaattgg | tgatttgggt | agtttatta | acctatgatt | atgtgttatt | 900 |
| tgttttgatc | tttcaattta | tctggtactg | tgtgtatata | tgtttttgttt | tcttcaagt | 960 |
| atttggttat | tattgaagtg | ggtaattagg | aatttgctac | taatctatgg | atttgggttc | 1020 |
| tgttgtgatt | aatttactat | agatttgagg | tttaatttat | gttttatagg | ttagaaaagg | 1080 |
| aaatcaatga | tttgtttgtg | aatttgagta | gattgtttgt | tagtgtgtgt | atgatgatat | 1140 |
| taacttccat | tatttcttcc | ccaaattagg | ggtaattgat | ggttttttgc | ataccgaagg | 1200 |
| cgtattctct | ttgatgatgg | agtgattgtt | gaaaagacat | gatgggttaa | agttgcagga | 1260 |
| ttatttcatt | tcaataaaca | taattgatca | atttggatct | gttgaatgag | gttgattcac | 1320 |
| aaaaatgaag | atgggcccgg | tgttgccaag | tcggtggcag | agcttaatca | acatatagtt | 1380 |
| gctgtgaaaa | aagaaggtag | gggtagggtt | gcaggtgaag | ggcaggggct | ttccgaggag | 1440 |
| gacgaactga | gaattattga | ggatggtgaa | gatgcaaaca | gcaggcgttc | tttgagttct | 1500 |
| gttcagcttc | cagttcatac | tcacaggcct | cagccacaag | tacaacccca | ggggagagtc | 1560 |
| tgttgggaga | ggtttctccc | tgttggatct | cctaaggttt | tgctcgtaga | aagtgatgac | 1620 |
| tcaactcgtc | atattgttag | tgctttgcta | cggaattgta | gctatgaagt | tgtaggggtg | 1680 |
| ccaaatggca | tagaagcatg | gaaaatctta | gaagatttga | gcaatcagat | tgacctagtt | 1740 |
| ttaactgagg | tagtcacatc | aggactctct | ggtataggtc | ttctgtccaa | gataatgagt | 1800 |
| cacaaaagct | gccagaatac | tcctgtcatt | atgatgtcat | ctcatgattc | gatgggttta | 1860 |
| gtcttaaagt | gcttatccaa | gggcgctgtt | gactttctgg | tgaagcctat | aagaaaaaat | 1920 |
| gaacttaaaa | acctttggca | gcatgtttgg | aggaggtgtc | acagttctag | tggtagtgga | 1980 |

```
agtgaaagct gtgtaaggaa tggaaaatcc ataggaagca agagggctga agagtcggac    2040
aatgacactg acagcaatga ggaagatgat aacagaagca ttggtttaca agctcgggat    2100
ggaagtgaca atggaagtgg gacccagagt tcatggacaa aaagggctgc agaagttgag    2160
agcccccaac cacagtctac atgggagcaa gcaactgatc cgcctgatag cacttgtgct    2220
caggtcattt atccaatgtc tgaggcattt gccagcagct ggatgcctgg atccatgcag    2280
gaacttgatg tacaggatca tcaatatgac aatgtcccaa tgggaaagga tttggagatt    2340
ggagtaccta gaatttcaga ttcacggcta aatggaccaa acaaaaaggt taagttagca    2400
actactgctg aggaaaacca atattcacag ttagacctca accaggaaaa tgatggtcga    2460
agttttgatg aagagaacct ggagatgaat aatgataaac ctaaaagtga gtggattaaa    2520
caggctatga actcaccagg aaaagttgaa gaacatcata gaggaaataa agtatctgat    2580
gcaccacccg aaatttccaa aataaaggac aaaggcatgc aacatgtcga ggatatgcct    2640
tctcttgtgc tcagtctgaa gaggttgggt gatattgcag acacgagcac taatgtctca    2700
gaccagaata ttgttgggcg ttcagagctt tcagccttca ccaggtacaa ttcaggcaca    2760
actggtaacc agggtcaaac aggtaatgtt ggcagttgct ctccaccaaa taatagttca    2820
gaagcagcaa agcagtccca ttttgatgct ccacatcaaa tttcgaatag cagtagtaac    2880
aataacaata tgggctctac tactaataag ttcttcaaaa agcctgctat ggacattgat    2940
aagacacctg caaatcaac agtcaactgt tctcatcatt cacatgtgtt tgagccagtg    3000
caaagttccc atatgtctaa taataacctt actgcatctg gtaagcctgg tgttggctcc    3060
gtaaatggta tgctgcaaga aaacgtacca gtaaatgctg ttctgccgca agaaaataac    3120
gtggatcagc agctcaagat tcagcgccac catcactacc atcattacga tgtccataat    3180
gtacagcagc taccaaaggt ttctgttcaa cataatatgt ccaaaagcaa ggatgtgaca    3240 gcaccccac agtgtgggtc ttcaaacact tgtagatcgc caattaaagc aaatgttgcc    3300
aattgcagtt tgaatggaag tggtagtgga agcaatcatg ggagcaattt ccttaatgga    3360
agtagtgctg ctgtgaatgt tgaaggaaca aacatggtca atgatagtgg gatagctgca    3420
aaagatggta ctgaaaatgg aagtggtagt ggaagtggaa gtggtagtgg tagtggtgtt    3480
ggtgtggatc aaagtcgatc agctcaacga gaagctgcct tgaataaatt ccgtctcaag    3540
cgtaaagaaa gatgctttga caaaaaggtg cgatatcaaa gcagaaagaa gttagcagat    3600
caaagacctc gtgttcgtgg gcaattcgtg cgccaggtgc gagaaaacaa aggaaggaat    3660
accgatagct aa                                                        3672
```

<210> SEQ ID NO 54
<211> LENGTH: 4543
<212> TYPE: DNA
<213> ORGANISM: Beta vulgaris

<400> SEQUENCE: 54

```
aaaaaatttc cataaaggtg tatttattag gcgtagcggt tgatttccca aatcattatc      60
cttgcgcaaa ttgcataatg gagatatttg gtgttgacgt ggggccataa ccataatagg     120
gggtcaaaaa caaaactaca agggttaaaa tcgtcacaat attaaacaag catctcactg     180 gtcactttt ttttacctat taaagaacaa acctttaact ctcctcacaa tctgccacgt     240
gtcgaataat tgatttactg agatcaattt agatcctctc ccttagactc ttctcagtac     300
agctttagat ctcaaccctcc atgtcagcaa agttaccttta cgtgtcatcc tacgtggcct     360
```

```
ctccttctac ccctcactcc tccacgtcaa catttttcctc caaaattaaa aaatcatttt    420
tttattatat ttacttgaat gtatataata atgtctactg atcttcttct ttagaactat    480
ctccttctct cattggaacc tcaaaatcat tcttatttta tttcgagaaa aggaaaaaaa    540
agcacatctg ttttgaagat taatttgtgg attattattg agcttcatcg tatttaaaaa    600
acatagtaaa agttctttcc tcatttgtct ttttattcat ctaattttttt tagtgaagaa    660
ccctaattttt gtttgtgaat tctcaagttc aagtttttgat ttgggtatttt ttttttgatga    720
aatttgtgca gctgtaggat gttatcgtgc tgagaaaagg gttttagatg gtaagttttt    780
tttttcttttg atttctctct cctactttttt tttttgtttt gcttttagata atactgtcat    840
gatatgatat aaagaattgg tgatttgggt agtttattta acctatgatt atgtgttatt    900
tgttttgatc tttcaattta tctggtactg tgtgtatata tgttttgttt ttcttcaagt    960
atttggttat tattgaagtg ggtaattagg aatttgctac taatctatgg atttgggttc    1020
tgttgtgatt aatttactat agatttgagg tttaattttat gttttatagg ttagaaaagg    1080
aaatcaatga tttgtttgtg aatttgagta gattgtttgt tagtgtgtgt atgatgatat    1140
taacttccat tatttcttcc ccaaattagg ggtaattgat ggttttttgc ataccgaagg    1200
cgtattctct ttgatgatgg agtgattgtt gaaaagacat gatgggttaa agttgcagga    1260
ttatttcatt tcaataaaca taattgatca atttggatct gttgaatgag gttgattcac    1320
aaaaatgaag atgggcccgg tgttgccaag tcggtggcag agcttaatca acatatagtt    1380
gctgtgaaaa aagaaggtag gggtagggtt gcaggtgaag ggcaggggct ttccgaggag    1440
gacgaactga gaattattga ggatggtgaa gatgcaaaca gcaggcgttc tttgagttct    1500
gttcagcttc cagttcatac tcacaggcct cagccacaag tacaacccca ggggagagtc    1560
tgttgggaga ggtttctccc tgttggatct cctaaggttt tgctcgtaga aagtgatgac    1620
tcaactcgtc atattgttag tgctttgcta cggaattgta gctatgaagt tgtaggggtg    1680
ccaaatggca tagaagcatg gaaaatctta gaagatttga gcaatcagat tgacctagtt    1740
ttaactgagg tagtcacatc aggactctct ggtataggtc ttctgtccaa gataatgagt    1800
cacaaaagct gccagaatac tcctgtcatt atgatgtcat ctcatgattc gatgggttta    1860
gtcttaaagt gcttatccaa gggcgctgtt gactttctgg tgaagcctat aagaaaaaat    1920
gaacttaaaa acctttggca gcatgtttgg aggaggtgtc acagttctag tggtagtgga    1980
agtgaaagct gtgtaaggaa tggaaaatcc ataggaagca agagggctga agagtcggac    2040
aatgacactg acagcaatga ggaagatgat aacagaagca ttggtttaca agctcgggat    2100
ggaagtgaca atggaagtgg gacccagagt tcatggacaa aaagggctgc agaagttgag    2160
agcccccaac cacagtctac atgggagcaa gcaactgatc cgcctgatag cacttgtgct    2220
caggtcatttt atccaatgtc tgaggcattt gccagcagct ggatgcctgg atccatgcag    2280
gaacttgatg tacaggatca tcaatatgac aatgtcccaa tgggaaagga tttggagatt    2340
ggagtaccta gaatttcaga ttcacggcta atggaccaa acaaaaaggt taagttagca    2400
actactgctg aggaaaacca atattcacag ttagacctca accaggaaaa tgatggtcga    2460
agttttgatg aagagaacct ggagatgaat aatgataaac ctaaaagtga gtggattaaa    2520
caggctatga actcaccagg aaaagttgaa gaacatcata gaggaaataa agtatctgat    2580
gcaccacccg aaatttccaa aataaaggac aaaggcatgc aacatgtcga ggatatgcct    2640
tctcttgtgc tcagtctgaa gaggttgggt gatattgcag acacgagcac taatgtctca    2700
gaccagaata ttgttgggcg ttcagagctt tcagccttca ccaggtacaa ttcaggcaca    2760
```

```
actggtaacc agggtcaaac aggtaatgtt ggcagttgct ctccaccaaa taatagttca    2820
gaagcagcaa agcagtccca tttttgatgct ccacatcaaa tttcgaatag cagtagtaac   2880
aataacaata tgggctctac tactaataag ttcttcaaaa agcctgctat ggacattgat    2940
aagacacctg caaaatcaac agtcaactgt tctcatcatt cacatgtgtt tgagccagtg    3000
caaagttccc atatgtctaa taataacctt actgcatctg gtaagcctgg tgttggctcc    3060
gtaaatggta tgctgcaaga aaacgtacca gtaaatgctg ttctgccgca agaaaataac    3120
gtggatcagc agctcaagat tcagcgccac catcactacc atcattacga tgtccataat    3180
gtacagcagc taccaaaggt ttctgttcaa cataatatgt ccaaaagcaa ggatgtgaca    3240 gcaccccac agtgtgggtc ttcaaacact tgtagatcgc caattaaagc aaatgttgcc     3300
aattgcagtt tgaatggaag tggtagtgga agcaatcatg ggagcaattt ccttaatgga    3360
agtagtgctg ctgtgaatgt tgaaggaaca acatggtca atgatagtgg gatagctgca     3420
aaagatggta ctgaaaatgg aagtggtagt ggaagtggaa gtggtagtgg tagtggtgtt    3480
ggtgtggatc aaagtcgatc agctcaacga gaagctgcct tgaataaatt ccgtctcaag    3540
cgtaaagaaa gatgctttga caaaaaggtg cgatatcaaa gcagaaagaa gttagcagat    3600
caaagacctc gtgttcgtgg gcaattcgtg cgccaggtgc gagaaaacaa aggaaggaat    3660
accgatagct aacaccaatt cttttccacaa gttgctgccg agatcattta tgccactctg    3720
atatcagctg tcttcatatg tacaaatttc gaattttatg tgtgcatgag gtgctaaata    3780
ctgtcaaacc tcagtgattc tgtttggttt aggctgtaga aagacatctt ttcctttgtg    3840
ttttcatggt tcttattttg agctgtgttc actactttt ataacatggt agccccaggt     3900
tgcctttgga aataagcttt tccttaaagg tgtgatgcat ataatcttgt ttggtgttag    3960
attatatgat catttcttca ggcgtttacg ggtcacattt tccgggatcc tttcaaacgc    4020
gattccggaa acaatggctc atattttctt ttggtttcaa ggagaaggct atttaaaaca    4080
gaaaagattt aggttacaga aatcagtgat gaagcaatga gtttcattat agaataggtg    4140
gaagtagggg gtgtttttc cgtactcttg agatagaaag tggggataga ttctttggac     4200
tcgtcagaaa ggaataatat aggagttgtc tacctttttc attttagtt cttgtaagag     4260 ttttattcca cttccatttt agtaaaattt aggagttgta aggacgtgta aagagaatct    4320
gccatccaga ttttaaccga cggtaaattt gttcttttca tgttttctca agtaactata    4380
atgttttcat cgaatctaga gggattttct aatgtgtacc tgatagaggc acacagtaac    4440
aataatataa gtacatatat tctttaagaa taatgacata gtaattatat ttttaataca    4500
aataaaagat gtccttatgt aatgaaacaa ataacttttc ctt                      4543
```

<210> SEQ ID NO 55
<211> LENGTH: 23
<212> TYPE: DNA
<213> ORGANISM: Artificial
<220> FEATURE:
<223> OTHER INFORMATION: oligonucleotide sequence - Primer 1r22(T1)-F

<400> SEQUENCE: 55
gataaattct gacccgcatc aca                                             23

<210> SEQ ID NO 56
<211> LENGTH: 28
<212> TYPE: DNA
<213> ORGANISM: Artificial
<220> FEATURE:

```
<223> OTHER INFORMATION: oligonucleotide sequence - Primer 1r22(T1)-R

<400> SEQUENCE: 56
ggactgagtt gataataatc aactttcc                                      28

<210> SEQ ID NO 57
<211> LENGTH: 14
<212> TYPE: DNA
<213> ORGANISM: Artificial
<220> FEATURE:
<223> OTHER INFORMATION: oligonucleotide sequence - Probe 1r22(T1)-VIC

<400> SEQUENCE: 57
cctagcgcaa tttc                                                     14

<210> SEQ ID NO 58
<211> LENGTH: 15
<212> TYPE: DNA
<213> ORGANISM: Artificial
<220> FEATURE:
<223> OTHER INFORMATION: oligonucleotide sequence - probe 1r22(T1)-FAM

<400> SEQUENCE: 58
agctagcgcc caatt                                                    15
```